Figure 7A:
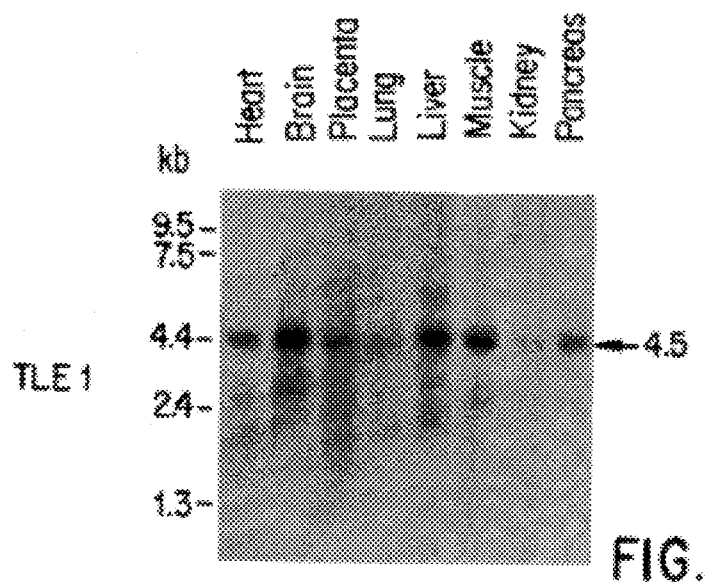

United States Patent [19]

Artavanis-Tsakonas et al.

[11] Patent Number: 5,637,471
[45] Date of Patent: Jun. 10, 1997

[54] THERAPEUTIC AND DIAGNOSTIC METHODS AND COMPOSITIONS BASED ON TRANSDUCIN-LIKE ENHANCER OF SPLIT PROTEINS AND NUCLEIC ACIDS

[75] Inventors: Spyridon Artavanis-Tsakonas, Hamden, Conn.; Stefano Stifani, Edmonton, Canada

[73] Assignee: Yale University, New Haven, Conn.

[21] Appl. No.: 385,207

[22] Filed: Feb. 7, 1995

Related U.S. Application Data

[63] Continuation of Ser. No. 954,813, Sep. 30, 1992, abandoned.
[51] Int. Cl.$^6$ ......................... G01N 33/574; G01N 33/48
[52] U.S. Cl. ...................... 435/7.23; 435/7.9; 436/64; 436/813
[58] Field of Search ........................... 435/7.1, 7.2, 7.22, 435/7.23, 7.9; 530/352; 436/64, 813

[56] References Cited

PUBLICATIONS

Rebay et al., 1991, Specific EGF repeats of Notch mediate interactions with Delta and Serrate: Implications for Notch as a multifunctional receptor, Cell 67:687–699.
Ellisen et al., 1991, TAN–1, the human homolog of the Drosophilia notch gene, is broken by chromosomal translocations in T lymphoblastic neoplasms, Cell 66:649–61.
Haskill et al., 1991, Characterization of an immediate–early gene induced in adherent monocytes that encodes IκB–like activity, Cell 65:1281–89.
Meisner and Czech, 1991, Phosphorylation of transcriptional factors and cell–cycle–dependent proteins by casein kinase II, Curr. Op. Cell Biol. 3:474–83.
Rihs et al., 1991, The rate of nuclear cytoplasmic protein transport is determined by the casein kinase II site flanking the nuclear localization sequence of the SV40 T–antigen, EMBO J. 10:633–39.
Delidakis et al., 1991, Two genetically and molecularly distinct functions involved in early neurogenesis reside within the Enhancer of split locus of Drosophilia melanogaster, Genetics 129:803–23.
Jans et al., 1991, p34$^{cdc2}$-mediated phosphorylation at T$^{124}$ inhibits nuclear import of SV–40 T antigen proteins, J. Cell Biol. 115:1203–12.
Williams et al., 1991, The CYC8 and TUP1 proteins involved in glucose repression in Saccharomyces cerevisiae are associated in a protein complex, Mol. Cell. Biol. 11:3307–16.
Thompson et al., 1991 Convergence of Ets–and Notch–related structural motifs in a heteromeric DNA binding complex, Science 253:762–68.
LaMarco et al., 1991, Identification of Ets–and Notch–related subunits in GA binding protein, Science 253:789–92.
Adams et al., 1991, Complementary DNA sequencing: expressed sequence tags and human genome project, Science 252:1651–56.

Simon et al., 1991, Diversity of G proteins in signal transduction, Science 252:802–08.
Dingwall and Laskey, 1991, Nuclear targeting sequences–a consensus? Trends Biochem. Sci. 16:478–81.
Goebl and Yanagida, 1991, The TPR snap helix: a novel protein repeat motif from mitosis to transcription, Trends Biochem. Sci. 16:173–77.
Ghosh et al., 1990, Cloning of the p50 DNA binding subunit of NF–κB: homology to rel and dorsal, Cell 62:1019–29.
Moreno and Nurse, 1990, Substrates for p34$^{cdc2}$: in vivo veritas? Cell 61:549–51.
Fehon et al., 1990, Molecular interaction between the protein products of the neurogenic loci Notch and Delta, two EGF homologus genes in Drosophila, Cell 61:523–34.
Palka et al., 1990, Neurogenic and antineurogenic effects from modifications at the Notch locus, Development 109:167–75.
Meek et al., 1990, The p53 tumor suppressor protein is phosphorylated at serine 389 by casein kinase II, EMBO J. 9:3253–60.
Smoller et al., 1990, The Drosophila neurogenic locus mastermind encodes a nuclear protein unusually rich in amino acid homopolymers, Genes Dev. 4:1688–1700.
Xu et al., 1990, The Notch locus and the genetic circuitry involved in early Drosophila neurogenesis, Genes Dev. 4:464–75.
Williams and Trumbly, 1990, Characterization of TUP1, a mediator of glucose repression in Saccharomyces cerevisiae, Mol. Cell. Biol. 10:6500–11.
Lüscher et al., 1990, Myb DNA binding inhibited by phosphorylation at a site deleted during oncogenic activation, Nature 344:517–22.
Bischoff et al., 1990, Human p53 is phosphorylated by p60–cdc2 and cyclin B–cdc2, Proc. Natl. Acad. Sci. USA 87:4766–70.
Artavanis-Tsakonas and Simpson, 1991, Choosing a cell fate: a view from the Notch locus, Trends Genet. 7:403–08.
Dalrymple et al., 1989, The product of the PRP4 gene of S. cerevisiae shows homology to β subunits of G proteins, Cell 58:811–12.
Lüscher et al., 1989, Myc oncoproteins are phosphorylated by casein kinase II, EMBO J. 8:1111–19.
Klämbt et al., 1989, Closely related transcripts encoded by the neurogenic gene complex Enhancer of split of Drosophila melanogaster, EMBO J. 8:203–10.
Kidd et al., 1989, Structure and distribution of the Notch protein in developing Drosophila, Genes & Dev. 3:1113–29.

(List continued on next page.)

*Primary Examiner*—Toni R. Scheiner
*Assistant Examiner*—Yvonne Eyler
*Attorney, Agent, or Firm*—Pennie & Edmonds

[57] ABSTRACT

The present invention relates to diagnostic methods and compositions based on transducin-like Enhancer of split ("TLE") proteins and nucleic acids. The invention provides for aiding in the diagnosis of disorders of cell fate or differentiation by determining the level of transducin-like Enhancer of Split (TLE) proteins.

12 Claims, 38 Drawing Sheets

OTHER PUBLICATIONS

Johansen et al., 1989, The Notch gene product is a glycoprotein expressed on the cell surface of both epidermal and neuronal precursor cells during *Drosophila* development, J. Cell. Biol. 109:2427–40.

Ruggieri et al., 1989, MSI1, a negative regulator of the RAS–cAMP pathway in *Saccharomyces cerevisiae*, Proc. Natl. Acad. Sci. USA 86:8778–82.

Hartley et al., 1988, A deduced gene product from the Drosophila neurogenic locus, *Enhancer of split*, shows homology to mammalian G–protein β subunit, Cell 55:785–95.

Preiss et al., 1988, The molecular genetics of *Enhancer of split*, a gene required for embryonic neural development in *Drosophila*, EMBO J. 7:3917–27.

Smith and Johnson, 1988, Single–step purification of polypeptides expressed in *Escherichia coli* as fusions with glutathione S–transferase, Gene 67:31–40.

Dang and Lee, 1988, Identification of the human c–myc protein nuclear translocation signal, Mol. Cell. Biol. 8:4048–54.

Nomura et al., 1988, Isolation of human cDNA clones of myb–related genes, A–myb and B–myb, Nucl. Acids Res. 16:11075–89.

Grässer et al., 1988, In vitro phosphorylation of SV40 large T antigen, Virology 165:13–22.

Knust et al., 1987, Molecular analysis of the neurogenic locus Enhancer of split of *Drosophila melanogaster*, EMBO J. 6:4113–23.

Yochem and Byers, 1987, Structural comparison of the yeast cell division cycle gene CDC4 and a related pseudogene, J. Mol. Biol. 195:233–245.

Breeden and Nasmyth, 1987, Similarity between cell–cycle genes of budding yeast and fission yeast and the *Notch* gene of *Drosophila*, Nature 329:651–54.

Steward, 1987, *Dorsal*, an embryonic polarity gene in *Drosphila*, is homologous to the vertebrate proto–oncogene, c–rel, Science 238:692–94.

Aves et al., 1985, Cloning, sequencing and transcriptional control of the *Schizosaccharomyces pombe* cdc10 'start' gene, EMBO J. 4:457–63.

Vässin et al., 1985, Genetic interactions in early neurogenesis of *Drosophila melanogaster*, J. Neurogenetics 2:291–308.

Jenkins et al., 1984, Cellular immortalization by a cDNA clone encoding the transformation associated phosphoprotein p53, Nature 312:651–54.

Kalderon et al., 1984, Sequence requirements for nuclear location of simian virus 40 large–T antigen, Nature 311:33–38.

Stifani et al., 1992, "Human homologs of a *Drosophila Enhancer of split* gene product define a novel family of nuclear proteins," Nature Genetics 2:119–127, 343.

```
ACAGAGCCCC GCCGCCGCCA GAGCG ATG TTC CCG CAG AGC CGG CAC CCG ACG         52
                              Met Phe Pro Gln Ser Arg His Pro Thr
                               1               5

CCG CAC CAG GCT GCA GGC CAG CCC TTC AAG TTC ACT ATC CCG GAG TCC        100
Pro His Gln Ala Ala Gly Gln Pro Phe Lys Phe Thr Ile Pro Glu Ser
 10              15              20              25

CTG GAC CGG ATT AAA GAG GAA TTC CAG TTC CTG CAG GCG CAG TAT CAC        148
Leu Asp Arg Ile Lys Glu Glu Phe Gln Phe Leu Gln Ala Gln Tyr His
         30              35              40

AGC CTT AAA TTG GAA TGT GAG AAA CTG GCA AGT GAA AAG ACA GAA ATG        196
Ser Leu Lys Leu Glu Cys Glu Lys Leu Ala Ser Glu Lys Thr Glu Met
         45              50              55

CAG AGG CAC TAT GTG ATG TAT GAA ATG TCA TAT GGA TTA AAC ATT            244
Gln Arg His Tyr Val Met Tyr Tyr Glu Met Ser Tyr Gly Leu Asn Ile
         60              65              70

GAA ATG CAC AAA CAG ACT GAA ATC GCC AAG AGA TTG AAT ACG ATT TGT        292
Glu Met His Lys Gln Thr Glu Ile Ala Lys Arg Leu Asn Thr Ile Cys
         75              80              85

GCA CAA GTC ATC CCA TTT CTG TCT CAG GAA CAT CAA CAA CAG GTG GCC        340
Ala Gln Val Ile Pro Phe Leu Ser Gln Glu His Gln Gln Gln Val Ala
         90              95             100             105

FIG.1A
```

FIG. 1B

```
CAG GCT GTT GAA CGT GCC AAA CAG GTG ACC ATG GCA GAG TTG AAT GCC    388
Gln Ala Val Glu Arg Ala Lys Gln Val Thr Met Ala Glu Leu Asn Ala
            110                 115                 120

ATC ATC GGG CAG CAG CAG TTG CAA GCT CAG CAT CTT TCT CAT GGC CAC    436
Ile Ile Gly Gln Gln Gln Leu Gln Ala Gln His Leu Ser His Gly His
            125                 130                 135

GGA CCC CCA GTT CCC CTT ACG CCT CAC CCT TCG GGA CTT CAG CCT CCT    484
Gly Pro Pro Val Pro Leu Thr Pro His Pro Ser Gly Leu Gln Pro Pro
    140                 145                 150

GGA ATC CCG CCC CTC GGG AGT GCC GGC CTT CTT GCG CTG TCT AGT        532
Gly Ile Pro Pro Leu Gly Ser Ala Gly Leu Leu Ala Leu Ser Ser
    155                 160                 165

GCT CTG AGT GGG CAG TCT CAC TTG GCA ATA AAA GAT GAC AAG AAG CAC    580
Ala Leu Ser Gly Gln Ser His Leu Ala Ile Lys Asp Asp Lys Lys His
170                 175                 180                 185
```

```
CAC GAT GCA GAG CAC CAC AGA GAC AGA GAG CCG GGC ACA AGT AAT TCC      628
His Asp Ala Glu His His Arg Asp Arg Glu Pro Gly Thr Ser Asn Ser
190                             195                 200

CTC CTG GTC CCA GAC AGT CTA AGA GGC ACA GAT AAA CGC AGA AAT GGA      676
Leu Leu Val Pro Asp Ser Leu Arg Gly Thr Asp Lys Arg Arg Asn Gly
        205                         210                 215

CCT GAA TTT TCC AAT GAC ATC AAG AAA AGG AAG GTG GAT GAT AAG GAC      724
Pro Glu Phe Ser Asn Asp Ile Lys Lys Arg Lys Val Asp Asp Lys Asp
220                             225                 230

TCC AGC CAC TAT GAC AGT GAT GGT GAC AAA AGC GAT GAC AAC TTA GTT      772
Ser Ser His Tyr Asp Ser Asp Gly Asp Lys Ser Asp Asp Asn Leu Val
235                             240                 245
```

FIG.1C

```
GTG GAT GTG TCT AAT GAG GAC CCT TCT TCT CCG CGA GCA AGC CCT GCC     820
Val Asp Val Ser Asn Glu Asp Pro Ser Ser Pro Arg Ala Ser Pro Ala
250                 255                 260                 265

CAC TCG CCC CGG GAA AAT GGA ATC GAC AAA AAT CGC CTG CTA AAG AAG     868
His Ser Pro Arg Glu Asn Gly Ile Asp Lys Asn Arg Leu Leu Lys Lys
        270                 275                 280

GAT GCT TCT AGC AGT CCA GCT TCC ACG GCC TCC TCG GCA AGT TCC ACT     916
Asp Ala Ser Ser Ser Pro Ala Ser Thr Ala Ser Ser Ala Ser Ser Thr
    285                 290                 295

TCT TTG AAA TCC AAA GAA ATG AGC TTG CAT GAA AAA GCC AGC ACG CCT     964
Ser Leu Lys Ser Lys Glu Met Ser Leu His Glu Lys Ala Ser Thr Pro
300                 305                 310

GTT CTG AAA TCC AGC ACA CCA ACG CCT CGG AGC GAC ATG CCA ACG CCG    1012
Val Leu Lys Ser Ser Thr Pro Thr Pro Arg Ser Asp Met Pro Thr Pro
315                 320                 325

GGC ACC AGC GCC ACT CCA GGC CTC CGT CCA GGT CTC GGC AAG CCT CCA    1060
Gly Thr Ser Ala Thr Pro Gly Leu Arg Pro Gly Leu Gly Lys Pro Pro
        330                 335                 340                 345

GCC ATA GAC CCC CTC GTT AAC CAA GCG GCA GCT GGC TTG AGG ACA CCC    1108
Ala Ile Asp Pro Leu Val Asn Gln Ala Ala Ala Gly Leu Arg Thr Pro
            350                 355                 360
```

FIG. 1D

| CTG | GCA | GTG | CCC | GGC | CCA | TAT | CCT | GCT | CCT | TTT | GGG | ATG | GTC | CCC | CAC | 1156 |
| Leu | Ala | Val | Pro | Gly | Pro | Tyr | Pro | Ala | Pro | Phe | Gly | Met | Val | Pro | His | |
| | | | 365 | | | | 370 | | | | 375 | | | | | |

| GCT | GGC | ATG | AAC | GGC | GAG | CTG | ACC | AGC | CCA | GGC | GCT | GCC | TAC | GCC | AGT | 1204 |
| Ala | Gly | Met | Asn | Gly | Glu | Leu | Thr | Ser | Pro | Gly | Ala | Ala | Tyr | Ala | Ser | |
| | | 380 | | | | | 385 | | | | 390 | | | | | |

| TTA | CAC | AAC | ATG | TCG | CCC | CAG | ATG | AGC | GCA | GCC | GCC | GGC | GGC | CGC | 1252 |
| Leu | His | Asn | Met | Ser | Pro | Gln | Met | Ser | Ala | Ala | Ala | Gly | Gly | Arg | |
| | 395 | | | | | 400 | | | | 405 | | | | | |

| CGT | GGT | TAC | GGG | CGC | TAC | GGG | CGC | ATG | GTG | GGT | TTT | GAT | CCC | CCT | 1300 |
| Arg | Gly | Tyr | Gly | Arg | Tyr | Gly | Arg | Met | Val | Gly | Phe | Asp | Pro | Pro | |
| 410 | | | | | 415 | | | | | 420 | | | | 425 | |

| CAC | ATG | AGA | GTA | CCT | ACC | ATT | CCT | CCA | AAC | CTG | GCA | GGA | ATC | CCT | GGG | 1348 |
| His | Met | Arg | Val | Pro | Thr | Ile | Pro | Pro | Asn | Leu | Ala | Gly | Ile | Pro | Gly | |
| | | | | | 430 | | | | 435 | | | | | 440 | | |

| GGG | AAA | CCT | GCA | TAC | TCC | TTC | CAC | GTT | ACT | GCA | GAC | GGT | CAG | ATG | CAG | 1396 |
| Gly | Lys | Pro | Ala | Tyr | Ser | Phe | His | Val | Thr | Ala | Asp | Gly | Gln | Met | Gln | |
| | | 445 | | | | | 450 | | | | 455 | | | | | |

| CCT | GTC | CCT | TTT | CCC | CCG | ACG | CCC | CTC | ATC | GGA | CCC | GGA | ATC | CCC | CGG | 1444 |
| Pro | Val | Pro | Phe | Pro | Pro | Thr | Pro | Leu | Ile | Gly | Pro | Gly | Ile | Pro | Arg | |
| 460 | | | | | 465 | | | | | 470 | | | | | | |

FIG. 1E

| | | | | | | | | | | | | | | | | |
|---|---|---|---|---|---|---|---|---|---|---|---|---|---|---|---|---|
| CAT | GCT | CGC | CAG | ATC | AAC | ACC | CTC | AAC | CAC | GGG | GAG | GTG | GTG | TGC | GCT | 1492 |
| His | Ala | Arg | Gln | Ile | Asn | Thr | Leu | Asn | His | Gly | Glu | Val | Val | Cys | Ala | |
| 475 | | | | | | 480 | | | | | 485 | | | | | |
| GTG | ACC | ATC | AGC | AAC | CCC | ACG | AGA | CAC | GTG | TAC | ACA | GGC | GGG | AAG | GGC | 1540 |
| Val | Thr | Ile | Ser | Asn | Pro | Thr | Arg | His | Val | Tyr | Thr | Gly | Gly | Lys | Gly | |
| 490 | | | | | 495 | | | | | 500 | | | | | 505 | |
| TGC | GTC | AAG | GTC | TGG | GAC | ATC | AGC | CAC | CCT | GGC | AAT | AAG | AGC | CCT | GTC | 1588 |
| Cys | Val | Lys | Val | Trp | Asp | Ile | Ser | His | Pro | Gly | Asn | Lys | Ser | Pro | Val | |
| | | 510 | | | | | 515 | | | | | 520 | | | | |
| TCC | CAG | CTC | GAC | TGT | CTG | AAC | AGA | GAC | ATC | ATA | AAT | TAT | ATC | CGT | TCC | TGT | AAA | 1636 |
| Ser | Gln | Leu | Asp | Cys | Leu | Asn | Arg | Asp | Asn | Tyr | Ile | Arg | Ser | Cys | Lys | |
| 525 | | | | | 530 | | | | | | | | 535 | | | |
| TTG | CTA | CCC | GAT | GGC | TGC | ACT | CTC | ATA | GTG | GGA | GAA | GGG | GCC | AGT | ACT | 1684 |
| Leu | Leu | Pro | Asp | Gly | Cys | Thr | Leu | Ile | Val | Gly | Glu | Gly | Ala | Ser | Thr | |
| 540 | | | | | | 545 | | | | | 550 | | | | | |
| TTG | TCC | ATT | TGG | GAC | CTG | GCT | CCA | ACC | CCG | CGC | ATC | AAG | GCG | GAG | 1732 |
| Leu | Ser | Ile | Trp | Asp | Leu | Ala | Pro | Thr | Pro | Arg | Ile | Lys | Ala | Glu | |
| 555 | | | | | | 560 | | | | | 565 | | | | | |
| CTG | ACG | TCC | TCG | GCC | CCC | GCC | TGC | TAC | GCC | CTG | AGC | ATC | CCC | GAT | 1780 |
| Leu | Thr | Ser | Ser | Ala | Pro | Ala | Cys | Tyr | Ala | Leu | Ser | Ile | Pro | Asp | |
| 570 | | | | | 575 | | | | | 580 | | | | | 585 | |

FIG.1F

```
TCC AAG GTC TGC TTC TCA TGC TGC AGC GAC GGC AAC ATC GCT GTG TGG      1828
Ser Lys Val Cys Phe Ser Cys Cys Ser Asp Gly Asn Ile Ala Val Trp
            590                 595                 600

GAT CTG CAC AAC CAG ACA CTA GTG AGG CAA TTC CAG GGC CAC ACA GAC      1876
Asp Leu His Asn Gln Thr Leu Val Arg Gln Phe Gln Gly His Thr Asp
            605                 610                 615

GGA GCC AGC TGT ATT GAC ATT TCT AAT GAT GGC ACC AAG CTC TGG ACG      1924
Gly Ala Ser Cys Ile Asp Ile Ser Asn Asp Gly Thr Lys Leu Trp Thr
            620                 625                 630

GGT GGT TTG GAC AAC ACA GTC AGG TCC TGG GAC CTG CGC GAG GGG CGG      1972
Gly Gly Leu Asp Asn Thr Val Arg Ser Trp Asp Leu Arg Glu Gly Arg
            635                 640                 645

CAG CTG CAG CAG CAC GAC TTC ACC TCC CAG ATC TTC TCC CTG GGG TAC      2020
Gln Leu Gln Gln His Asp Phe Thr Ser Gln Ile Phe Ser Leu Gly Tyr
            650                 655                 660                 665

TGC CCC ACC GGG GAG TGG CTG GCA GTG GGC ATG GAG AGC AAT GTG          2068
Cys Pro Thr Gly Glu Trp Leu Ala Val Gly Met Glu Ser Asn Val
            670                 675                 680
```

FIG. 1G

```
GAG GTG CTG CAC GTG AAC AAG CCT GAC AAG TAC CAG CTG CAC CTG CAT    2116
Glu Val Leu His Val Asn Lys Pro Asp Lys Tyr Gln Leu His Leu His
            685                 690                 695

GAG AGC TGC GTG CTG TCC CTG AAA TTT GCT TAC TGT GGT AAA TGG TTT    2164
Glu Ser Cys Val Leu Ser Leu Lys Phe Ala Tyr Cys Gly Lys Trp Phe
        700                 705                 710

GTG AGT ACT GGA AAA GAT AAC CTC CTC AAT GCT TGG CGG ACC CCC TAT    2212
Val Ser Thr Gly Lys Asp Asn Leu Leu Asn Ala Trp Arg Thr Pro Tyr
    715                 720                 725

GGA GCC AGC ATA TTC CAG TCC AAA GAG TCC TCA GTG CTT AGC TGT        2260
Gly Ala Ser Ile Phe Gln Ser Lys Glu Ser Ser Val Leu Ser Cys
730                 735                 740                 745

GAC ATC TCT GTG GAT GAT AAG TAC ATA GTC ACT GGC TCG GGG GAC AAG    2308
Asp Ile Ser Val Asp Asp Lys Tyr Ile Val Thr Gly Ser Gly Asp Lys
        750                 755                 760

AAG GCT ACA GTC TAT GAA GTC ATC TAC TGAAAACATT ATGTGGT             2352
Lys Ala Thr Val Tyr Glu Val Ile Tyr
    765                 770
```

FIG.1H

```
CTGGGGGCT TTTCGAATCG GCAGG ATG TAC CCC CAG GGA AGG CAC CCG ACC         52
                           Met Tyr Pro Gln Gly Arg His Pro Thr
                            1               5

CCG CTC CAG TCC GGC CAG CCC TTC AAG TTC TCG ATC TTG GAG ATC TGC       100
Pro Leu Gln Ser Gly Gln Pro Phe Lys Phe Ser Ile Leu Glu Ile Cys
 10                  15                  20                  25

GAC CGC ATC AAA GAA GAA TTC CAG TTT CTT CAG GCT CAA TAC CAC AGC       148
Asp Arg Ile Lys Glu Glu Phe Gln Phe Leu Gln Ala Gln Tyr His Ser
             30                  35                  40

CTC AAG CTA GAA TGT GAG AAG CTG GCC AGC GAG AAG ACG GAA ATG CAG       196
Leu Lys Leu Glu Cys Glu Lys Leu Ala Ser Glu Lys Thr Glu Met Gln
         45                  50                  55

CGA CAT TAT GTC ATG TAT TAT GAG ATG TCG TAC GGG CTC AAC ATT GAA       244
Arg His Tyr Val Met Tyr Tyr Glu Met Ser Tyr Gly Leu Asn Ile Glu
     60                  65                  70

ATG CAT AAG CAG GCG GAG ATT GTG AAG CGT CTG AGC GGT ATC TGC GCT       292
Met His Lys Gln Ala Glu Ile Val Lys Arg Leu Ser Gly Ile Cys Ala
 75                  80                  85

CAG ATT ATC CCC TTC CTG ACC CAG GAG CAT CAG CAG CAG GTG CTC CAG       340
Gln Ile Ile Pro Phe Leu Thr Gln Glu His Gln Gln Gln Val Leu Gln
 90                  95                  100                 105
```

FIG. 2A

```
                                                                                         388
GCC GTA GAA CGC GCC AAG CAG GTC ACC GTG GGG GAG CTG AAC AGC CTC
Ala Val Glu Arg Ala Lys Gln Val Thr Val Gly Glu Leu Asn Ser Leu
            110             115             120

436
ATC GGG CAG CAG CTC CAG CCG CTG TCC CAC CAC GCA CCC CCT GTG CCC
Ile Gly Gln Gln Leu Gln Pro Leu Ser His His Ala Pro Pro Val Pro
         125             130             135

484
CTC ACC CCC CGC CCA GCC GGG CTG GTG GTG GGC AGT GCT ACG GGG CTG
Leu Thr Pro Arg Pro Ala Gly Leu Val Val Gly Ser Ala Thr Gly Leu
      140             145             150

532
CTT GCT TCT GGA GCC CTG CTG GCT CAG GCT GCA GCG CTG GCG GCT
Leu Ala Ser Gly Ala Leu Leu Ala Gln Ala Ala Ala Leu Ala Ala
   155             160             165

580
GTC AAG GAG CGT GCG GGC GTG GAG GCG GTG TCC AGA GTG GAG GCT
Val Lys Glu Arg Ala Gly Val Glu Ala Val Ser Arg Val Glu Ala
170             175             180             185

628
AGA GCC GAC CGT AGG AGC AGT GCA TCT CCC TCG CCT CCT GAG AGT CTC
Arg Ala Asp Arg Arg Ser Ser Ala Ser Pro Ser Pro Pro Glu Ser Leu
            190             195             200

676
GAG GAG CGA CCG AGT GGC CCT GGT GGG GGC AAG CAG AGA GCA
Glu Glu Arg Pro Ser Gly Pro Gly Gly Gly Lys Gln Arg Ala
         205             210             215
```

FIG.2B

```
GAT GAG AAG GAG CCA TCA GGA CCT TAT GAA AGC GAC GAA AAG AGT    724
Asp Glu Lys Glu Pro Ser Gly Pro Tyr Glu Ser Asp Glu Lys Ser
        220                 225                 230

GAT TAC AAT CTG GTG GTG GAC GAC CAA CCC TCA GAG CCC CCC AGC    772
Asp Tyr Asn Leu Val Val Asp Asp Gln Pro Ser Glu Pro Pro Ser
        235                 240                 245

CCG GCT ACC ACC CCC TGC GGA AAG GTA CCC ATC TGC ATT CCT GCC CGT    820
Pro Ala Thr Thr Pro Cys Gly Lys Val Pro Ile Cys Ile Pro Ala Arg
        250                 255                 260             265

CGG GAC CTG GTG GAC AGT CCA GCC TCC TTG GCC TCT AGC TTG CGG TCA    868
Arg Asp Leu Val Asp Ser Pro Ala Ser Leu Ala Ser Ser Leu Arg Ser
        270                 275                 280

CCG CCT AGA GCC AAG GAG CTC ATC CTG AAT GAC CTT CCC GCC AGC    916
Pro Leu Arg Ala Lys Glu Leu Ile Leu Asn Asp Leu Pro Ala Ser
        285                 290                 295

ACT CCT GCC TCC AAA TCC TGT GAC TCC CCG TCC CCC CAG GAC GCT TCC    964
Thr Pro Ala Ser Lys Ser Cys Asp Ser Pro Ser Pro Gln Asp Ala Ser
        300                 305                 310

ACC CCC GGG CCC AGC TCG GCC AGT CAC CTC TGC AGT CTT GCG CTC AAG    1012
Thr Pro Gly Pro Ser Ser Ala Ser His Leu Cys Ser Leu Ala Leu Lys
        315                 320                 325
```

FIG.2C

```
CCA GCA CCT TCC ACG GAC AGC GTC GCC CTG AGG AGC CCC CTG ACT CTG   1060
Pro Ala Pro Ser Thr Asp Ser Val Ala Leu Arg Ser Pro Leu Thr Leu
330             335             340             345

TCC AGT CCC TTC ACC ACG TCC TTC AGC CTG GGC TCC CAC AGC ACT CTC   1108
Ser Ser Pro Phe Thr Thr Ser Phe Ser Leu Gly Ser His Ser Thr Leu
350             355             360

AAC GGA GAC CTC TCC GTG CCC AGC TCC TAC GTC CAC CTG CAC CTG TCC   1156
Asn Gly Asp Leu Ser Val Pro Ser Ser Tyr Val Ser Leu His Leu Ser
365             370             375

CCC CAG GTC AGC AGC TCT GTG GTG TAC GGA CGC TCC CCC CGT ATG GCA   1204
Pro Gln Val Ser Ser Ser Val Val Tyr Gly Arg Ser Pro Val Met Ala
380             385             390

TTT GAG TCT CAT CCC CAT CTC CGA GGG TCA TCC GTC TCT TCC TCC CTA   1252
Phe Glu Ser His Pro His Leu Arg Gly Ser Ser Val Ser Ser Ser Leu
395             400             405

CCC AGC ATC CCT GGG GGA AAG CCG GCC TAC TCC TTC CAC GTG TCT GCG   1300
Pro Ser Ile Pro Gly Gly Lys Pro Ala Tyr Ser Phe His Val Ser Ala
410             415             420             425

GAC GGG CAG ATG CAG CCG GTT CCC TTC CCC TCG GAT GCA CTG GTA GAC   1348
Asp Gly Gln Met Gln Pro Val Pro Phe Pro Ser Asp Ala Leu Val Asp
430             435             440
```

FIG. 2D

```
GCG GGC ATC CCG CGG CAC GCC CTG CAC ACG CTG GCC CAT GGC      1396
Ala Gly Ile Pro Arg His Ala Leu His Thr Leu Ala His Gly
            445                 450                 455

GAG GTG GTC GCG ACC ATC AGC GGC TCC ACA CAG CAT GTG TAC      1444
Glu Val Val Ala Thr Ile Ser Gly Ser Thr Gln His Val Tyr
            460                 465                 470

ACG GGC AAG GGC TGT GTG GTG AAG GTG TGG GAC GTG CAG CCT GGG  1492
Thr Gly Lys Gly Cys Val Val Lys Val Trp Asp Val Gln Pro Gly
        475                 480                 485

GCC AAG ACG CCC GTG CGC CAG CTC GAC TGC CTG AAC CGA GAC AAC TAC  1540
Ala Lys Thr Pro Val Arg Gln Leu Asp Cys Leu Asn Arg Asp Asn Tyr
    490                 495                 500                 505

ATT CGT TCC TGC AAG TTG CTG CCC GAT GGC CGG AGT CTG ATC GTG GGC  1588
Ile Arg Ser Cys Lys Leu Leu Pro Asp Gly Arg Ser Leu Ile Val Gly
            510                 515                 520

GGT GAG GCC AGC ACC TTG TCC ATT TGG GAC CTG GCG GCG CCC ACC CCC  1636
Gly Glu Ala Ser Thr Leu Ser Ile Trp Asp Leu Ala Ala Pro Thr Pro
    525                 530                 535

CGT ATC AAG GCC GAG CTG ACT TCC TCA GCC CCA GCC TGC TAC GCC CTG  1684
Arg Ile Lys Ala Glu Leu Thr Ser Ser Ala Pro Ala Cys Tyr Ala Leu
    540                 545                 550
```

FIG. 2E

```
GCC GTC AGC CCC GAC GCC AAG GTT TGC TTC TCC TGC AGC GAT GGC   1732
Ala Val Ser Pro Asp Ala Lys Val Cys Phe Ser Cys Ser Asp Gly
555                 560                 565

AAC ATT GTG GTC TGG GAC CTG CAG AAT CAG ACT ATG GTC AGG CAG TTC   1780
Asn Ile Val Val Trp Asp Leu Gln Asn Gln Thr Met Val Arg Gln Phe
        570                 575                 580             585

CAG GGC CAC ACG GAC GGC GCC AGC TGC ATT GAT ATT TCC GAT TAC GGC   1828
Gln Gly His Thr Asp Gly Ala Ser Cys Ile Asp Ile Ser Asp Tyr Gly
    590                 595                 600

ACT CGG CTC TGG ACA GGG GGC CTG GAC AAC ACG GTG CGC TGG GAC   1876
Thr Arg Leu Trp Thr Gly Gly Leu Asp Asn Thr Val Arg Cys Trp Asp
        605                 610                 615

CTG CGG GAG GGC CGC CAG CTG CAG CAT GAC TTC AGC TCC CAG ATT   1924
Leu Arg Glu Gly Arg Gln Leu Gln His Asp Phe Ser Ser Gln Ile
620                 625                 630

TTC TCC CCC TGC CAC TGC CCT AAC CAG GAC TGG CTG GCG GTC GGA ATG   1972
Phe Ser Pro Cys His Cys Pro Asn Gln Asp Trp Leu Ala Val Gly Met
635                 640                 645
```

FIG. 2F

| | | | | | | | | | | | | | | | |
|---|---|---|---|---|---|---|---|---|---|---|---|---|---|---|---|
| GAG | AGT | AGC | AAC | GTG | GAG | ATC | CTG | CAC | GTC | GGC | AAG | CCG | GAG | AAA | TAC | 2020
| Glu | Ser | Ser | Asn | Val | Glu | Ile | Leu | His | Val | Gly | Lys | Pro | Glu | Lys | Tyr |
| 650 | | | | | 655 | | | | | 660 | | | | | 665 |

| CAG | CTG | CAC | CTC | CAC | GAG | AGC | TGC | GTG | CTG | AAG | TTT | GCC | CCT | 2068
| Gln | Leu | His | Leu | His | Glu | Ser | Cys | Val | Leu | Lys | Phe | Ala | Pro |
| | 670 | | | | | 675 | | | | | 680 | | |

| TGC | GGA | CGG | TGG | TTT | GTG | AGC | ACC | GGG | AAG | GAC | AAC | CTG | CTC | AAC | GCC | 2116
| Cys | Gly | Arg | Trp | Phe | Val | Ser | Thr | Gly | Lys | Asp | Asn | Leu | Leu | Asn | Ala |
| | | 685 | | | | | 690 | | | | | 695 | | | |

| TGG | AGG | ACG | CCG | TAC | GGG | GCC | AGC | ATT | TTC | CAG | TCC | AAG | GAG | TCG | TCC | 2164
| Trp | Arg | Thr | Pro | Tyr | Gly | Ala | Ser | Ile | Phe | Gln | Ser | Lys | Glu | Ser | Ser |
| | 700 | | | | | 705 | | | | | 710 | | | | |

| TCA | GTC | CTG | AGT | TGT | GAC | ATC | TCC | AGA | AAT | AAC | AAA | TAC | ATT | GTG | ACA | 2212
| Ser | Val | Leu | Ser | Cys | Asp | Ile | Ser | Arg | Asn | Asn | Lys | Tyr | Ile | Val | Thr |
| 715 | | | | | 720 | | | | | 725 | | | | | |

| GGC | TCG | GGG | GAC | AAG | AAG | GCC | ACC | GTG | TAT | GAG | GTC | GTC | TAC | 2254
| Gly | Ser | Gly | Asp | Lys | Lys | Ala | Thr | Val | Tyr | Glu | Val | Val | Tyr |
| 730 | | | | | 735 | | | | | 740 | | | |

TGAAGACATG ACCCCCC 2271

FIG. 2G

```
GAATCACGAC CCCTCCCTGC C ATG TAT CCG CAG GGC AGA CAT CCG GCT CCC         51
                       Met Tyr Pro Gln Gly Arg His Pro Ala Pro
                        1               5                  10

CAT CAA CCC GGG CAG CCG GGA TTT AAA TTC ACG GTG GCT GAG TCT TGT         99
His Gln Pro Gly Gln Pro Gly Phe Lys Phe Thr Val Ala Glu Ser Cys
                15                  20                  25

GAC AGG ATC AAA GAC GAA TTC CAG TTC CTG CAA GCT CAG TAT CAC AGC        147
Asp Arg Ile Lys Asp Glu Phe Gln Phe Leu Gln Ala Gln Tyr His Ser
                30                  35                  40

CTC AAA GTG ATG TAC GAC AAG CTG GCA AAC GAG AAG ACG GAG ATG CAG        195
Leu Lys Val Met Tyr Asp Lys Leu Ala Asn Glu Lys Thr Glu Met Gln
            45                  50                  55

CGC CAT TAT GTG ATG TAC TAT GAG ATG TCC TAT GGC TTG AAC ATT GAA        243
Arg His Tyr Val Met Tyr Tyr Glu Met Ser Tyr Gly Leu Asn Ile Glu
            60                  65                  70

ATG CAC AAG CAG ACA GAG ATT GCG AAG AGA CTG AAC ACA ATT TTA GCA        291
Met His Lys Gln Thr Glu Ile Ala Lys Arg Leu Asn Thr Ile Leu Ala
                75                  80                  85          90

CAG ATC ATG CCT TTC CTG TCA CAA GAG CAC CAG CAG CAG CAG GTG GCG CAG    339
Gln Ile Met Pro Phe Leu Ser Gln Glu His Gln Gln Gln Gln Val Ala Gln
                    95                  100                 105
```

FIG. 3A

```
GCA GTG GAG CGC GCC AAG CAG GTC ACC ATG ACG GAG CTG AAC GCC ATC    387
Ala Val Glu Arg Ala Lys Gln Val Thr Met Thr Glu Leu Asn Ala Ile
        110              115              120

ATC GGG CAG CAG CAG CTC CAG GCG GCC CAG CAC CTC TCC CAT GCC ACA CAC    435
Ile Gly Gln Gln Gln Leu Gln Ala Ala Gln His Leu Ser His Ala Thr His
        125              130              135

GGC CCC GTC CAG TTG CCA CCC CAC CCG TCA GGT CTC CAG CCT CCA    483
Gly Pro Val Gln Leu Pro Pro His Pro Ser Gly Leu Gln Pro Pro
    140              145              150

GGA ATC CCC CCA GTG ACA GGG AGC TCC TCC GGG AGC TCC TCC GGG CTG GCA CTG CTG GGC    531
Gly Ile Pro Pro Val Thr Gly Ser Ser Ser Gly Ser Ser Ser Gly Leu Ala Leu Leu Gly
    155              160              165              170

GCC CTG GGC AGC CAG GCC CAT CTG ACG GTG AAG GAT GAG AAG AAC CAC    579
Ala Leu Gly Ser Gln Ala His Leu Thr Val Lys Asp Glu Lys Asn His
205     175              180              185

CAT GAA CTC GAT CAC AGA GAA AGA GAA TCC AGT GCC AAT AAC TCT GTG    627
His Glu Leu Asp His Arg Glu Arg Glu Ser Ser Ala Asn Asn Ser Val
        190              195              200

TCA CCC TCG GAA AGC CTC CGG GCC AGT GAG AAG CAC CGG GGC TCT GCG    675
Ser Pro Ser Glu Ser Leu Arg Ala Ser Glu Lys His Arg Gly Ser Ala
        205              210              215
```

FIG. 3B

```
GAC TAC AGC ATG GAA GCC AAG AAG CGG GTG GAG GAG AAG GAC AGC        723
Asp Tyr Ser Met Glu Ala Lys Lys Arg Val Glu Glu Lys Asp Ser
220             225             230

TTG AGC CGA TAC GAC AGT GAT GGA GAC AAG AGT GAT CTG GTG GTG        771
Leu Ser Arg Tyr Asp Ser Asp Gly Asp Lys Ser Asp Leu Val Val
235             240             245             250

GAT GTT TCC AAT GAG GAC CCC GCA ACG CCC CGG GTC AGC CCG GCA CAC    819
Asp Val Ser Asn Glu Asp Pro Ala Thr Pro Arg Val Ser Pro Ala His
                255             260             265

TCC CCT CCT GAA AAT GGG CTG GAC AAG GCC CGT AGC ACA CCT TCC        867
Ser Pro Pro Glu Asn Gly Leu Asp Lys Ala Arg Ser Thr Pro Ser
270             275             280

GCC CCC ACC AGC CCT GCC TCG GTG GCC CGT AGC CTG AAA GAT            915
Ala Pro Thr Ser Pro Ala Ser Val Ala Arg Ser Leu Lys Asp
285             290             295

TCC AAG ACC AAA GAC CTT GGT CAT AAC TCC AGT AGC ACA CCT GGG        963
Ser Lys Thr Lys Asp Leu Gly His Asn Ser Ser Ser Thr Pro Gly
300             305             310

CTC AAG TCC AAC ACA CCA AGG AAC GAC GCC CCA ACT CCA GGC           1011
Leu Lys Ser Asn Thr Pro Arg Asn Asp Ala Pro Thr Pro Gly
315             320             325             330
```

FIG. 3C

```
ACC AGC ACG CCA GGG CTC AGG ATG CCG GGT AAA CCT CCG GGC       1059
Thr Ser Thr Pro Gly Leu Arg Met Pro Gly Lys Pro Pro Gly
            335                 340                 345

ATG GAC CCG GGT ATA ATG GCC TCG GCT CTG CGC ACG CCC TCC       1107
Met Asp Pro Gly Ile Met Ala Ser Ala Leu Arg Thr Pro Ser
            350                 355                 360

ATC ACC AGC TCC TAT GCG GCG CCC TTC GCC ATG ATG AGC CAC CAT GAG  1155
Ile Thr Ser Ser Tyr Ala Ala Pro Phe Ala Met Met Ser His His Glu
            365                 370             375

ATG AAC GGC TCC CTC ACC AGT CCT GGC TAC GCC ATG GCC CTC CAC AAC  1203
Met Asn Gly Ser Leu Thr Ser Pro Gly Tyr Ala Met Ala Gly Leu His Asn
            380                 385                 390

ATC CCA CCC CAG ATG AGC GCC GCT GCA GCT GCC GCT TAT       1251
Ile Pro Pro Gln Met Ser Ala Ala Ala Ala Ala Ala Tyr
            395                 400         405         410

GGC CGA TCG CCA ATG GTG AGC TTT GGA GCT GGT TTT GAC CCT CAC       1299
Gly Arg Ser Pro Met Val Ser Phe Gly Ala Val Gly Phe Asp Pro His
            415                 420                 425

CCC CCG ATG CGG GCC ACA GGG CTC CCC TCA AGC CTG TCC ATT CCT       1347
Pro Pro Met Arg Ala Thr Gly Leu Pro Ser Ser Leu Ser Ile Pro
            430                 435                 440
```

FIG.3D

```
GGA GGA AAA CCA GCG TAC TCA TTC CAT GTG AGT GCT GAT GGG CAG ATG    1395
Gly Gly Lys Pro Ala Tyr Ser Phe His Val Ser Ala Asp Gly Gln Met
         445                 450                 455

CAG CCC GTG CCC TTC CCC CAC GCC CTG GCA GGC CCC ATC CCG            1443
Gln Pro Val Pro Phe Pro His Asp Ala Leu Ala Gly Pro Ile Pro
         460                 465                 470

AGG CAC GCC CGG CAG ATC AAC ACA CTC AGC CAC GGG GTG TGT            1491
Arg His Ala Arg Gln Ile Asn Thr Leu Ser His Gly Val Val Cys
         475                 480                 485                 490

GCC GTG ACC ATC AGC AAC CCC AGC AGG CAC GTC TAC ACA GGT GGC AAG    1539
Ala Val Thr Ile Ser Asn Pro Ser Arg His Val Tyr Thr Gly Gly Lys
         495                 500                 505

GGC TGC GTG AAG ATC TGG GAC CTG AGC ATC AGC AGC CCA AGC AGC CCC    1587
Gly Cys Val Lys Ile Trp Asp Leu Ser Ile Ser Gln Pro Ser Lys Pro
         510                 515                 520

ATC TCC CAG CTG GAC TGC CTG AAC AGG GAC AAT TAC ATG CGC TTC TGC    1635
Ile Ser Gln Leu Asp Cys Leu Asn Arg Asp Asn Tyr Met Arg Ser Cys
         525                 530                 535

AAG CTG CAC CCT GAT GGG CGC ACG CTC ATC GTG GGC GGC GAG GGC AGC    1683
Lys Leu His Pro Asp Gly Arg Thr Leu Ile Val Gly Gly Glu Gly Ser
         540                 545                 550
```

FIG.3E

| ACG Thr 555 | CTC Leu | ACC Thr | ATC Ile | TGG Trp | GAC Asp | CTG Leu | GCC Ala | TCG Ser | CCC Pro | ACG Thr 565 | CCC Pro | CGC Arg | ATC Ile | AAG Lys | GCC Ala 570 | 1731 |
| GAG Glu | CTG Leu | ACG Thr | TCC Ser 575 | TCG Ser | GCT Ala | CCC Pro | GCC Ala | TGT Cys | TAT Tyr 580 | GCC Ala | CTG Leu | GCC Ala | ATT Ile | AGC Ser 585 | CCT Pro | 1779 |
| GAC Asp | GCC Ala | AAA Lys | GTC Val 590 | TGC Cys | TTC Phe | TCC Ser | TGC Cys 595 | TGC Cys | TAT Tyr | GAT Asp | GGG Gly | AAC Asn | ATT Ile 600 | GCT Ala | GTC Val | 1827 |
| TGG Trp | GAC Asp | CTG Leu 605 | CAC His | AAC Asn | CAG Gln | ACC Thr | CTG Leu 610 | GTC Val | AGG Arg | CAG Gln | TTC Phe | CAG Gln 615 | GGC Gly | CAC His | ACA Thr | 1875 |
| GAT Asp | GGG Gly | GCC Ala 620 | AGC Ser | TGC Cys | ATA Ile | GAC Asp | ATC Ile 625 | TCC Ser | CAT His | GAT Asp | GGC Gly 630 | GGT Gly | ACC Thr | AAA Lys | CTG Leu | TGG Trp 1923 |
| ACA Thr 635 | GGG Gly | GGC Gly | CTG Leu | GAC Asp | AAC Asn | ACG Thr 640 | GTG Val | CGC Arg | TCC Ser | TGG Trp | GAC Asp 645 | CTG Leu | CGG Arg | GAG Glu | GGC Gly 650 | 1971 |
| CGA Arg | CAG Gln | CTA Leu | CAG Gln | CAG Gln 655 | CAT His | GAC Asp | TTC Phe | ACT Thr | TCC Ser 660 | CAG Gln | ATC Ile | TTC Phe | TCG Ser | CTG Leu | GGC Gly 665 | 2019 |

FIG. 3F

```
TAC TGC CCC ACT GGG GAG TGG CTG GCT GTG GGC ATG GAG AGC AAC   2067
Tyr Cys Pro Thr Gly Glu Trp Leu Ala Val Gly Met Glu Ser Asn
            670                 675                 680

GTG GAG GTG CTG CAC CAC ACC AAG CCT CAC AAG TAC CAG CTG CAC   2115
Val Glu Val Leu His His Thr Lys Pro His Lys Tyr Gln Leu His
        685                 690                 695

CAC GAG AGC TGC GTG CTC TCC CTC AAG TTC GCC TAC TGC GGC AAG TGG   2163
His Glu Ser Cys Val Leu Ser Leu Lys Phe Ala Tyr Cys Gly Lys Trp
    700                 705                 710

TTC GTG AGC ACT GGG AAA GAT AAC CTT CTC AAC GCC TGG AGG ACG CCT   2211
Phe Val Ser Thr Gly Lys Asp Asn Leu Leu Asn Ala Trp Arg Thr Pro
715                 720                 725                 730

TAT GGA GCC AGC ATA TCC CAG TCT AAA GAA TCC TCG TCT GTC TTG AGT   2259
Tyr Gly Ala Ser Ile Ser Gln Ser Lys Glu Ser Ser Val Leu Ser
            735                 740                 745

TGT GAC ATT TCA GCG GAT GAC AAA TAC ATT GTA ACA GGC TCT GGT GAC   2307
Cys Asp Ile Ser Ala Asp Asp Lys Tyr Ile Val Thr Gly Ser Gly Asp
        750                 755                 760

AAG AAG GCC ACA GTT TAT GAG GTC ATC TAC TAAACAAGAA CTCCAGCAGG   2357
Lys Lys Ala Thr Val Tyr Glu Val Ile Tyr
    765                 770
```

FIG. 3G

| | | | | | | | | | | | | | | | |
|---|---|---|---|---|---|---|---|---|---|---|---|---|---|---|---|
| CCT | ACT | CCA | CGA | ACT | GAT | GCG | CCC | ACC | CCA | GGC | AGT | AAC | TCT | ACT | CCC | 48 |
| Pro | Thr | Pro | Arg | Thr | Asp | Ala | Pro | Thr | Pro | Gly | Ser | Asn | Ser | Thr | Pro |
| 1 | | | | 5 | | | | | 10 | | | | | 15 | |
| GGA | TTG | AGG | CCT | GTA | CCT | GGA | AAA | CCA | CCA | GGA | GTT | GAC | CCT | TTG | GCC | 96 |
| Gly | Leu | Arg | Pro | Val | Pro | Gly | Lys | Pro | Pro | Gly | Val | Asp | Pro | Leu | Ala |
| | | | 20 | | | | | 25 | | | | | 30 | | |
| TCA | AGC | CTA | AGG | ACC | CCA | ATG | GCA | GTA | CCT | TGT | CCA | TAT | CCA | ACT | CCA | 144 |
| Ser | Ser | Leu | Arg | Thr | Pro | Met | Ala | Val | Pro | Cys | Pro | Tyr | Pro | Thr | Pro |
| 35 | | | | | 40 | | | | | 45 | | | | | |
| TTT | GGG | ATT | GTG | CCC | CAT | GCT | GGA | ATG | AAC | GGA | GAG | CTG | ACC | AGC | CCC | 192 |
| Phe | Gly | Ile | Val | Pro | His | Ala | Gly | Met | Asn | Gly | Glu | Leu | Thr | Ser | Pro |
| 50 | | | | | 55 | | | | | 60 | | | | | |
| GGA | GCG | GCC | TAC | GCT | GGG | CTC | CAC | AAC | ATC | TCC | CCT | CAG | ATG | AGC | GCA | 240 |
| Gly | Ala | Ala | Tyr | Ala | Gly | Leu | His | Asn | Ile | Ser | Pro | Gln | Met | Ser | Ala |
| 65 | | | | | 70 | | | | | 75 | | | | | 80 |
| GCT | GCT | GCC | GCC | GCT | GCT | GCT | GCT | GCT | GCT | TAT | GGG | AGA | TCA | CCA | GTG | 288 |
| Ala | Ala | Ala | Ala | Ala | Ala | Ala | Ala | Ala | Ala | Tyr | Gly | Arg | Ser | Pro | Val |
| | | | | 85 | | | | | 90 | | | | | 95 | |
| GTG | GGA | TTT | GAT | CCA | CAC | CAT | CAC | CAT | CAC | ATG | CGT | GTG | CCA | GCA | ATA | CCT | CCA | 336 |
| Val | Gly | Phe | Asp | Pro | His | His | His | His | His | Met | Arg | Val | Pro | Ala | Ile | Pro | Pro |
| | 100 | | | | | 105 | | | | | 110 | | | | | | |

FIG. 4A

```
AAC CTG ACA GGC ATT CCA GGA AAA CCA GCA TAC TCC TTC CAT GTT    384
Asn Leu Thr Gly Ile Pro Gly Lys Pro Ala Tyr Ser Phe His Val
            115             120             125

AGC GCA GAT GGT CAG ATG CAG ATG CCT GTC CCT TTT CCA CCC CTC    432
Ser Ala Asp Gly Gln Met Gln Met Pro Val Pro Phe Pro Pro Leu
            130             135             140

ATC GGA CCT GGG ATC CCC CGG CAT GCT CGC CAG ATC AAC ACC CTC    480
Ile Gly Pro Gly Ile Pro Arg His Ala Arg Gln Ile Asn Thr Leu
            145             150             155             160

CAC GGG GAG GTG GTG TGC GTG ACC ATC AGC AAC CCC ACG AGA CAC    528
His Gly Glu Val Val Cys Val Thr Ile Ser Asn Pro Thr Arg His
            165             170             175

GTG TAC ACG GGT GGG AAG GGC GCG GTC AAG GTC TGG GAC ATC AGC    576
Val Tyr Thr Gly Gly Lys Gly Ala Val Lys Val Trp Asp Ile Ser
            180             185             190

CCA GGC AAT AAG AGT CCT GTC TCC CAG CTC GAC TGT CTG AAC AGG    624
Pro Gly Asn Lys Ser Pro Val Ser Gln Leu Asp Cys Leu Asn Arg
            195             200             205

AAC TAC ATC CGT TCC TGC AGA TTG CTC CCT GAT GGT CGC ACC CTA    672
Asn Tyr Ile Arg Ser Cys Arg Leu Leu Pro Asp Gly Arg Thr Leu
            210             215             220
```

FIG. 4B

```
GTT GGA GGG GAA GCC AGT ACT TTG TCC ATT TGG GAC CTG GCG GCT CCA      720
Val Gly Gly Glu Ala Ser Thr Leu Ser Ile Trp Asp Leu Ala Ala Pro
225             230                 235                 240

ACC CCA CGC ATC AAG GCA GAG CTG ACA TCC TCG GCC CCC GCC TGC TAT      768
Thr Pro Arg Ile Lys Ala Glu Leu Thr Ser Ser Ala Pro Ala Cys Tyr
            245                 250                 255

GCC CTG GCC ATC AGC CCC GAT TCC AAG GTC TGC TTC TCA TGC TGC AGC      816
Ala Leu Ala Ile Ser Pro Asp Ser Lys Val Cys Phe Ser Cys Cys Ser
            260                 265                 270

GAC GGC AAC ATC GCT GTG TGG GAT CTG CAC AAC CAG ACC TTG GTG AGG      864
Asp Gly Asn Ile Ala Val Trp Asp Leu His Asn Gln Thr Leu Val Arg
            275                 280                 285

CAA TTC CAG GGC CAC ACA GAT GGA GCC AGC TGT ATT GAC ATT TCT AAT      912
Gln Phe Gln Gly His Thr Asp Gly Ala Ser Cys Ile Asp Ile Ser Asn
            290                 295                 300

GAT GGC ACC AAG CTC TGG ACA GGT TTG GAC AAC ACG GTC AGG TCC          960
Asp Gly Thr Lys Leu Trp Thr Gly Leu Asp Asn Thr Val Arg Ser
            305                 310                 315          320

TGG GAC CTG CGG GAG GGG CGG CAG CTG CAG CAC CAG CAC GAC TTC ACC TCC  1008
Trp Asp Leu Arg Glu Gly Arg Gln Leu Gln His Gln His Asp Phe Thr Ser
            325                 330                 335
```

FIG. 4C

```
CAG ATC TTT TCT CTG GGC TAC TGC CCA ACT GGA GAG TGG CTT GCA GTG  1056
Gln Ile Phe Ser Leu Gly Tyr Cys Pro Thr Gly Glu Trp Leu Ala Val
            340                 345                 350

GGG ATG GAG AAC AGC AAT GTG GAA GTT TTG CAT GTC ACC AAG CCA GAC  1104
Gly Met Glu Asn Ser Asn Val Glu Val Leu His Val Thr Lys Pro Asp
            355                 360                 365

AAA TAC CAA CTA CAT CTT CAT GAG AGC TGT GTG CTG TCG CTC AAG TTT  1152
Lys Tyr Gln Leu His Leu His Glu Ser Cys Val Leu Ser Leu Lys Phe
            370                 375                 380

GCC CAT TGT GGC AAA TGG TTT GTA AGC ACT GGA AAG GAC AAC CTT CTG  1200
Ala His Cys Gly Lys Trp Phe Val Ser Thr Gly Lys Asp Asn Leu Leu
            385                 390                 395             400

AAT GCC TGG AGA ACG CCT TAC GGG GCC AGT ATA TTC CAG TCC AAA GAA  1248
Asn Ala Trp Arg Thr Pro Tyr Gly Ala Ser Ile Phe Gln Ser Lys Glu
            405                 410                 415
```

FIG. 4D

```
TCC TCA TCG GTG CTT AGC TGT GAC ATC TCC GTG GAC GAC AAA TAC ATT    1296
Ser Ser Ser Val Leu Ser Cys Asp Ile Ser Val Asp Asp Lys Tyr Ile
            420                 425                 430

GTC ACT GGC TCT GGG GAT AAG AAG GCC ACA GTT TAT GAA GTT ATT TAT    1344
Val Thr Gly Ser Gly Asp Lys Lys Ala Thr Val Tyr Glu Val Ile Tyr
            435                 440                 445

TAAAGACAAA TCTTCATGCA GACTGGACTT CTCCTCCTGG TAGCACTTTG CTCTGTCATC  1404

CTTTTGTTC ACCCCCATCC CCGCATCTAA AACCAAGGA                          1443
```

FIG. 4E

Q Domain

|  |  |  |
|---|---|---|
| E(spl)m9/10 | 1 | MYPSPVRHPAAGQPPPQGPIKFTIADTLERTKEEFNFLQAHYHSIKLECEKLSNEKTEMQRHYVMYYE |
| TLE 1 | 1 | MFPQS-RHPTPHQAAGQ-PFKFTIPESLDRIKEEFQFLQAQYHSLKLECEKIASEKTEMQRHYVMYYE |
| TLE 2 | 1 | MYPQG-RHPTPLQS-GQ-PFKFSILEICDRIKEEFQFLQAQYHSLKLECEKLASEKTEMQRHYVMYYE |
| TLE 3 | 1 | MYPQG-RHPAPHQP-GQPGFKFTVAESCDRIKQEFQFLQAQYHSLKVEYDKLANEKTEMQRHYVMYYE |

|  |  |  |
|---|---|---|
| E(spl)m9/10 | 69 | MSYGLNIEMHKQIEIAKRINTLINQLPFTQADHQQQVLQAVERAKQVTMQELNLIIGQQIHAQ-Q |
| TLE 1 | 67 | MSYGLNIEMHKQAEIAKRLNTICAQVIPFLSQEHQQQVAQAVERAKQVTMAELNAIIGQQ—QLQAQ |
| TLE 2 | 66 | MSYGLNIEMHKQAEIVKRLSGICAQIIPFLTQEHQQQVLQAVERAKQVTVGELNSLIIGQQ——LQ |
| TLE 3 | 66 | MSYGLNIEMHKQIEIAKRINTILAQIMPFLSQEHQQQVAQAVERAKQVTMTELNAIIGQQ-QLQAQ |

GP Domain

|  |  |  |
|---|---|---|
| E(spl)m9/10 | 134 | V—PGGPPQPMGALNPFGALGATMCLPHQPQ-GLLNKPPEHRPDIK—PTGLEGPAA-AEERIR—-NS |
| TLE 1 | 132 | HLSH-GHGPPVPLTPHPSGLQPPGIPPL—GGSA-GLLALSSALSGQSHLA—IKDDKKHHDA-EHHR-DREPGTS |
| TLE 2 | 128 | PLSH—HAPPVPLTPRP——AG—LVGGSATGLLALSGALAAQAQLAAVKEDRAGVEA-EGSRVERAPSRS— |
| TLE 3 | 131 | HLSHATHGPPVQLPPHPSGLQPPGIPPVTG-SSSGLLALG-ALGSQAHLT—VKDEKNHHEL-DH-RI-ER—-ESSA |

CcN Domain

|  |  |  |
|---|---|---|
| E(spl)m9/10 | 195 | ——-VSPAD——REK-YRTRSPLDIENDSKRRK-DEKLQEDEGEKSDQD———LVVDVANE-MESHSPRPNGEHVS |
| TLE 1 | 200 | NSLLVP-DSLRGTDKRRNGP-EFSNDIKRKVDDKO-SSHYD-SDGDKSDDNLVVDSNED—PS-SPRASPAHSP |
| TLE 2 | 192 | ASP-SPPESLVE-EERPSGP——-GGGQKQR-ADEKEPSGPYE-SDEDKSDYNLVVD——EDQPSE-P-PSPATTP |
| TLE 3 | 198 | NNSVSDSEISLRASEKHRGSA-DYSMEAKKRKVEEKDSLSRYD-SDGQKSDD-LVVDSNED-PLATPRVSPAHSP |

FIG.5A

SP Domain

| | | |
|---|---|---|
| E(spl)m9/10 | 257 | MEVRDRESLNGER-LEKPSSSGIKQERPPSRGSGSSSRSTPSLKTKDM——EKP-GTPGAKA |
| TLE 1 | 269 | RENG-IDKNRLLKKDA—SSSPASTA————————SSASST-SLKSXEMSLHEK-ASTPVLKS |
| TLE 2 | 255 | CGKVPICIPA—RRDL—VDSPASLA————————SSLRS-PLPRAKELILNDLPASTPASXS |
| TLE 3 | 268 | PENG-LDKARSLKKDA—PTSPASVA————————SSS-STPSSKTKDLGHNDK-SSITPGLKS |

| | | |
|---|---|---|
| E(spl)m9/10 | 314 | RTPTPNAAPAPGVNPKQMPQ——GPPPAGYFGAPYQR———P-ADPYQRPPSDPA |
| TLE 1 | 318 | STPTPRSDMPTPG-TSATP-GLRPGLGKPPAIDPLVNQAAAGLRTPLAVPGPYPAPFGMVP-AGMNGE |
| TLE 2 | 304 | CDSSPPQDASTPGPSSASH—LCQLALK-PA—PSTDSVA—LRSPLTLSSPFTTSFSLGS-STLNGD |
| TLE 3 | 317 | NTPTPRNDAPTPG—TSTTP-GLRSMPGKPPGMDPIGIMASA—LRTPISITSSYAAPFAMMSHHEMNGS |
| TLE 4 | | PTPRTDAPTPG——SNSTPGLRPVPGKPPGVDPL——ASS-LRTPMAVPCPYPTPFGIVP-AGMNGE |

| | | |
|---|---|---|
| E(spl)m9/10 | 363 | YGRPPPMPYDPHAHVRTNG———IPHPSALT-CGKPAYSFH |
| TLE 1 | 384 | LTSFGAAYASLHNMSPQMSAAAA-RGRRGRYGRSPMVGFDPPPHMRVPT———IPPNLAGIPGGKPAYSFH |
| TLE 2 | 365 | LSVPFS-SYMVSLH-LSPQ————VSSSVVYGRSPVMAFESHPHLRGSS———VSSSLPSIPGGKPAYSFH |
| TLE 3 | 382 | LTSPG-AYYAGLHNIPPQMSAAAAAAAAA——YGRSPMVSFGAVGFDPHPPMRATGLPSSLASIPGGKPAYSFH |
| TLE 4 | | LTSPGAAMYAGLHNISPQMSAAAAAAAAAAYGRSPVVGFDPHHHMRVPA———IPPNLTGIPGGKPAYSFH |

WD-40 Domain

| | | |
|---|---|---|
| E(spl)m9/10 | 399 | MNGEGSLQPVPFPPDALVGVGIPRHARQINTLSHGEVVCAVTISNPTKYVYTGGKGCVKVWDISQPG |
| TLE 1 | 450 | VTADQMQPVPFPPTPLIGFPGIPRHARQINTLNHGEVVCAVTISNPTRHVYTGKGCVKVWDISHPG |
| TLE 2 | 423 | VSADQMQPVPFPSDALVDAGIPRHARQIHTLAHGEVVCAVTISGSTQHVYTGKGCVKVWDVGQPG |
| TLE 3 | 451 | VSADQMQPVPFHDALAGRGIPRHARQIPRTLSHGGVVCAVTISNPSRHVYTGGKGCVKVIWDISQPG |
| TLE 4 | | VSADQMQPVPFPDPLIGRGIPRHARQINTLNHGEVVCAVTISNPTRHVYTGGKGAVKVWDISHPG |

FIG.5B

| | | |
|---|---|---|
| E(spl)m9/10 | 466 | NKNPVSQLDCLNRDNYMIRSVKLLPDGRTLIVGGEASNLSIWDLASPTPRIKAELTSAAPACYALAIS |
| TLE 1 | 517 | NKSPVSQLDCLNRDNYMIRSCKLLPDGRSLIVGGEASTLSIWDLAAPTPRIKAELTSSAPACYALAIS |
| TLE 2 | 490 | AKTPVRQLDCLNRDNYMIRSCKLLPDGRTLIVGGEASTLSIWDLTAPTPRIKAELTSSAPACYALAVS |
| TLE 3 | 518 | SKQPISQLDCLNRDNYMIRSCKLLPDGRSLITVGGEGSTLTIWDLASPTPRIKAELTSSAPACYALAIS |
| TLE 4 | | NKSPVSQLDCLNRDNYMIRSCRLLPDGRTLIVGGEASTLSIWDLAAPTPRIKAELTSSAPACYALAIS |
| | | |
| E(spl)m9/10 | 533 | PDSKVCFSCCSDGNIAVWDLHNEILVRQFQGHIDGASCIDISPDQSRLWTGGLDNTVRSWDLREGRQ |
| TLE 1 | 584 | PDSKVCFSCCSDGNIAVWDLHNQTLVRQFQGHIDGASCIDISNDGTKLWTGGLDNTVRSWDLREGRQ |
| TLE 2 | 557 | PDAKVCFSCCSDGNIVVWDLQNQTMVRQFQGHIDGASCIDISDYGTRLWTGGLDNTVRCWDLREGRQ |
| TLE 3 | 585 | PDAKVCFSCCSDGNIAVWDLHNQTLVRQFQGHIDGASCIDISHDGTKLWTGGLDNTVRSWDLREGRQ |
| TLE 4 | | PDSKVCFSCCSDGNIAVWDLHNQTLVRQFQGHIDGASCIDISNDGTKLWTGGLDNTVRSWDLREGRQ |
| | | |
| E(spl)m9/10 | 600 | LQQHDFSSQIFSLGYCPTGDWLAVGMENSHVEMHASKPDKYQLHLHESCVLSLKFAACGKMFVSTG |
| TLE 1 | 651 | LQQHDFTSQIFSLGYCPTGEWLAVGMESSNVEMLHVNKPDKYQLHLHESCVLSLKFAYCGKMFVSTG |
| TLE 2 | 624 | LQQHDFSSQIFSPCHCPNQDWLAVGMESSNVEIILHVGKPEKYQLHLHESCVLSLKFAPCGRMFVSTG |
| TLE 3 | 652 | LQQHDFTSQIFSLGYCPTGEWLAVGMESSNVEMLHHTKPHKYQLHLHESCVLSLKFAYCGKMFVSTG |
| TLE 4 | | LQQHDFTSQIFSLGYCPTGEWLAVGMENSNVEVLHVTKPDKYQLHLHESCVLSLKEAHCGKMFVSTG |
| | | |
| E(spl)m9/10 | 667 | KDNLLNAWRTPYGASIFQSKETSSVLSCDISIDDKYIVTGSGDKKATVYEVIM |
| TLE 1 | 718 | KDNLLNAWRTPYGASIFQSKESSSVLSCDISVDDKYIVTGSGDKKATVYEVIM |
| TLE 2 | 619 | KDNLLNAWRTPYGASIFQSKESSSVLSCDISPNNKYIVTGSGDKKATVYEVMM |
| TLE 3 | 719 | KDNLLNAWRTPYGASISQSKESSSVLSCDISADDKYIVTGSGDKKATVYEVIM |
| TLE 4 | | KDNLLNAWRTPYGASIFQSKESSSVLSCDISVDDKYIVTGSGDKKATVYEVIM |

FIG.5C

REPEAT 1

| | | |
|---|---|---|
| E(spl) m9/10 | 419 | GIPRHARQINTLSHGEVVCAVTISNPTKYVYTGGKGCVKVWDIS |
| TLE 1 | 470 | GIPRHARQINTLNHGEVVCAVTISNPTRHVYTGGKGCVKVWDIS |
| TLE 2 | 443 | GIPRHARQLHTLAHGEVVCAVTISGSTQHVYTGGKGCVKVWDVG |
| TLE 3 | 471 | GIPRHARQINTLSHGGVVCAVTISNPSRHVYTGGKGCVKIWDIS |
| TLE 4 | | GIPRHARQINTLNHGEVVCAVTISNPTRHVYTGGKGAVKVWDIS |

REPEAT 2

| | | |
|---|---|---|
| E(spl) m9/10 | 463 | QPGNKNPVSQLDCLQRDNYIRSVKLLPDGRTLIVGGEASNLSIWDLA |
| TLE 1 | 514 | HPGNKSPVSQLDCLNRDNYIRSCKLLPDGCTLIVGGEASTLSIWDLA |
| TLE 2 | 487 | QPGAKTPVRQLDCLNRDNYIRSCKLLPDGRSLIVGGEASTLSIWDLA |
| TLE 3 | 515 | QPGSKSPISQLDCLNRDNYMRSCKLHPDGRTLIVGGEGSTLTIWDLA |
| TLE 4 | | HPGNKSPVSQLDCLNRDNYIRSCRLLPDGRTLIVGGEASTLSIWDLA |

REPEAT 3

| | | |
|---|---|---|
| E(spl) m9/10 | 510 | ---SPTPRIKAELTSAAPACYALAISPDSKVCFSCCSDGNIAVWDLH |
| TLE 1 | 561 | ---APTPRIKAELTSSAPACYALAISPDSKVCFSCCSDGNIAVWDLH |
| TLE 2 | 534 | ---APTPRIKAELTSSAPACYALAVSPDAKVCFSCCSDGNIVVWDLQ |
| TLE 3 | 562 | ---SPTPRIKAELTSSAPACYALAISPDAKVCFSCCSDGNIAVWDLH |
| TLE 4 | | ---APTPRIKAELTSSAPACYALAISPDSKVCFSCCSDGNIAVWDLH |

REPEAT 4

| | | |
|---|---|---|
| E(spl) m9/10 | 554 | ----NEILVRQFQGHTDGASCIDISPDGSRLWTGGLDNTVRSWDLR |
| TLE 1 | 605 | ----NQTLVRQFQGHTDGASCIDISNDGTKLWTGGLDNTVRSWDLR |
| TLE 2 | 578 | ----NQTMVRQFQGHTDGASCIDISDYGTRLWTGGLDNTVRCWDLR |
| TLE 3 | 606 | ----NQTLVRQFQGHTDGASCIDISHDGTKLWTGGLDNTVRSWDLR |
| TLE 4 | | ----NQTLVRQFQGHTDGASCIDISNDGTKLWTGGLDNTVRSWDLR |

Consensus ------P----D-T---------I-ISPDGT-L-TGG-DG-V---WDL-
                      E           LL     S    S

FIG. 6

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 2352 base pairs
        ( B ) TYPE: nucleic acid
        ( C ) STRANDEDNESS: single
        ( D ) TOPOLOGY: unknown ( i i ) MOLECULE TYPE: DNA (cDNA)

( i x ) FEATURE:
        ( A ) NAME/KEY: CDS
        ( B ) LOCATION: 26..2335

( x i ) SEQUENCE DESCRIPTION: SEQ ID NO:1:

```
ACAGAGCCCC  GCCGCCGCCA  GAGCG  ATG  TTC  CCG  CAG  AGC  CGG  CAC  CCG  ACG         52
                               Met  Phe  Pro  Gln  Ser  Arg  His  Pro  Thr
                                1                  5

CCG  CAC  CAG  GCT  GCA  GGC  CAG  CCC  TTC  AAG  TTC  ACT  ATC  CCG  GAG  TCC    100
Pro  His  Gln  Ala  Ala  Gly  Gln  Pro  Phe  Lys  Phe  Thr  Ile  Pro  Glu  Ser
 10                 15                       20                       25

CTG  GAC  CGG  ATT  AAA  GAG  GAA  TTC  CAG  TTC  CTG  CAG  GCG  CAG  TAT  CAC    148
Leu  Asp  Arg  Ile  Lys  Glu  Glu  Phe  Gln  Phe  Leu  Gln  Ala  Gln  Tyr  His
                     30                       35                       40

AGC  CTT  AAA  TTG  GAA  TGT  GAG  AAA  CTG  GCA  AGT  GAA  AAG  ACA  GAA  ATG    196
Ser  Leu  Lys  Leu  Glu  Cys  Glu  Lys  Leu  Ala  Ser  Glu  Lys  Thr  Glu  Met
             45                       50                       55
```

| | | | | | | | | | | | | | | | | |
|---|---|---|---|---|---|---|---|---|---|---|---|---|---|---|---|---|
| CAG | AGG | CAC | TAT | GTG | ATG | TAT | TAT | GAA | ATG | TCA | TAT | GGA | TTA | AAC | ATT | 244 |
| Gln | Arg | His | Tyr | Val | Met | Tyr | Tyr | Glu | Met | Ser | Tyr | Gly | Leu | Asn | Ile | |
| | | 60 | | | | 65 | | | | | 70 | | | | | |
| GAA | ATG | CAC | AAA | CAG | ACT | GAA | ATC | GCC | AAG | AGA | TTG | AAT | ACG | ATT | TGT | 292 |
| Glu | Met | His | Lys | Gln | Thr | Glu | Ile | Ala | Lys | Arg | Leu | Asn | Thr | Ile | Cys | |
| | 75 | | | | 80 | | | | 85 | | | | | | | |
| GCA | CAA | GTC | ATC | CCA | TTT | CTG | TCT | CAG | GAA | CAT | CAA | CAA | CAG | GTG | GCC | 340 |
| Ala | Gln | Val | Ile | Pro | Phe | Leu | Ser | Gln | Glu | His | Gln | Gln | Gln | Val | Ala | |
| 90 | | | | | 95 | | | | | 100 | | | | | 105 | |
| CAG | GCT | GTT | GAA | CGT | GCC | AAA | CAG | GTG | ACC | ATG | GCA | GAG | TTG | AAT | GCC | 388 |
| Gln | Ala | Val | Glu | Arg | Ala | Lys | Gln | Val | Thr | Met | Ala | Glu | Leu | Asn | Ala | |
| | | | 110 | | | | 115 | | | | | | 120 | | | |
| ATC | ATC | GGG | CAG | CAG | CAG | TTG | CAA | GCT | CAG | CAT | CTT | TCT | CAT | GGC | CAC | 436 |
| Ile | Ile | Gly | Gln | Gln | Gln | Leu | Gln | Ala | Gln | His | Leu | Ser | His | Gly | His | |
| | | | 125 | | | | 130 | | | | | | 135 | | | |
| GGA | CCC | CCA | GTT | CCC | CTT | ACG | CCT | CAC | CCT | TCG | GGA | CTT | CAG | CCT | CCT | 484 |
| Gly | Pro | Pro | Val | Pro | Leu | Thr | Pro | His | Pro | Ser | Gly | Leu | Gln | Pro | Pro | |
| | | 140 | | | | 145 | | | | | 150 | | | | | |
| GGA | ATC | CCG | CCC | CTC | GGG | GGC | AGT | GCC | GGC | CTT | CTT | GCG | CTG | TCT | AGT | 532 |
| Gly | Ile | Pro | Pro | Leu | Gly | Gly | Ser | Ala | Gly | Leu | Leu | Ala | Leu | Ser | Ser | |
| | 155 | | | | 160 | | | | | 165 | | | | | | |
| GCT | CTG | AGT | GGG | CAG | TCT | CAC | TTG | GCA | ATA | AAA | GAT | GAC | AAG | AAG | CAC | 580 |
| Ala | Leu | Ser | Gly | Gln | Ser | His | Leu | Ala | Ile | Lys | Asp | Asp | Lys | Lys | His | |
| 170 | | | | | 175 | | | | | 180 | | | | | 185 | |
| CAC | GAT | GCA | GAG | CAC | CAC | AGA | GAC | AGA | GAG | CCG | GGC | ACA | AGT | AAT | TCC | 628 |
| His | Asp | Ala | Glu | His | His | Arg | Asp | Arg | Glu | Pro | Gly | Thr | Ser | Asn | Ser | |
| | | | | 190 | | | | | 195 | | | | | 200 | | |
| CTC | CTG | GTC | CCA | GAC | AGT | CTA | AGA | GGC | ACA | GAT | AAA | CGC | AGA | AAT | GGA | 676 |
| Leu | Leu | Val | Pro | Asp | Ser | Leu | Arg | Gly | Thr | Asp | Lys | Arg | Arg | Asn | Gly | |
| | | | 205 | | | | 210 | | | | | | 215 | | | |
| CCT | GAA | TTT | TCC | AAT | GAC | ATC | AAG | AAA | AGG | AAG | GTG | GAT | GAT | AAG | GAC | 724 |
| Pro | Glu | Phe | Ser | Asn | Asp | Ile | Lys | Lys | Arg | Lys | Val | Asp | Asp | Lys | Asp | |
| | | 220 | | | | 225 | | | | | 230 | | | | | |
| TCC | AGC | CAC | TAT | GAC | AGT | GAT | GGT | GAC | AAA | AGC | GAT | GAC | AAC | TTA | GTT | 772 |
| Ser | Ser | His | Tyr | Asp | Ser | Asp | Gly | Asp | Lys | Ser | Asp | Asp | Asn | Leu | Val | |
| | 235 | | | | 240 | | | | | 245 | | | | | | |
| GTG | GAT | GTG | TCT | AAT | GAG | GAC | CCT | TCT | TCT | CCG | CGA | GCA | AGC | CCT | GCC | 820 |
| Val | Asp | Val | Ser | Asn | Glu | Asp | Pro | Ser | Ser | Pro | Arg | Ala | Ser | Pro | Ala | |
| 250 | | | | | 255 | | | | | 260 | | | | | 265 | |
| CAC | TCG | CCC | CGG | GAA | AAT | GGA | ATC | GAC | AAA | AAT | CGC | CTG | CTA | AAG | AAG | 868 |
| His | Ser | Pro | Arg | Glu | Asn | Gly | Ile | Asp | Lys | Asn | Arg | Leu | Leu | Lys | Lys | |
| | | | | 270 | | | | | 275 | | | | | 280 | | |
| GAT | GCT | TCT | AGC | AGT | CCA | GCT | TCC | ACG | GCC | TCC | TCG | GCA | AGT | TCC | ACT | 916 |
| Asp | Ala | Ser | Ser | Ser | Pro | Ala | Ser | Thr | Ala | Ser | Ser | Ala | Ser | Ser | Thr | |
| | | | 285 | | | | 290 | | | | | 295 | | | | |
| TCT | TTG | AAA | TCC | AAA | GAA | ATG | AGC | TTG | CAT | GAA | AAA | GCC | AGC | ACG | CCT | 964 |
| Ser | Leu | Lys | Ser | Lys | Glu | Met | Ser | Leu | His | Glu | Lys | Ala | Ser | Thr | Pro | |
| | | 300 | | | | 305 | | | | | 310 | | | | | |
| GTT | CTG | AAA | TCC | AGC | ACA | CCA | ACG | CCT | CGG | AGC | GAC | ATG | CCA | ACG | CCG | 1012 |
| Val | Leu | Lys | Ser | Ser | Thr | Pro | Thr | Pro | Arg | Ser | Asp | Met | Pro | Thr | Pro | |
| | 315 | | | | 320 | | | | | 325 | | | | | | |
| GGC | ACC | AGC | GCC | ACT | CCA | GGC | CTC | CGT | CCA | GGT | CTC | GGC | AAG | CCT | CCA | 1060 |
| Gly | Thr | Ser | Ala | Thr | Pro | Gly | Leu | Arg | Pro | Gly | Leu | Gly | Lys | Pro | Pro | |
| 330 | | | | | 335 | | | | | 340 | | | | | 345 | |
| GCC | ATA | GAC | CCC | CTC | GTT | AAC | CAA | GCG | GCA | GCT | GGC | TTG | AGG | ACA | CCC | 1108 |
| Ala | Ile | Asp | Pro | Leu | Val | Asn | Gln | Ala | Ala | Ala | Gly | Leu | Arg | Thr | Pro | |
| | | | | 350 | | | | | 355 | | | | | 360 | | |
| CTG | GCA | GTG | CCC | GGC | CCA | TAT | CCT | GCT | CCT | TTT | GGG | ATG | GTC | CCC | CAC | 1156 |
| Leu | Ala | Val | Pro | Gly | Pro | Tyr | Pro | Ala | Pro | Phe | Gly | Met | Val | Pro | His | |
| | | | 365 | | | | 370 | | | | | 375 | | | | |

```
GCT GGC ATG AAC GGC GAG CTG ACC AGC CCA GGC GCT GCC TAC GCC AGT       1204
Ala Gly Met Asn Gly Glu Leu Thr Ser Pro Gly Ala Ala Tyr Ala Ser
        380                 385                 390

TTA CAC AAC ATG TCG CCC CAG ATG AGC GCC GCA GCC GCC CGC GGC CGC       1252
Leu His Asn Met Ser Pro Gln Met Ser Ala Ala Ala Ala Arg Gly Arg
    395                 400                 405

CGT GGT CGG TAC GGG CGC TCC CCC ATG GTG GGG TTT GAT CCT CCC CCT       1300
Arg Gly Arg Tyr Gly Arg Ser Pro Met Val Gly Phe Asp Pro Pro Pro
410                 415                 420                 425

CAC ATG AGA GTA CCT ACC ATT CCT CCA AAC CTG GCA GGA ATC CCT GGG       1348
His Met Arg Val Pro Thr Ile Pro Pro Asn Leu Ala Gly Ile Pro Gly
                430                 435                 440

GGG AAA CCT GCA TAC TCC TTC CAC GTT ACT GCA GAC GGT CAG ATG CAG       1396
Gly Lys Pro Ala Tyr Ser Phe His Val Thr Ala Asp Gly Gln Met Gln
            445                 450                 455

CCT GTC CCT TTT CCC CCG ACG CCC CTC ATC GGA CCC GGA ATC CCC CGG       1444
Pro Val Pro Phe Pro Pro Thr Pro Leu Ile Gly Pro Gly Ile Pro Arg
        460                 465                 470

CAT GCT CGC CAG ATC AAC ACC CTC AAC CAC GGG GAG GTG GTG TGC GCT       1492
His Ala Arg Gln Ile Asn Thr Leu Asn His Gly Glu Val Val Cys Ala
    475                 480                 485

GTG ACC ATC AGC AAC CCC ACG AGA CAC GTG TAC ACA GGC GGG AAG GGC       1540
Val Thr Ile Ser Asn Pro Thr Arg His Val Tyr Thr Gly Gly Lys Gly
490                 495                 500                 505

TGC GTC AAG GTC TGG GAC ATC AGC CAC CCT GGC AAT AAG AGC CCT GTC       1588
Cys Val Lys Val Trp Asp Ile Ser His Pro Gly Asn Lys Ser Pro Val
                510                 515                 520

TCC CAG CTC GAC TGT CTG AAC AGA GAC AAT TAT ATC CGT TCC TGT AAA       1636
Ser Gln Leu Asp Cys Leu Asn Arg Asp Asn Tyr Ile Arg Ser Cys Lys
            525                 530                 535

TTG CTA CCC GAT GGC TGC ACT CTC ATA GTG GGA GGG GAA GCC AGT ACT       1684
Leu Leu Pro Asp Gly Cys Thr Leu Ile Val Gly Gly Glu Ala Ser Thr
        540                 545                 550

TTG TCC ATT TGG GAC CTG GCG GCT CCA ACC CCG CGC ATC AAG GCG GAG       1732
Leu Ser Ile Trp Asp Leu Ala Ala Pro Thr Pro Arg Ile Lys Ala Glu
    555                 560                 565

CTG ACG TCC TCG GCC CCC GCC TGC TAC GCC CTG GCC ATC AGC CCC GAT       1780
Leu Thr Ser Ser Ala Pro Ala Cys Tyr Ala Leu Ala Ile Ser Pro Asp
570                 575                 580                 585

TCC AAG GTC TGC TTC TCA TGC TGC AGC GAC GGC AAC ATC GCT GTG TGG       1828
Ser Lys Val Cys Phe Ser Cys Cys Ser Asp Gly Asn Ile Ala Val Trp
                590                 595                 600

GAT CTG CAC AAC CAG ACA CTA GTG AGG CAA TTC CAG GGC CAC ACA GAC       1876
Asp Leu His Asn Gln Thr Leu Val Arg Gln Phe Gln Gly His Thr Asp
            605                 610                 615

GGA GCC AGC TGT ATT GAC ATT TCT AAT GAT GGC ACC AAG CTC TGG ACG       1924
Gly Ala Ser Cys Ile Asp Ile Ser Asn Asp Gly Thr Lys Leu Trp Thr
        620                 625                 630

GGT GGT TTG GAC AAC ACA GTC AGG TCC TGG GAC CTG CGC GAG GGG CGG       1972
Gly Gly Leu Asp Asn Thr Val Arg Ser Trp Asp Leu Arg Glu Gly Arg
    635                 640                 645

CAG CTG CAG CAG CAC GAC TTC ACC TCC CAG ATC TTC TCC CTG GGG TAC       2020
Gln Leu Gln Gln His Asp Phe Thr Ser Gln Ile Phe Ser Leu Gly Tyr
650                 655                 660                 665

TGC CCC ACC GGG GAG TGG CTG GCA GTG GGC ATG GAG AGC AGC AAT GTG       2068
Cys Pro Thr Gly Glu Trp Leu Ala Val Gly Met Glu Ser Ser Asn Val
                670                 675                 680

GAG GTG CTG CAC GTG AAC AAG CCT GAC AAG TAC CAG CTG CAC CTG CAT       2116
Glu Val Leu His Val Asn Lys Pro Asp Lys Tyr Gln Leu His Leu His
            685                 690                 695
```

| | | | | | | | | | | | | | | | | |
|---|---|---|---|---|---|---|---|---|---|---|---|---|---|---|---|---|
| GAG | AGC | TGC | GTG | CTG | TCC | CTG | AAA | TTT | GCT | TAC | TGT | GGT | AAA | TGG | TTT | 2164 |
| Glu | Ser | Cys | Val | Leu | Ser | Leu | Lys | Phe | Ala | Tyr | Cys | Gly | Lys | Trp | Phe | |
| | | 700 | | | | 705 | | | | | 710 | | | | | |
| GTG | AGT | ACT | GGA | AAA | GAT | AAC | CTC | CTC | AAT | GCT | TGG | CGG | ACC | CCC | TAT | 2212 |
| Val | Ser | Thr | Gly | Lys | Asp | Asn | Leu | Leu | Asn | Ala | Trp | Arg | Thr | Pro | Tyr | |
| | 715 | | | | 720 | | | | | 725 | | | | | | |
| GGA | GCC | AGC | ATA | TTC | CAG | TCC | AAA | GAG | TCC | TCG | TCA | GTG | CTT | AGC | TGT | 2260 |
| Gly | Ala | Ser | Ile | Phe | Gln | Ser | Lys | Glu | Ser | Ser | Ser | Val | Leu | Ser | Cys | |
| 730 | | | | | 735 | | | | 740 | | | | | | 745 | |
| GAC | ATC | TCT | GTG | GAT | GAT | AAG | TAC | ATA | GTC | ACT | GGC | TCG | GGG | GAC | AAG | 2308 |
| Asp | Ile | Ser | Val | Asp | Asp | Lys | Tyr | Ile | Val | Thr | Gly | Ser | Gly | Asp | Lys | |
| | | | | 750 | | | | | 755 | | | | | 760 | | |
| AAG | GCT | ACA | GTC | TAT | GAA | GTC | ATC | TAC | TGAAAACATT | | ATGTGGT | | | | | 2352 |
| Lys | Ala | Thr | Val | Tyr | Glu | Val | Ile | Tyr | | | | | | | | |
| | | | 765 | | | | | 770 | | | | | | | | |

( 2 ) INFORMATION FOR SEQ ID NO:2:

( i ) SEQUENCE CHARACTERISTICS:
        ( A ) LENGTH: 770 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Phe | Pro | Gln | Ser | Arg | His | Pro | Thr | Pro | His | Gln | Ala | Ala | Gly | Gln |
| 1 | | | | 5 | | | | | 10 | | | | | 15 | |
| Pro | Phe | Lys | Phe | Thr | Ile | Pro | Glu | Ser | Leu | Asp | Arg | Ile | Lys | Glu | Glu |
| | | | 20 | | | | 25 | | | | | 30 | | | |
| Phe | Gln | Phe | Leu | Gln | Ala | Gln | Tyr | His | Ser | Leu | Lys | Leu | Glu | Cys | Glu |
| | | | 35 | | | | 40 | | | | 45 | | | | |
| Lys | Leu | Ala | Ser | Glu | Lys | Thr | Glu | Met | Gln | Arg | His | Tyr | Val | Met | Tyr |
| | 50 | | | | 55 | | | | | 60 | | | | | |
| Tyr | Glu | Met | Ser | Tyr | Gly | Leu | Asn | Ile | Glu | Met | His | Lys | Gln | Thr | Glu |
| 65 | | | | | 70 | | | | 75 | | | | | | 80 |
| Ile | Ala | Lys | Arg | Leu | Asn | Thr | Ile | Cys | Ala | Gln | Val | Ile | Pro | Phe | Leu |
| | | | | 85 | | | | | 90 | | | | | 95 | |
| Ser | Gln | Glu | His | Gln | Gln | Gln | Val | Ala | Gln | Ala | Val | Glu | Arg | Ala | Lys |
| | | | | 100 | | | | | 105 | | | | | 110 | |
| Gln | Val | Thr | Met | Ala | Glu | Leu | Asn | Ala | Ile | Ile | Gly | Gln | Gln | Gln | Leu |
| | | | 115 | | | | 120 | | | | | 125 | | | |
| Gln | Ala | Gln | His | Leu | Ser | His | Gly | His | Gly | Pro | Pro | Val | Pro | Leu | Thr |
| | | 130 | | | | 135 | | | | | 140 | | | | |
| Pro | His | Pro | Ser | Gly | Leu | Gln | Pro | Pro | Gly | Ile | Pro | Pro | Leu | Gly | Gly |
| 145 | | | | | 150 | | | | | 155 | | | | | 160 |
| Ser | Ala | Gly | Leu | Leu | Ala | Leu | Ser | Ser | Ala | Leu | Ser | Gly | Gln | Ser | His |
| | | | | 165 | | | | | 170 | | | | | 175 | |
| Leu | Ala | Ile | Lys | Asp | Asp | Lys | Lys | His | His | Asp | Ala | Glu | His | His | Arg |
| | | | 180 | | | | 185 | | | | | 190 | | | |
| Asp | Arg | Glu | Pro | Gly | Thr | Ser | Asn | Ser | Leu | Leu | Val | Pro | Asp | Ser | Leu |
| | | 195 | | | | 200 | | | | | 205 | | | | |
| Arg | Gly | Thr | Asp | Lys | Arg | Arg | Asn | Gly | Pro | Glu | Phe | Ser | Asn | Asp | Ile |
| | 210 | | | | 215 | | | | | 220 | | | | | |
| Lys | Lys | Arg | Lys | Val | Asp | Asp | Lys | Asp | Ser | Ser | His | Tyr | Asp | Ser | Asp |
| 225 | | | | 230 | | | | | 235 | | | | | | 240 |
| Gly | Asp | Lys | Ser | Asp | Asp | Asn | Leu | Val | Val | Asp | Val | Ser | Asn | Glu | Asp |
| | | | | 245 | | | | | 250 | | | | | 255 | |

```
Pro Ser Ser Pro Arg Ala Ser Pro Ala His Ser Pro Arg Glu Asn Gly
        260             265             270
Ile Asp Lys Asn Arg Leu Leu Lys Lys Asp Ala Ser Ser Ser Pro Ala
    275             280             285
Ser Thr Ala Ser Ser Ala Ser Ser Thr Ser Leu Lys Ser Lys Glu Met
290             295             300
Ser Leu His Glu Lys Ala Ser Thr Pro Val Leu Lys Ser Ser Thr Pro
305             310             315             320
Thr Pro Arg Ser Asp Met Pro Thr Pro Gly Thr Ser Ala Thr Pro Gly
            325             330             335
Leu Arg Pro Gly Leu Gly Lys Pro Ala Ile Asp Pro Leu Val Asn
            340             345             350
Gln Ala Ala Ala Gly Leu Arg Thr Pro Leu Ala Val Pro Gly Pro Tyr
        355             360             365
Pro Ala Pro Phe Gly Met Val Pro His Ala Gly Met Asn Gly Glu Leu
    370             375             380
Thr Ser Pro Gly Ala Ala Tyr Ala Ser Leu His Asn Met Ser Pro Gln
385             390             395             400
Met Ser Ala Ala Ala Ala Arg Gly Arg Arg Gly Arg Tyr Gly Arg Ser
            405             410             415
Pro Met Val Gly Phe Asp Pro Pro His Met Arg Val Pro Thr Ile
            420             425             430
Pro Pro Asn Leu Ala Gly Ile Pro Gly Gly Lys Pro Ala Tyr Ser Phe
        435             440             445
His Val Thr Ala Asp Gly Gln Met Gln Pro Val Pro Phe Pro Pro Thr
    450             455             460
Pro Leu Ile Gly Pro Gly Ile Pro Arg His Ala Arg Gln Ile Asn Thr
465             470             475             480
Leu Asn His Gly Glu Val Val Cys Ala Val Thr Ile Ser Asn Pro Thr
            485             490             495
Arg His Val Tyr Thr Gly Gly Lys Gly Cys Val Lys Val Trp Asp Ile
            500             505             510
Ser His Pro Gly Asn Lys Ser Pro Val Ser Gln Leu Asp Cys Leu Asn
        515             520             525
Arg Asp Asn Tyr Ile Arg Ser Cys Lys Leu Leu Pro Asp Gly Cys Thr
    530             535             540
Leu Ile Val Gly Gly Glu Ala Ser Thr Leu Ser Ile Trp Asp Leu Ala
545             550             555             560
Ala Pro Thr Pro Arg Ile Lys Ala Glu Leu Thr Ser Ser Ala Pro Ala
            565             570             575
Cys Tyr Ala Leu Ala Ile Ser Pro Asp Ser Lys Val Cys Phe Ser Cys
            580             585             590
Cys Ser Asp Gly Asn Ile Ala Val Trp Asp Leu His Asn Gln Thr Leu
        595             600             605
Val Arg Gln Phe Gln Gly His Thr Asp Gly Ala Ser Cys Ile Asp Ile
    610             615             620
Ser Asn Asp Gly Thr Lys Leu Trp Thr Gly Gly Leu Asp Asn Thr Val
625             630             635             640
Arg Ser Trp Asp Leu Arg Glu Gly Arg Gln Leu Gln Gln His Asp Phe
            645             650             655
Thr Ser Gln Ile Phe Ser Leu Gly Tyr Cys Pro Thr Gly Glu Trp Leu
            660             665             670
```

| | | | | | | | | | | | | | | |
|---|---|---|---|---|---|---|---|---|---|---|---|---|---|---|
| Ala | Val | Gly | Met | Glu | Ser | Ser | Asn | Val | Glu | Val | Leu | His | Val | Asn | Lys |
| | | 675 | | | | 680 | | | | 685 | | | | | |
| Pro | Asp | Lys | Tyr | Gln | Leu | His | Leu | His | Glu | Ser | Cys | Val | Leu | Ser | Leu |
| | 690 | | | | | 695 | | | | | 700 | | | | |
| Lys | Phe | Ala | Tyr | Cys | Gly | Lys | Trp | Phe | Val | Ser | Thr | Gly | Lys | Asp | Asn |
| 705 | | | | | 710 | | | | | 715 | | | | | 720 |
| Leu | Leu | Asn | Ala | Trp | Arg | Thr | Pro | Tyr | Gly | Ala | Ser | Ile | Phe | Gln | Ser |
| | | | | 725 | | | | | 730 | | | | | 735 | |
| Lys | Glu | Ser | Ser | Ser | Val | Leu | Ser | Cys | Asp | Ile | Ser | Val | Asp | Asp | Lys |
| | | | 740 | | | | | 745 | | | | | 750 | | |
| Tyr | Ile | Val | Thr | Gly | Ser | Gly | Asp | Lys | Lys | Ala | Thr | Val | Tyr | Glu | Val |
| | | | 755 | | | | 760 | | | | | 765 | | | |
| Ile | Tyr | | | | | | | | | | | | | | |
| | 770 | | | | | | | | | | | | | | |

( 2 ) INFORMATION FOR SEQ ID NO:3:

( i ) SEQUENCE CHARACTERISTICS:
        ( A ) LENGTH: 2271 base pairs
        ( B ) TYPE: nucleic acid
        ( C ) STRANDEDNESS: single
        ( D ) TOPOLOGY: unknown ( i i ) MOLECULE TYPE: DNA (cDNA)

( i x ) FEATURE:
        ( A ) NAME/KEY: CDS
        ( B ) LOCATION: 26..2254

( x i ) SEQUENCE DESCRIPTION: SEQ ID NO:3:

| | | | | | | | | | | | | | |
|---|---|---|---|---|---|---|---|---|---|---|---|---|---|
| CTGGGGGGCT | TTTCGAATCG | GCAGG | ATG | TAC | CCC | CAG | GGA | AGG | CAC | CCG | ACC | | 52 |
| | | | Met | Tyr | Pro | Gln | Gly | Arg | His | Pro | Thr | | |
| | | | 1 | | | | 5 | | | | | | |
| CCG | CTC | CAG | TCC | GGC | CAG | CCC | TTC | AAG | TTC | TCG | ATC | TTG | GAG | ATC | TGC | 100 |
| Pro | Leu | Gln | Ser | Gly | Gln | Pro | Phe | Lys | Phe | Ser | Ile | Leu | Glu | Ile | Cys |
| 10 | | | | 15 | | | | | 20 | | | | | 25 | |
| GAC | CGC | ATC | AAA | GAA | GAA | TTC | CAG | TTT | CTT | CAG | GCT | CAA | TAC | CAC | AGC | 148 |
| Asp | Arg | Ile | Lys | Glu | Glu | Phe | Gln | Phe | Leu | Gln | Ala | Gln | Tyr | His | Ser |
| | | | | 30 | | | | | 35 | | | | | 40 | |
| CTC | AAG | CTA | GAA | TGT | GAG | AAG | CTG | GCC | AGC | GAG | AAG | ACG | GAA | ATG | CAG | 196 |
| Leu | Lys | Leu | Glu | Cys | Glu | Lys | Leu | Ala | Ser | Glu | Lys | Thr | Glu | Met | Gln |
| | | | 45 | | | | | 50 | | | | | 55 | | |
| CGA | CAT | TAT | GTC | ATG | TAT | TAT | GAG | ATG | TCG | TAC | GGG | CTC | AAC | ATT | GAA | 244 |
| Arg | His | Tyr | Val | Met | Tyr | Tyr | Glu | Met | Ser | Tyr | Gly | Leu | Asn | Ile | Glu |
| | | 60 | | | | | 65 | | | | | 70 | | | |
| ATG | CAT | AAG | CAG | GCG | GAG | ATT | GTG | AAG | CGT | CTG | AGC | GGT | ATC | TGC | GCT | 292 |
| Met | His | Lys | Gln | Ala | Glu | Ile | Val | Lys | Arg | Leu | Ser | Gly | Ile | Cys | Ala |
| | 75 | | | | | 80 | | | | | 85 | | | | |
| CAG | ATT | ATC | CCC | TTC | CTG | ACC | CAG | GAG | CAT | CAG | CAG | CAG | GTG | CTC | CAG | 340 |
| Gln | Ile | Ile | Pro | Phe | Leu | Thr | Gln | Glu | His | Gln | Gln | Gln | Val | Leu | Gln |
| 90 | | | | | 95 | | | | | 100 | | | | | 105 |
| GCC | GTA | GAA | CGC | GCC | AAG | CAG | GTC | ACC | GTG | GGG | GAG | CTG | AAC | AGC | CTC | 388 |
| Ala | Val | Glu | Arg | Ala | Lys | Gln | Val | Thr | Val | Gly | Glu | Leu | Asn | Ser | Leu |
| | | | | 110 | | | | | 115 | | | | | 120 | |
| ATC | GGG | CAG | CAG | CTC | CAG | CCG | CTG | TCC | CAC | CAC | GCA | CCC | CCT | GTG | CCC | 436 |
| Ile | Gly | Gln | Gln | Leu | Gln | Pro | Leu | Ser | His | His | Ala | Pro | Pro | Val | Pro |
| | | | | 125 | | | | | 130 | | | | | 135 | |
| CTC | ACC | CCC | CGC | CCA | GCC | GGG | CTG | GTG | GGC | GGC | AGT | GCT | ACG | GGG | CTG | 484 |
| Leu | Thr | Pro | Arg | Pro | Ala | Gly | Leu | Val | Gly | Gly | Ser | Ala | Thr | Gly | Leu |
| | | 140 | | | | | 145 | | | | | 150 | | | |

| | | | | | | | | | | | | | | | | |
|---|---|---|---|---|---|---|---|---|---|---|---|---|---|---|---|---|
| CTT | GCT | CTG | TCT | GGA | GCC | CTG | GCT | GCC | CAG | GCT | CAG | CTG | GCG | GCG | GCT | 532 |
| Leu | Ala | Leu | Ser | Gly | Ala | Leu | Ala | Ala | Gln | Ala | Gln | Leu | Ala | Ala | Ala | |
| | 155 | | | | 160 | | | | | 165 | | | | | | |
| GTC | AAG | GAG | GAC | CGT | GCG | GGC | GTG | GAG | GCC | GAG | GGG | TCC | AGA | GTG | GAG | 580 |
| Val | Lys | Glu | Asp | Arg | Ala | Gly | Val | Glu | Ala | Glu | Gly | Ser | Arg | Val | Glu | |
| 170 | | | | | 175 | | | | | 180 | | | | | 185 | |
| AGA | GCC | CCG | AGC | AGG | AGT | GCA | TCT | CCC | TCG | CCC | CCT | GAG | AGT | CTC | GTG | 628 |
| Arg | Ala | Pro | Ser | Arg | Ser | Ala | Ser | Pro | Ser | Pro | Pro | Glu | Ser | Leu | Val | |
| | | | | 190 | | | | | 195 | | | | | 200 | | |
| GAG | GAG | GAG | CGA | CCG | AGT | GGC | CCT | GGT | GGT | GGC | GGG | AAG | CAG | AGA | GCA | 676 |
| Glu | Glu | Glu | Arg | Pro | Ser | Gly | Pro | Gly | Gly | Gly | Gly | Lys | Gln | Arg | Ala | |
| | | | 205 | | | | | 210 | | | | | 215 | | | |
| GAT | GAG | AAG | GAG | CCA | TCA | GGA | CCT | TAT | GAA | AGC | GAC | GAA | GAC | AAG | AGT | 724 |
| Asp | Glu | Lys | Glu | Pro | Ser | Gly | Pro | Tyr | Glu | Ser | Asp | Glu | Asp | Lys | Ser | |
| | | 220 | | | | | 225 | | | | | 230 | | | | |
| GAT | TAC | AAT | CTG | GTG | GTG | GAC | GAG | GAC | CAA | CCC | TCA | GAG | CCC | CCC | AGC | 772 |
| Asp | Tyr | Asn | Leu | Val | Val | Asp | Glu | Asp | Gln | Pro | Ser | Glu | Pro | Pro | Ser | |
| 235 | | | | | 240 | | | | | 245 | | | | | | |
| CCG | GCT | ACC | ACC | CCC | TGC | GGA | AAG | GTA | CCC | ATC | TGC | ATT | CCT | GCC | CGT | 820 |
| Pro | Ala | Thr | Thr | Pro | Cys | Gly | Lys | Val | Pro | Ile | Cys | Ile | Pro | Ala | Arg | |
| 250 | | | | | 255 | | | | | 260 | | | | | 265 | |
| CGG | GAC | CTG | GTG | GAC | AGT | CCA | GCC | TCC | TTG | GCC | TCT | AGC | TTG | CGG | TCA | 868 |
| Arg | Asp | Leu | Val | Asp | Ser | Pro | Ala | Ser | Leu | Ala | Ser | Ser | Leu | Arg | Ser | |
| | | | | 270 | | | | | 275 | | | | | 280 | | |
| CCG | CTG | CCT | AGA | GCC | AAG | GAG | CTC | ATC | CTG | AAT | GAC | CTT | CCC | GCC | AGC | 916 |
| Pro | Leu | Pro | Arg | Ala | Lys | Glu | Leu | Ile | Leu | Asn | Asp | Leu | Pro | Ala | Ser | |
| | | | 285 | | | | | 290 | | | | | 295 | | | |
| ACT | CCT | GCC | TCC | AAA | TCC | TGT | GAC | TCC | TCC | CCG | CCC | CAG | GAC | GCT | TCC | 964 |
| Thr | Pro | Ala | Ser | Lys | Ser | Cys | Asp | Ser | Ser | Pro | Pro | Gln | Asp | Ala | Ser | |
| | | 300 | | | | | 305 | | | | | 310 | | | | |
| ACC | CCC | GGG | CCC | AGC | TCG | GCC | AGT | CAC | CTC | TGC | CAG | CTT | GCG | CTC | AAG | 1012 |
| Thr | Pro | Gly | Pro | Ser | Ser | Ala | Ser | His | Leu | Cys | Gln | Leu | Ala | Leu | Lys | |
| 315 | | | | | 320 | | | | | 325 | | | | | | |
| CCA | GCA | CCT | TCC | ACG | GAC | AGC | GTC | GCC | CTG | AGG | AGC | CCC | CTG | ACT | CTG | 1060 |
| Pro | Ala | Pro | Ser | Thr | Asp | Ser | Val | Ala | Leu | Arg | Ser | Pro | Leu | Thr | Leu | |
| 330 | | | | | 335 | | | | | 340 | | | | | 345 | |
| TCC | AGT | CCC | TTC | ACC | ACG | TCC | TTC | AGC | CTG | GGC | TCC | CAC | AGC | ACT | CTC | 1108 |
| Ser | Ser | Pro | Phe | Thr | Thr | Ser | Phe | Ser | Leu | Gly | Ser | His | Ser | Thr | Leu | |
| | | | | 350 | | | | | 355 | | | | | 360 | | |
| AAC | GGA | GAC | CTC | TCC | GTG | CCC | AGC | TCC | TAC | GTC | AGC | CTC | CAC | CTG | TCC | 1156 |
| Asn | Gly | Asp | Leu | Ser | Val | Pro | Ser | Ser | Tyr | Val | Ser | Leu | His | Leu | Ser | |
| | | | 365 | | | | | 370 | | | | | 375 | | | |
| CCC | CAG | GTC | AGC | AGC | TCT | GTG | GTG | TAC | GGA | CGC | TCC | CCC | GTG | ATG | GCA | 1204 |
| Pro | Gln | Val | Ser | Ser | Ser | Val | Val | Tyr | Gly | Arg | Ser | Pro | Val | Met | Ala | |
| | | 380 | | | | | 385 | | | | | 390 | | | | |
| TTT | GAG | TCT | CAT | CCC | CAT | CTC | CGA | GGG | TCA | TCC | GTC | TCT | TCC | TCC | CTA | 1252 |
| Phe | Glu | Ser | His | Pro | His | Leu | Arg | Gly | Ser | Ser | Val | Ser | Ser | Ser | Leu | |
| 395 | | | | | 400 | | | | | 405 | | | | | | |
| CCC | AGC | ATC | CCT | GGG | GGA | AAG | CCG | GCC | TAC | TCC | TTC | CAC | GTG | TCT | GCG | 1300 |
| Pro | Ser | Ile | Pro | Gly | Gly | Lys | Pro | Ala | Tyr | Ser | Phe | His | Val | Ser | Ala | |
| 410 | | | | | 415 | | | | | 420 | | | | | 425 | |
| GAC | GGG | CAG | ATG | CAG | CCG | GTT | CCC | TTC | CCC | TCG | GAT | GCA | CTG | GTA | GAC | 1348 |
| Asp | Gly | Gln | Met | Gln | Pro | Val | Pro | Phe | Pro | Ser | Asp | Ala | Leu | Val | Asp | |
| | | | | 430 | | | | | 435 | | | | | 440 | | |
| GCG | GGC | ATC | CCG | CGG | CAC | GCC | CGG | CAG | CTG | CAC | ACG | CTG | GCC | CAT | GGC | 1396 |
| Ala | Gly | Ile | Pro | Arg | His | Ala | Arg | Gln | Leu | His | Thr | Leu | Ala | His | Gly | |
| | | | 445 | | | | | 450 | | | | | 455 | | | |
| GAG | GTG | GTC | TGC | GCG | GTC | ACC | ATC | AGC | GGC | TCC | ACA | CAG | CAT | GTG | TAC | 1444 |
| Glu | Val | Val | Cys | Ala | Val | Thr | Ile | Ser | Gly | Ser | Thr | Gln | His | Val | Tyr | |
| | | 460 | | | | | 465 | | | | | 470 | | | | |

|  |  |
|---|---|
| ACG GGC GGC AAG GGC TGT GTG AAG GTG TGG GAC GTG GGC CAG CCT GGG<br>Thr Gly Gly Lys Gly Cys Val Lys Val Trp Asp Val Gly Gln Pro Gly<br>475                          480                    485 | 1492 |
| GCC AAG ACG CCC GTG CGC CAG CTC GAC TGC CTG AAC CGA GAC AAC TAC<br>Ala Lys Thr Pro Val Arg Gln Leu Asp Cys Leu Asn Arg Asp Asn Tyr<br>490                          495                  500                    505 | 1540 |
| ATT CGT TCC TGC AAG TTG CTG CCG GAT GGC CGG AGT CTG ATC GTG GGC<br>Ile Arg Ser Cys Lys Leu Leu Pro Asp Gly Arg Ser Leu Ile Val Gly<br>                      510                      515                    520 | 1588 |
| GGT GAG GCC AGC ACC TTG TCC ATT TGG GAC CTG GCG GCG CCC ACC CCC<br>Gly Glu Ala Ser Thr Leu Ser Ile Trp Asp Leu Ala Ala Pro Thr Pro<br>                525                    530                  535 | 1636 |
| CGT ATC AAG GCC GAG CTG ACT TCC TCA GCC CCA GCC TGC TAC GCC CTG<br>Arg Ile Lys Ala Glu Leu Thr Ser Ser Ala Pro Ala Cys Tyr Ala Leu<br>      540                    545                  550 | 1684 |
| GCC GTC AGC CCC GAC GCC AAG GTT TGC TTC TCC TGC TGC AGC GAT GGC<br>Ala Val Ser Pro Asp Ala Lys Val Cys Phe Ser Cys Cys Ser Asp Gly<br>555                          560                  565 | 1732 |
| AAC ATT GTG GTC TGG GAC CTG CAG AAT CAG ACT ATG GTC AGG CAG TTC<br>Asn Ile Val Val Trp Asp Leu Gln Asn Gln Thr Met Val Arg Gln Phe<br>570                          575                  580                    585 | 1780 |
| CAG GGC CAC ACG GAC GGC GCC AGC TGC ATT GAT ATT TCC GAT TAC GGC<br>Gln Gly His Thr Asp Gly Ala Ser Cys Ile Asp Ile Ser Asp Tyr Gly<br>                      590                    595                  600 | 1828 |
| ACT CGG CTC TGG ACA GGG GGC CTG GAC AAC ACG GTG CGC TGC TGG GAC<br>Thr Arg Leu Trp Thr Gly Gly Leu Asp Asn Thr Val Arg Cys Trp Asp<br>      605                    610                  615 | 1876 |
| CTG CGG GAG GGC CGC CAG CTG CAG CAG CAT GAC TTC AGC TCC CAG ATT<br>Leu Arg Glu Gly Arg Gln Leu Gln Gln His Asp Phe Ser Ser Gln Ile<br>            620                    625                  630 | 1924 |
| TTC TCC CCC TGC CAC TGC CCT AAC CAG GAC TGG CTG GCG GTC GGA ATG<br>Phe Ser Pro Cys His Cys Pro Asn Gln Asp Trp Leu Ala Val Gly Met<br>635                          640                  645 | 1972 |
| GAG AGT AGC AAC GTG GAG ATC CTG CAC GTC GGC AAG CCG GAG AAA TAC<br>Glu Ser Ser Asn Val Glu Ile Leu His Val Gly Lys Pro Glu Lys Tyr<br>650                          655                  660                    665 | 2020 |
| CAG CTG CAC CTC CAC GAG AGC TGC GTG CTG TCC CTG AAG TTT GCC CCT<br>Gln Leu His Leu His Glu Ser Cys Val Leu Ser Leu Lys Phe Ala Pro<br>                      670                    675                  680 | 2068 |
| TGC GGA CGG TGG TTT GTG AGC ACC GGG AAG GAC AAC CTG CTC AAC GCC<br>Cys Gly Arg Trp Phe Val Ser Thr Gly Lys Asp Asn Leu Leu Asn Ala<br>            685                    690                  695 | 2116 |
| TGG AGG ACG CCG TAC GGG GCC AGC ATT TTC CAG TCC AAG GAG TCG TCC<br>Trp Arg Thr Pro Tyr Gly Ala Ser Ile Phe Gln Ser Lys Glu Ser Ser<br>700                          705                  710 | 2164 |
| TCA GTC CTG AGT TGT GAC ATC TCC AGA AAT AAC AAA TAC ATT GTG ACA<br>Ser Val Leu Ser Cys Asp Ile Ser Arg Asn Asn Lys Tyr Ile Val Thr<br>715                          720                  725 | 2212 |
| GGC TCG GGG GAC AAG AAG GCC ACC GTG TAT GAG GTG GTC TAC<br>Gly Ser Gly Asp Lys Lys Ala Thr Val Tyr Glu Val Val Tyr<br>730                          735                  740 | 2254 |
| TGAAGACATG ACCCCCC | 2271 |

( 2 ) INFORMATION FOR SEQ ID NO:4:

( i ) SEQUENCE CHARACTERISTICS:
        ( A ) LENGTH: 743 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:4:

| Met | Tyr | Pro | Gln | Gly | Arg | His | Pro | Thr | Pro | Leu | Gln | Ser | Gly | Gln | Pro |
|---|---|---|---|---|---|---|---|---|---|---|---|---|---|---|---|
| 1 | | | | 5 | | | | | 10 | | | | | 15 | |

| Phe | Lys | Phe | Ser | Ile | Leu | Glu | Ile | Cys | Asp | Arg | Ile | Lys | Glu | Phe |
|---|---|---|---|---|---|---|---|---|---|---|---|---|---|---|
| | | | 20 | | | | | 25 | | | | | 30 | |

| Gln | Phe | Leu | Gln | Ala | Gln | Tyr | His | Ser | Leu | Lys | Leu | Glu | Cys | Glu | Lys |
|---|---|---|---|---|---|---|---|---|---|---|---|---|---|---|---|
| | | | 35 | | | | | 40 | | | | | 45 | | |

| Leu | Ala | Ser | Glu | Lys | Thr | Glu | Met | Gln | Arg | His | Tyr | Val | Met | Tyr | Tyr |
|---|---|---|---|---|---|---|---|---|---|---|---|---|---|---|---|
| | 50 | | | | | 55 | | | | | 60 | | | | |

| Glu | Met | Ser | Tyr | Gly | Leu | Asn | Ile | Glu | Met | His | Lys | Gln | Ala | Glu | Ile |
|---|---|---|---|---|---|---|---|---|---|---|---|---|---|---|---|
| 65 | | | | | 70 | | | | | 75 | | | | | 80 |

| Val | Lys | Arg | Leu | Ser | Gly | Ile | Cys | Ala | Gln | Ile | Ile | Pro | Phe | Leu | Thr |
|---|---|---|---|---|---|---|---|---|---|---|---|---|---|---|---|
| | | | | 85 | | | | | 90 | | | | | 95 | |

| Gln | Glu | His | Gln | Gln | Gln | Val | Leu | Gln | Ala | Val | Glu | Arg | Ala | Lys | Gln |
|---|---|---|---|---|---|---|---|---|---|---|---|---|---|---|---|
| | | | 100 | | | | | 105 | | | | | 110 | | |

| Val | Thr | Val | Gly | Glu | Leu | Asn | Ser | Leu | Ile | Gly | Gln | Gln | Leu | Gln | Pro |
|---|---|---|---|---|---|---|---|---|---|---|---|---|---|---|---|
| | | 115 | | | | | 120 | | | | | 125 | | | |

| Leu | Ser | His | His | Ala | Pro | Pro | Val | Pro | Leu | Thr | Pro | Arg | Pro | Ala | Gly |
|---|---|---|---|---|---|---|---|---|---|---|---|---|---|---|---|
| | 130 | | | | | 135 | | | | | 140 | | | | |

| Leu | Val | Gly | Gly | Ser | Ala | Thr | Gly | Leu | Leu | Ala | Leu | Ser | Gly | Ala | Leu |
|---|---|---|---|---|---|---|---|---|---|---|---|---|---|---|---|
| 145 | | | | | 150 | | | | | 155 | | | | | 160 |

| Ala | Ala | Gln | Ala | Gln | Leu | Ala | Ala | Ala | Val | Lys | Glu | Asp | Arg | Ala | Gly |
|---|---|---|---|---|---|---|---|---|---|---|---|---|---|---|---|
| | | | | 165 | | | | | 170 | | | | | 175 | |

| Val | Glu | Ala | Glu | Gly | Ser | Arg | Val | Glu | Arg | Ala | Pro | Ser | Arg | Ser | Ala |
|---|---|---|---|---|---|---|---|---|---|---|---|---|---|---|---|
| | | | 180 | | | | | 185 | | | | | 190 | | |

| Ser | Pro | Ser | Pro | Pro | Glu | Ser | Leu | Val | Glu | Glu | Glu | Arg | Pro | Ser | Gly |
|---|---|---|---|---|---|---|---|---|---|---|---|---|---|---|---|
| | | 195 | | | | | 200 | | | | | 205 | | | |

| Pro | Gly | Gly | Gly | Gly | Lys | Gln | Arg | Ala | Asp | Glu | Lys | Glu | Pro | Ser | Gly |
|---|---|---|---|---|---|---|---|---|---|---|---|---|---|---|---|
| | 210 | | | | | 215 | | | | | 220 | | | | |

| Pro | Tyr | Glu | Ser | Asp | Glu | Asp | Lys | Ser | Asp | Tyr | Asn | Leu | Val | Val | Asp |
|---|---|---|---|---|---|---|---|---|---|---|---|---|---|---|---|
| 225 | | | | | 230 | | | | | 235 | | | | | 240 |

| Glu | Asp | Gln | Pro | Ser | Glu | Pro | Pro | Ser | Pro | Ala | Thr | Thr | Pro | Cys | Gly |
|---|---|---|---|---|---|---|---|---|---|---|---|---|---|---|---|
| | | | | 245 | | | | | 250 | | | | | 255 | |

| Lys | Val | Pro | Ile | Cys | Ile | Pro | Ala | Arg | Arg | Asp | Leu | Val | Asp | Ser | Pro |
|---|---|---|---|---|---|---|---|---|---|---|---|---|---|---|---|
| | | | 260 | | | | | 265 | | | | | 270 | | |

| Ala | Ser | Leu | Ala | Ser | Ser | Leu | Arg | Ser | Pro | Leu | Pro | Arg | Ala | Lys | Glu |
|---|---|---|---|---|---|---|---|---|---|---|---|---|---|---|---|
| | | 275 | | | | | 280 | | | | | 285 | | | |

| Leu | Ile | Leu | Asn | Asp | Leu | Pro | Ala | Ser | Thr | Pro | Ala | Ser | Lys | Ser | Cys |
|---|---|---|---|---|---|---|---|---|---|---|---|---|---|---|---|
| | 290 | | | | | 295 | | | | | 300 | | | | |

| Asp | Ser | Ser | Pro | Pro | Gln | Asp | Ala | Ser | Thr | Pro | Gly | Pro | Ser | Ser | Ala |
|---|---|---|---|---|---|---|---|---|---|---|---|---|---|---|---|
| 305 | | | | | 310 | | | | | 315 | | | | | 320 |

| Ser | His | Leu | Cys | Gln | Leu | Ala | Leu | Lys | Pro | Ala | Pro | Ser | Thr | Asp | Ser |
|---|---|---|---|---|---|---|---|---|---|---|---|---|---|---|---|
| | | | | 325 | | | | | 330 | | | | | 335 | |

| Val | Ala | Leu | Arg | Ser | Pro | Leu | Thr | Leu | Ser | Ser | Pro | Phe | Thr | Thr | Ser |
|---|---|---|---|---|---|---|---|---|---|---|---|---|---|---|---|
| | | | 340 | | | | | 345 | | | | | 350 | | |

| Phe | Ser | Leu | Gly | Ser | His | Ser | Thr | Leu | Asn | Gly | Asp | Leu | Ser | Val | Pro |
|---|---|---|---|---|---|---|---|---|---|---|---|---|---|---|---|
| | | 355 | | | | | 360 | | | | | 365 | | | |

| Ser | Ser | Tyr | Val | Ser | Leu | His | Leu | Ser | Pro | Gln | Val | Ser | Ser | Ser | Val |
|---|---|---|---|---|---|---|---|---|---|---|---|---|---|---|---|
| | 370 | | | | | 375 | | | | | 380 | | | | |

| Val | Tyr | Gly | Arg | Ser | Pro | Val | Met | Ala | Phe | Glu | Ser | His | Pro | His | Leu |
|---|---|---|---|---|---|---|---|---|---|---|---|---|---|---|---|
| 385 | | | | | 390 | | | | | 395 | | | | | 400 |

| | | | | | | | | | | | | | |
|---|---|---|---|---|---|---|---|---|---|---|---|---|---|
| Arg | Gly | Ser | Ser | Val<br>405 | Ser | Ser | Ser | Leu | Pro<br>410 | Ser | Ile | Pro | Gly | Gly<br>415 | Lys |
| Pro | Ala | Tyr | Ser<br>420 | Phe | His | Val | Ser | Ala<br>425 | Asp | Gly | Gln | Met | Gln<br>430 | Pro | Val |
| Pro | Phe | Pro<br>435 | Ser | Asp | Ala | Leu | Val<br>440 | Asp | Ala | Gly | Ile | Pro<br>445 | Arg | His | Ala |
| Arg | Gln<br>450 | Leu | His | Thr | Leu | Ala<br>455 | His | Gly | Glu | Val | Val<br>460 | Cys | Ala | Val | Thr |
| Ile<br>465 | Ser | Gly | Ser | Thr | Gln<br>470 | His | Val | Tyr | Thr | Gly<br>475 | Gly | Lys | Gly | Cys | Val<br>480 |
| Lys | Val | Trp | Asp | Val<br>485 | Gly | Gln | Pro | Gly | Ala<br>490 | Lys | Thr | Pro | Val | Arg<br>495 | Gln |
| Leu | Asp | Cys | Leu<br>500 | Asn | Arg | Asp | Asn | Tyr<br>505 | Ile | Arg | Ser | Cys | Lys<br>510 | Leu | Leu |
| Pro | Asp | Gly<br>515 | Arg | Ser | Leu | Ile | Val<br>520 | Gly | Gly | Glu | Ala | Ser<br>525 | Thr | Leu | Ser |
| Ile | Trp<br>530 | Asp | Leu | Ala | Ala | Pro<br>535 | Thr | Pro | Arg | Ile | Lys<br>540 | Ala | Glu | Leu | Thr |
| Ser<br>545 | Ser | Ala | Pro | Ala | Cys<br>550 | Tyr | Ala | Leu | Ala | Val<br>555 | Ser | Pro | Asp | Ala | Lys<br>560 |
| Val | Cys | Phe | Ser | Cys<br>565 | Cys | Ser | Asp | Gly | Asn<br>570 | Ile | Val | Val | Trp | Asp<br>575 | Leu |
| Gln | Asn | Gln | Thr<br>580 | Met | Val | Arg | Gln | Phe<br>585 | Gln | Gly | His | Thr | Asp<br>590 | Gly | Ala |
| Ser | Cys | Ile<br>595 | Asp | Ile | Ser | Asp | Tyr<br>600 | Gly | Thr | Arg | Leu | Trp<br>605 | Thr | Gly | Gly |
| Leu | Asp<br>610 | Asn | Thr | Val | Arg | Cys<br>615 | Trp | Asp | Leu | Arg | Glu<br>620 | Gly | Arg | Gln | Leu |
| Gln<br>625 | Gln | His | Asp | Phe | Ser<br>630 | Ser | Gln | Ile | Phe | Ser<br>635 | Pro | Cys | His | Cys | Pro<br>640 |
| Asn | Gln | Asp | Trp | Leu<br>645 | Ala | Val | Gly | Met | Glu<br>650 | Ser | Ser | Asn | Val | Glu<br>655 | Ile |
| Leu | His | Val | Gly<br>660 | Lys | Pro | Glu | Lys | Tyr<br>665 | Gln | Leu | His | Leu | His<br>670 | Glu | Ser |
| Cys | Val | Leu<br>675 | Ser | Leu | Lys | Phe | Ala<br>680 | Pro | Cys | Gly | Arg | Trp<br>685 | Phe | Val | Ser |
| Thr | Gly<br>690 | Lys | Asp | Asn | Leu | Leu<br>695 | Asn | Ala | Trp | Arg | Thr<br>700 | Pro | Tyr | Gly | Ala |
| Ser<br>705 | Ile | Phe | Gln | Ser | Lys<br>710 | Glu | Ser | Ser | Ser | Val<br>715 | Leu | Ser | Cys | Asp | Ile<br>720 |
| Ser | Arg | Asn | Asn | Lys<br>725 | Tyr | Ile | Val | Thr | Gly<br>730 | Ser | Gly | Asp | Lys | Lys<br>735 | Ala |
| Thr | Val | Tyr | Glu | Val<br>740 | Val | Tyr | | | | | | | | | |

( 2 ) INFORMATION FOR SEQ ID NO:5:

( i ) SEQUENCE CHARACTERISTICS:
        ( A ) LENGTH: 2357 base pairs
        ( B ) TYPE: nucleic acid
        ( C ) STRANDEDNESS: single
        ( D ) TOPOLOGY: unknown ( i i ) MOLECULE TYPE: DNA (cDNA)

( i x ) FEATURE:
    ( A ) NAME/KEY: CDS
    ( B ) LOCATION: 22..2337

( x i ) SEQUENCE DESCRIPTION: SEQ ID NO:5:

```
GAATCACGAC CCCTCCCTGC C ATG TAT CCG CAG GGC AGA CAT CCG GCT CCC        51
                         Met Tyr Pro Gln Gly Arg His Pro Ala Pro
                          1           5                       10

CAT CAA CCC GGG CAG CCG GGA TTT AAA TTC ACG GTG GCT GAG TCT TGT        99
His Gln Pro Gly Gln Pro Gly Phe Lys Phe Thr Val Ala Glu Ser Cys
            15                  20                  25

GAC AGG ATC AAA GAC GAA TTC CAG TTC CTG CAA GCT CAG TAT CAC AGC       147
Asp Arg Ile Lys Asp Glu Phe Gln Phe Leu Gln Ala Gln Tyr His Ser
                30                  35                  40

CTC AAA GTG GAG TAC GAC AAG CTG GCA AAC GAG AAG ACG GAG ATG CAG       195
Leu Lys Val Glu Tyr Asp Lys Leu Ala Asn Glu Lys Thr Glu Met Gln
            45                  50                  55

CGC CAT TAT GTG ATG TAC TAT GAG ATG TCC TAT GGC TTG AAC ATT GAA       243
Arg His Tyr Val Met Tyr Tyr Glu Met Ser Tyr Gly Leu Asn Ile Glu
        60                  65                  70

ATG CAC AAG CAG ACA GAG ATT GCG AAG AGA CTG AAC ACA ATT TTA GCA       291
Met His Lys Gln Thr Glu Ile Ala Lys Arg Leu Asn Thr Ile Leu Ala
 75                  80                  85                  90

CAG ATC ATG CCT TTC CTG TCA CAA GAG CAC CAG CAG CAG GTG GCG CAG       339
Gln Ile Met Pro Phe Leu Ser Gln Glu His Gln Gln Gln Val Ala Gln
                 95                 100                 105

GCA GTG GAG CGC GCC AAG CAG GTC ACC ATG ACG GAG CTG AAC GCC ATC       387
Ala Val Glu Arg Ala Lys Gln Val Thr Met Thr Glu Leu Asn Ala Ile
            110                 115                 120

ATC GGG CAG CAG CAG CTC CAG GCG CAG CAC CTC TCC CAT GCC ACA CAC       435
Ile Gly Gln Gln Gln Leu Gln Ala Gln His Leu Ser His Ala Thr His
                125                 130                 135

GGC CCC CCG GTC CAG TTG CCA CCC CAC CCG TCA GGT CTC CAG CCT CCA       483
Gly Pro Pro Val Gln Leu Pro Pro His Pro Ser Gly Leu Gln Pro Pro
            140                 145                 150

GGA ATC CCC CCA GTG ACA GGG AGC AGC TCC GGG CTG CTG GCA CTG GGC       531
Gly Ile Pro Pro Val Thr Gly Ser Ser Ser Gly Leu Leu Ala Leu Gly
155                 160                 165                 170

GCC CTG GGC AGC CAG GCC CAT CTG ACG GTG AAG GAT GAG AAG AAC CAC       579
Ala Leu Gly Ser Gln Ala His Leu Thr Val Lys Asp Glu Lys Asn His
                175                 180                 185

CAT GAA CTC GAT CAC AGA GAG AGA GAA TCC AGT GCG AAT AAC TCT GTG       627
His Glu Leu Asp His Arg Glu Arg Glu Ser Ser Ala Asn Asn Ser Val
            190                 195                 200

TCA CCC TCG GAA AGC CTC CGG GCC AGT GAG AAG CAC CGG GGC TCT GCG       675
Ser Pro Ser Glu Ser Leu Arg Ala Ser Glu Lys His Arg Gly Ser Ala
                205                 210                 215

GAC TAC AGC ATG GAA GCC AAG AAG CGG AAG GTG GAG GAG AAG GAC AGC       723
Asp Tyr Ser Met Glu Ala Lys Lys Arg Lys Val Glu Glu Lys Asp Ser
            220                 225                 230

TTG AGC CGA TAC GAC AGT GAT GGA GAC AAG AGT GAT GAT CTG GTG GTG       771
Leu Ser Arg Tyr Asp Ser Asp Gly Asp Lys Ser Asp Asp Leu Val Val
235                 240                 245                 250

GAT GTT TCC AAT GAG GAC CCC GCA ACG CCC CGG GTC AGC CCG GCA CAC       819
Asp Val Ser Asn Glu Asp Pro Ala Thr Pro Arg Val Ser Pro Ala His
                255                 260                 265

TCC CCT CCT GAA AAT GGG CTG GAC AAG GCC CGT AGC CTG AAA AAA GAT       867
Ser Pro Pro Glu Asn Gly Leu Asp Lys Ala Arg Ser Leu Lys Lys Asp
            270                 275                 280
```

| | | | | | | | | | | | | | | | | |
|---|---|---|---|---|---|---|---|---|---|---|---|---|---|---|---|---|
| GCC | CCC | ACC | AGC | CCT | GCC | TCG | GTG | GCC | TCT | TCC | AGT | AGC | ACA | CCT | TCC | 915 |
| Ala | Pro | Thr | Ser | Pro | Ala | Ser | Val | Ala | Ser | Ser | Ser | Ser | Thr | Pro | Ser | |
| | | 285 | | | | | 290 | | | | | 295 | | | | |
| TCC | AAG | ACC | AAA | GAC | CTT | GGT | CAT | AAC | GAC | AAA | TCC | TCC | ACC | CCT | GGG | 963 |
| Ser | Lys | Thr | Lys | Asp | Leu | Gly | His | Asn | Asp | Lys | Ser | Ser | Thr | Pro | Gly | |
| | 300 | | | | 305 | | | | | 310 | | | | | | |
| CTC | AAG | TCC | AAC | ACA | CCA | ACC | CCA | AGG | AAC | GAC | GCC | CCA | ACT | CCA | GGC | 1011 |
| Leu | Lys | Ser | Asn | Thr | Pro | Thr | Pro | Arg | Asn | Asp | Ala | Pro | Thr | Pro | Gly | |
| 315 | | | | 320 | | | | | 325 | | | | | 330 | | |
| ACC | AGC | ACG | ACC | CCA | GGG | CTC | AGG | TCG | ATG | CCG | GGT | AAA | CCT | CCG | GGC | 1059 |
| Thr | Ser | Thr | Thr | Pro | Gly | Leu | Arg | Ser | Met | Pro | Gly | Lys | Pro | Pro | Gly | |
| | | | 335 | | | | 340 | | | | | 345 | | | | |
| ATG | GAC | CCG | ATA | GGT | ATA | ATG | GCC | TCG | GCT | CTG | CGC | ACG | CCC | ATC | TCC | 1107 |
| Met | Asp | Pro | Ile | Gly | Ile | Met | Ala | Ser | Ala | Leu | Arg | Thr | Pro | Ile | Ser | |
| | | 350 | | | | 355 | | | | | 360 | | | | | |
| ATC | ACC | AGC | TCC | TAT | GCG | GCG | CCC | TTC | GCC | ATG | ATG | AGC | CAC | CAT | GAG | 1155 |
| Ile | Thr | Ser | Ser | Tyr | Ala | Ala | Pro | Phe | Ala | Met | Met | Ser | His | His | Glu | |
| | | 365 | | | | 370 | | | | | 375 | | | | | |
| ATG | AAC | GGC | TCC | CTC | ACC | AGT | CCT | GGC | GCC | TAC | GCC | GGC | CTC | CAC | AAC | 1203 |
| Met | Asn | Gly | Ser | Leu | Thr | Ser | Pro | Gly | Ala | Tyr | Ala | Gly | Leu | His | Asn | |
| | 380 | | | | 385 | | | | | 390 | | | | | | |
| ATC | CCA | CCC | CAG | ATG | AGC | GCC | GCC | GCC | GCT | GCT | GCA | GCC | GCT | GCC | TAT | 1251 |
| Ile | Pro | Pro | Gln | Met | Ser | Ala | Ala | Ala | Ala | Ala | Ala | Ala | Ala | Ala | Tyr | |
| 395 | | | | 400 | | | | | 405 | | | | | 410 | | |
| GGC | CGA | TCG | CCA | ATG | GTG | AGC | TTT | GGA | GCT | GTT | GGT | TTT | GAC | CCT | CAC | 1299 |
| Gly | Arg | Ser | Pro | Met | Val | Ser | Phe | Gly | Ala | Val | Gly | Phe | Asp | Pro | His | |
| | | | | 415 | | | | 420 | | | | | 425 | | | |
| CCC | CCG | ATG | CGG | GCC | ACA | GGC | CTC | CCC | TCA | AGC | CTG | GCC | TCC | ATT | CCT | 1347 |
| Pro | Pro | Met | Arg | Ala | Thr | Gly | Leu | Pro | Ser | Ser | Leu | Ala | Ser | Ile | Pro | |
| | | 430 | | | | 435 | | | | | 440 | | | | | |
| GGA | GGA | AAA | CCA | GCG | TAC | TCA | TTC | CAT | GTG | AGT | GCT | GAT | GGG | CAG | ATG | 1395 |
| Gly | Gly | Lys | Pro | Ala | Tyr | Ser | Phe | His | Val | Ser | Ala | Asp | Gly | Gln | Met | |
| | 445 | | | | 450 | | | | | 455 | | | | | | |
| CAG | CCC | GTG | CCC | TTC | CCC | CAC | GAC | GCC | CTG | GCA | GGC | CCC | GGC | ATC | CCG | 1443 |
| Gln | Pro | Val | Pro | Phe | Pro | His | Asp | Ala | Leu | Ala | Gly | Pro | Gly | Ile | Pro | |
| 460 | | | | 465 | | | | | 470 | | | | | | | |
| AGG | CAC | GCC | CGG | CAG | ATC | AAC | ACA | CTC | AGC | CAC | GGG | GGG | GTG | GTG | TGT | 1491 |
| Arg | His | Ala | Arg | Gln | Ile | Asn | Thr | Leu | Ser | His | Gly | Gly | Val | Val | Cys | |
| 475 | | | | 480 | | | | | 485 | | | | | 490 | | |
| GCC | GTG | ACC | ATC | AGC | AAC | CCC | AGC | AGG | CAC | GTC | TAC | ACA | GGT | GGC | AAG | 1539 |
| Ala | Val | Thr | Ile | Ser | Asn | Pro | Ser | Arg | His | Val | Tyr | Thr | Gly | Gly | Lys | |
| | | | | 495 | | | | 500 | | | | | 505 | | | |
| GGC | TGC | GTG | AAG | ATC | TGG | GAC | ATC | AGC | CAG | CCA | GGC | AGC | AAG | AGC | CCC | 1587 |
| Gly | Cys | Val | Lys | Ile | Trp | Asp | Ile | Ser | Gln | Pro | Gly | Ser | Lys | Ser | Pro | |
| | | | 510 | | | | | 515 | | | | | 520 | | | |
| ATC | TCC | CAG | CTG | GAC | TGC | CTG | AAC | AGG | GAC | AAT | TAC | ATG | CGC | TCC | TGC | 1635 |
| Ile | Ser | Gln | Leu | Asp | Cys | Leu | Asn | Arg | Asp | Asn | Tyr | Met | Arg | Ser | Cys | |
| | 525 | | | | 530 | | | | | 535 | | | | | | |
| AAG | CTG | CAC | CCT | GAT | GGG | CGC | ACG | CTC | ATC | GTG | GGC | GGC | GAG | GGC | AGC | 1683 |
| Lys | Leu | His | Pro | Asp | Gly | Arg | Thr | Leu | Ile | Val | Gly | Gly | Glu | Gly | Ser | |
| 540 | | | | 545 | | | | | 550 | | | | | | | |
| ACG | CTC | ACC | ATC | TGG | GAC | CTG | GCC | TCG | CCC | ACG | CCC | CGC | ATC | AAG | GCC | 1731 |
| Thr | Leu | Thr | Ile | Trp | Asp | Leu | Ala | Ser | Pro | Thr | Pro | Arg | Ile | Lys | Ala | |
| 555 | | | | 560 | | | | | 565 | | | | | 570 | | |
| GAG | CTG | ACG | TCC | TCG | GCT | CCC | GCC | TGT | TAT | GCC | CTG | GCC | ATT | AGC | CCT | 1779 |
| Glu | Leu | Thr | Ser | Ser | Ala | Pro | Ala | Cys | Tyr | Ala | Leu | Ala | Ile | Ser | Pro | |
| | | | | 575 | | | | 580 | | | | | 585 | | | |
| GAC | GCC | AAA | GTC | TGC | TTC | TCC | TGC | TGC | AGC | GAT | GGG | AAC | ATT | GCT | GTC | 1827 |
| Asp | Ala | Lys | Val | Cys | Phe | Ser | Cys | Cys | Ser | Asp | Gly | Asn | Ile | Ala | Val | |
| | | 590 | | | | 595 | | | | | 600 | | | | | |

| | | | | | | | | | | | | | | | | |
|---|---|---|---|---|---|---|---|---|---|---|---|---|---|---|---|---|
| TGG | GAC | CTG | CAC | AAC | CAG | ACC | CTG | GTC | AGG | CAG | TTC | CAG | GGC | CAC | ACA | 1875 |
| Trp | Asp | Leu | His | Asn | Gln | Thr | Leu | Val | Arg | Gln | Phe | Gln | Gly | His | Thr | |
| | | 605 | | | | | 610 | | | | | 615 | | | | |
| GAT | GGG | GCC | AGC | TGC | ATA | GAC | ATC | TCC | CAT | GAT | GGC | ACC | AAA | CTG | TGG | 1923 |
| Asp | Gly | Ala | Ser | Cys | Ile | Asp | Ile | Ser | His | Asp | Gly | Thr | Lys | Leu | Trp | |
| | 620 | | | | | 625 | | | | | 630 | | | | | |
| ACA | GGG | GGC | CTG | GAC | AAC | ACG | GTG | CGC | TCC | TGG | GAC | CTG | CGG | GAG | GGC | 1971 |
| Thr | Gly | Gly | Leu | Asp | Asn | Thr | Val | Arg | Ser | Trp | Asp | Leu | Arg | Glu | Gly | |
| 635 | | | | | 640 | | | | | 645 | | | | | 650 | |
| CGA | CAG | CTA | CAG | CAG | CAT | GAC | TTC | ACT | TCC | CAG | ATC | TTC | TCG | CTG | GGC | 2019 |
| Arg | Gln | Leu | Gln | Gln | His | Asp | Phe | Thr | Ser | Gln | Ile | Phe | Ser | Leu | Gly | |
| | | | | 655 | | | | | 660 | | | | | 665 | | |
| TAC | TGC | CCC | ACT | GGG | GAG | TGG | CTG | GCT | GTG | GGC | ATG | GAG | AGC | AGC | AAC | 2067 |
| Tyr | Cys | Pro | Thr | Gly | Glu | Trp | Leu | Ala | Val | Gly | Met | Glu | Ser | Ser | Asn | |
| | | | 670 | | | | | 675 | | | | | 680 | | | |
| GTG | GAG | GTG | CTG | CAC | CAC | ACC | AAG | CCT | CAC | AAG | TAC | CAG | CTG | CAC | CTG | 2115 |
| Val | Glu | Val | Leu | His | His | Thr | Lys | Pro | His | Lys | Tyr | Gln | Leu | His | Leu | |
| | | 685 | | | | | 690 | | | | | 695 | | | | |
| CAC | GAG | AGC | TGC | GTG | CTC | TCC | CTC | AAG | TTC | GCC | TAC | TGC | GGC | AAG | TGG | 2163 |
| His | Glu | Ser | Cys | Val | Leu | Ser | Leu | Lys | Phe | Ala | Tyr | Cys | Gly | Lys | Trp | |
| | 700 | | | | | 705 | | | | | 710 | | | | | |
| TTC | GTG | AGC | ACT | GGG | AAA | GAT | AAC | CTT | CTC | AAC | GCC | TGG | AGG | ACG | CCT | 2211 |
| Phe | Val | Ser | Thr | Gly | Lys | Asp | Asn | Leu | Leu | Asn | Ala | Trp | Arg | Thr | Pro | |
| 715 | | | | | 720 | | | | | 725 | | | | | 730 | |
| TAT | GGA | GCC | AGC | ATA | TCC | CAG | TCT | AAA | GAA | TCC | TCG | TCT | GTC | TTG | AGT | 2259 |
| Tyr | Gly | Ala | Ser | Ile | Ser | Gln | Ser | Lys | Glu | Ser | Ser | Ser | Val | Leu | Ser | |
| | | | | 735 | | | | | 740 | | | | | 745 | | |
| TGT | GAC | ATT | TCA | GCG | GAT | GAC | AAA | TAC | ATT | GTA | ACA | GGC | TCT | GGT | GAC | 2307 |
| Cys | Asp | Ile | Ser | Ala | Asp | Asp | Lys | Tyr | Ile | Val | Thr | Gly | Ser | Gly | Asp | |
| | | | 750 | | | | | 755 | | | | | 760 | | | |
| AAG | AAG | GCC | ACA | GTT | TAT | GAG | GTC | ATC | TAC | TAAACAAGAA | | CTCCAGCAGG | | | | 2357 |
| Lys | Lys | Ala | Thr | Val | Tyr | Glu | Val | Ile | Tyr | | | | | | | |
| | | 765 | | | | 770 | | | | | | | | | | |

(2) INFORMATION FOR SEQ ID NO:6:

(i) SEQUENCE CHARACTERISTICS:
        (A) LENGTH: 772 amino acids
        (B) TYPE: amino acid
        (D) TOPOLOGY: unknown (ii) MOLECULE TYPE: protein (xi) SEQUENCE DESCRIPTION: SEQ ID NO:6:

| | | | | | | | | | | | | | | |
|---|---|---|---|---|---|---|---|---|---|---|---|---|---|---|
| Met | Tyr | Pro | Gln | Gly | Arg | His | Pro | Ala | Pro | His | Gln | Pro | Gly | Gln | Pro |
| 1 | | | | 5 | | | | | 10 | | | | | 15 | |
| Gly | Phe | Lys | Phe | Thr | Val | Ala | Glu | Ser | Cys | Asp | Arg | Ile | Lys | Asp | Glu |
| | | | 20 | | | | | 25 | | | | | 30 | | |
| Phe | Gln | Phe | Leu | Gln | Ala | Gln | Tyr | His | Ser | Leu | Lys | Val | Glu | Tyr | Asp |
| | | 35 | | | | | 40 | | | | | 45 | | | |
| Lys | Leu | Ala | Asn | Glu | Lys | Thr | Glu | Met | Gln | Arg | His | Tyr | Val | Met | Tyr |
| | 50 | | | | | 55 | | | | | 60 | | | | |
| Tyr | Glu | Met | Ser | Tyr | Gly | Leu | Asn | Ile | Glu | Met | His | Lys | Gln | Thr | Glu |
| 65 | | | | | 70 | | | | | 75 | | | | | 80 |
| Ile | Ala | Lys | Arg | Leu | Asn | Thr | Ile | Leu | Ala | Gln | Ile | Met | Pro | Phe | Leu |
| | | | | 85 | | | | | 90 | | | | | 95 | |
| Ser | Gln | Glu | His | Gln | Gln | Gln | Val | Ala | Gln | Ala | Val | Glu | Arg | Ala | Lys |
| | | | 100 | | | | | 105 | | | | | 110 | | |
| Gln | Val | Thr | Met | Thr | Glu | Leu | Asn | Ala | Ile | Ile | Gly | Gln | Gln | Gln | Leu |
| | | | 115 | | | | | 120 | | | | | 125 | | |

| | | | | | | | | | | | | | |
|---|---|---|---|---|---|---|---|---|---|---|---|---|---|
| Gln | Ala | Gln | His | Leu | Ser | His | Ala | Thr | His | Gly | Pro | Pro | Val | Gln | Leu |
| | 130 | | | | 135 | | | | | 140 | | | |
| Pro | Pro | His | Pro | Ser | Gly | Leu | Gln | Pro | Pro | Gly | Ile | Pro | Pro | Val | Thr |
| 145 | | | | | 150 | | | | | 155 | | | | | 160 |
| Gly | Ser | Ser | Ser | Gly | Leu | Leu | Ala | Leu | Gly | Ala | Leu | Gly | Ser | Gln | Ala |
| | | | | 165 | | | | | 170 | | | | | 175 |
| His | Leu | Thr | Val | Lys | Asp | Glu | Lys | Asn | His | His | Glu | Leu | Asp | His | Arg |
| | | | 180 | | | | | 185 | | | | | 190 | | |
| Glu | Arg | Glu | Ser | Ser | Ala | Asn | Asn | Ser | Val | Ser | Pro | Ser | Glu | Ser | Leu |
| | | 195 | | | | | 200 | | | | | 205 | | | |
| Arg | Ala | Ser | Glu | Lys | His | Arg | Gly | Ser | Ala | Asp | Tyr | Ser | Met | Glu | Ala |
| | 210 | | | | | 215 | | | | | 220 | | | | |
| Lys | Lys | Arg | Lys | Val | Glu | Glu | Lys | Asp | Ser | Leu | Ser | Arg | Tyr | Asp | Ser |
| 225 | | | | | 230 | | | | | 235 | | | | | 240 |
| Asp | Gly | Asp | Lys | Ser | Asp | Asp | Leu | Val | Val | Asp | Val | Ser | Asn | Glu | Asp |
| | | | | 245 | | | | | 250 | | | | | 255 | |
| Pro | Ala | Thr | Pro | Arg | Val | Ser | Pro | Ala | His | Ser | Pro | Pro | Glu | Asn | Gly |
| | | | 260 | | | | | 265 | | | | | 270 | | |
| Leu | Asp | Lys | Ala | Arg | Ser | Leu | Lys | Lys | Asp | Ala | Pro | Thr | Ser | Pro | Ala |
| | | 275 | | | | | 280 | | | | | 285 | | | |
| Ser | Val | Ala | Ser | Ser | Ser | Ser | Thr | Pro | Ser | Ser | Lys | Thr | Lys | Asp | Leu |
| | 290 | | | | | 295 | | | | | 300 | | | | |
| Gly | His | Asn | Asp | Lys | Ser | Ser | Thr | Pro | Gly | Leu | Lys | Ser | Asn | Thr | Pro |
| 305 | | | | | 310 | | | | | 315 | | | | | 320 |
| Thr | Pro | Arg | Asn | Asp | Ala | Pro | Thr | Pro | Gly | Thr | Ser | Thr | Thr | Pro | Gly |
| | | | | 325 | | | | | 330 | | | | | 335 | |
| Leu | Arg | Ser | Met | Pro | Gly | Lys | Pro | Pro | Gly | Met | Asp | Pro | Ile | Gly | Ile |
| | | | 340 | | | | | 345 | | | | | 350 | | |
| Met | Ala | Ser | Ala | Leu | Arg | Thr | Pro | Ile | Ser | Ile | Thr | Ser | Ser | Tyr | Ala |
| | | 355 | | | | | 360 | | | | | 365 | | | |
| Ala | Pro | Phe | Ala | Met | Met | Ser | His | His | Glu | Met | Asn | Gly | Ser | Leu | Thr |
| | 370 | | | | | 375 | | | | | 380 | | | | |
| Ser | Pro | Gly | Ala | Tyr | Ala | Gly | Leu | His | Asn | Ile | Pro | Pro | Gln | Met | Ser |
| 385 | | | | | 390 | | | | | 395 | | | | | 400 |
| Ala | Ala | Ala | Ala | Ala | Ala | Ala | Ala | Ala | Tyr | Gly | Arg | Ser | Pro | Met | Val |
| | | | | 405 | | | | | 410 | | | | | 415 | |
| Ser | Phe | Gly | Ala | Val | Gly | Phe | Asp | Pro | His | Pro | Pro | Met | Arg | Ala | Thr |
| | | | 420 | | | | | 425 | | | | | 430 | | |
| Gly | Leu | Pro | Ser | Ser | Leu | Ala | Ser | Ile | Pro | Gly | Gly | Lys | Pro | Ala | Tyr |
| | | 435 | | | | | 440 | | | | | 445 | | | |
| Ser | Phe | His | Val | Ser | Ala | Asp | Gly | Gln | Met | Gln | Pro | Val | Pro | Phe | Pro |
| | 450 | | | | | 455 | | | | | 460 | | | | |
| His | Asp | Ala | Leu | Ala | Gly | Pro | Gly | Ile | Pro | Arg | His | Ala | Arg | Gln | Ile |
| 465 | | | | | 470 | | | | | 475 | | | | | 480 |
| Asn | Thr | Leu | Ser | His | Gly | Gly | Val | Val | Cys | Ala | Val | Thr | Ile | Ser | Asn |
| | | | | 485 | | | | | 490 | | | | | 495 | |
| Pro | Ser | Arg | His | Val | Tyr | Thr | Gly | Gly | Lys | Gly | Cys | Val | Lys | Ile | Trp |
| | | | 500 | | | | | 505 | | | | | 510 | | |
| Asp | Ile | Ser | Gln | Pro | Gly | Ser | Lys | Ser | Pro | Ile | Ser | Gln | Leu | Asp | Cys |
| | | 515 | | | | | 520 | | | | | 525 | | | |
| Leu | Asn | Arg | Asp | Asn | Tyr | Met | Arg | Ser | Cys | Lys | Leu | His | Pro | Asp | Gly |
| | 530 | | | | | 535 | | | | | 540 | | | | |
| Arg | Thr | Leu | Ile | Val | Gly | Gly | Glu | Gly | Ser | Thr | Leu | Thr | Ile | Trp | Asp |
| 545 | | | | | 550 | | | | | 555 | | | | | 560 |

| | | | | | | | | | | | | | | |
|---|---|---|---|---|---|---|---|---|---|---|---|---|---|---|
| Leu | Ala | Ser | Pro | Thr | Pro | Arg | Ile | Lys | Ala | Glu | Leu | Thr | Ser | Ser | Ala |
| | | | | 565 | | | | 570 | | | | | 575 | |
| Pro | Ala | Cys | Tyr | Ala | Leu | Ala | Ile | Ser | Pro | Asp | Ala | Lys | Val | Cys | Phe |
| | | | 580 | | | | | 585 | | | | | 590 | |
| Ser | Cys | Cys | Ser | Asp | Gly | Asn | Ile | Ala | Val | Trp | Asp | Leu | His | Asn | Gln |
| | | 595 | | | | | 600 | | | | | 605 | | |
| Thr | Leu | Val | Arg | Gln | Phe | Gln | Gly | His | Thr | Asp | Gly | Ala | Ser | Cys | Ile |
| | 610 | | | | | 615 | | | | | 620 | | | |
| Asp | Ile | Ser | His | Asp | Gly | Thr | Lys | Leu | Trp | Thr | Gly | Gly | Leu | Asp | Asn |
| 625 | | | | | 630 | | | | | 635 | | | | | 640 |
| Thr | Val | Arg | Ser | Trp | Asp | Leu | Arg | Glu | Gly | Arg | Gln | Leu | Gln | Gln | His |
| | | | | 645 | | | | | 650 | | | | | 655 | |
| Asp | Phe | Thr | Ser | Gln | Ile | Phe | Ser | Leu | Gly | Tyr | Cys | Pro | Thr | Gly | Glu |
| | | | 660 | | | | | 665 | | | | | 670 | | |
| Trp | Leu | Ala | Val | Gly | Met | Glu | Ser | Ser | Asn | Val | Glu | Val | Leu | His | His |
| | | | 675 | | | | | 680 | | | | 685 | | | |
| Thr | Lys | Pro | His | Lys | Tyr | Gln | Leu | His | Leu | His | Glu | Ser | Cys | Val | Leu |
| | 690 | | | | | 695 | | | | | 700 | | | | |
| Ser | Leu | Lys | Phe | Ala | Tyr | Cys | Gly | Lys | Trp | Phe | Val | Ser | Thr | Gly | Lys |
| 705 | | | | | 710 | | | | | 715 | | | | | 720 |
| Asp | Asn | Leu | Leu | Asn | Ala | Trp | Arg | Thr | Pro | Tyr | Gly | Ala | Ser | Ile | Ser |
| | | | | 725 | | | | | 730 | | | | | 735 | |
| Gln | Ser | Lys | Glu | Ser | Ser | Ser | Val | Leu | Ser | Cys | Asp | Ile | Ser | Ala | Asp |
| | | | 740 | | | | | 745 | | | | | 750 | | |
| Asp | Lys | Tyr | Ile | Val | Thr | Gly | Ser | Gly | Asp | Lys | Lys | Ala | Thr | Val | Tyr |
| | | 755 | | | | | 760 | | | | | 765 | | | |
| Glu | Val | Ile | Tyr | | | | | | | | | | | | |
| | 770 | | | | | | | | | | | | | | |

( 2 ) INFORMATION FOR SEQ ID NO:7:

( i ) SEQUENCE CHARACTERISTICS:
        ( A ) LENGTH: 1443 base pairs
        ( B ) TYPE: nucleic acid
        ( C ) STRANDEDNESS: single
        ( D ) TOPOLOGY: unknown ( i i ) MOLECULE TYPE: DNA (cDNA)

( i x ) FEATURE:
        ( A ) NAME/KEY: CDS
        ( B ) LOCATION: 1..1344

( x i ) SEQUENCE DESCRIPTION: SEQ ID NO:7:

| | | | | | | | | | | | | | | | | |
|---|---|---|---|---|---|---|---|---|---|---|---|---|---|---|---|---|
| CCT | ACT | CCA | CGA | ACT | GAT | GCG | CCC | ACC | CCA | GGC | AGT | AAC | TCT | ACT | CCC | 48 |
| Pro | Thr | Pro | Arg | Thr | Asp | Ala | Pro | Thr | Pro | Gly | Ser | Asn | Ser | Thr | Pro | |
| 1 | | | | 5 | | | | | 10 | | | | | 15 | | |
| GGA | TTG | AGG | CCT | GTA | CCT | GGA | AAA | CCA | CCA | GGA | GTT | GAC | CCT | TTG | GCC | 96 |
| Gly | Leu | Arg | Pro | Val | Pro | Gly | Lys | Pro | Pro | Gly | Val | Asp | Pro | Leu | Ala | |
| | | | 20 | | | | | 25 | | | | | 30 | | | |
| TCA | AGC | CTA | AGG | ACC | CCA | ATG | GCA | GTA | CCT | TGT | CCA | TAT | CCA | ACT | CCA | 144 |
| Ser | Ser | Leu | Arg | Thr | Pro | Met | Ala | Val | Pro | Cys | Pro | Tyr | Pro | Thr | Pro | |
| | | 35 | | | | | 40 | | | | | 45 | | | | |
| TTT | GGG | ATT | GTG | CCC | CAT | GCT | GGA | ATG | AAC | GGA | GAG | CTG | ACC | AGC | CCC | 192 |
| Phe | Gly | Ile | Val | Pro | His | Ala | Gly | Met | Asn | Gly | Glu | Leu | Thr | Ser | Pro | |
| | 50 | | | | | 55 | | | | | 60 | | | | | |
| GGA | GCG | GCC | TAC | GCT | GGG | CTC | CAC | AAC | ATC | TCC | CCT | CAG | ATG | AGC | GCA | 240 |
| Gly | Ala | Ala | Tyr | Ala | Gly | Leu | His | Asn | Ile | Ser | Pro | Gln | Met | Ser | Ala | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| GCT | GCT | GCC | GCC | GCC | GCT | GCT | GCT | GCT | GCC | TAT | GGG | AGA | TCA | CCA | GTG | 288 |
| Ala | Ala | Ala | Ala | Ala | Ala | Ala | Ala | Ala | Ala | Tyr | Gly | Arg | Ser | Pro | Val | |
| | | | | 85 | | | | | 90 | | | | | 95 | | |
| GTG | GGA | TTT | GAT | CCA | CAC | CAT | CAC | ATG | CGT | GTG | CCA | GCA | ATA | CCT | CCA | 336 |
| Val | Gly | Phe | Asp | Pro | His | His | His | Met | Arg | Val | Pro | Ala | Ile | Pro | Pro | |
| | | | 100 | | | | | 105 | | | | | 110 | | | |
| AAC | CTG | ACA | GGC | ATT | CCA | GGA | GGA | AAA | CCA | GCA | TAC | TCC | TTC | CAT | GTT | 384 |
| Asn | Leu | Thr | Gly | Ile | Pro | Gly | Gly | Lys | Pro | Ala | Tyr | Ser | Phe | His | Val | |
| | | 115 | | | | | 120 | | | | | 125 | | | | |
| AGC | GCA | GAT | GGT | CAG | ATG | CAG | CCT | GTC | CCT | TTT | CCA | CCC | GAC | CCC | CTC | 432 |
| Ser | Ala | Asp | Gly | Gln | Met | Gln | Pro | Val | Pro | Phe | Pro | Pro | Asp | Pro | Leu | |
| | 130 | | | | | 135 | | | | | 140 | | | | | |
| ATC | GGA | CCT | GGA | ATC | CCC | CGG | CAT | GCT | CGC | CAG | ATC | AAC | ACC | CTC | AAC | 480 |
| Ile | Gly | Pro | Gly | Ile | Pro | Arg | His | Ala | Arg | Gln | Ile | Asn | Thr | Leu | Asn | |
| 145 | | | | | 150 | | | | | 155 | | | | | 160 | |
| CAC | GGG | GAG | GTG | GTG | TGC | GCG | GTG | ACC | ATC | AGC | AAC | CCC | ACG | AGA | CAC | 528 |
| His | Gly | Glu | Val | Val | Cys | Ala | Val | Thr | Ile | Ser | Asn | Pro | Thr | Arg | His | |
| | | | | 165 | | | | | 170 | | | | | 175 | | |
| GTG | TAC | ACG | GGT | GGG | AAG | GGC | GCG | GTC | AAG | GTC | TGG | GAC | ATC | AGC | CAC | 576 |
| Val | Tyr | Thr | Gly | Gly | Lys | Gly | Ala | Val | Lys | Val | Trp | Asp | Ile | Ser | His | |
| | | | 180 | | | | | 185 | | | | | 190 | | | |
| CCA | GGC | AAT | AAG | AGT | CCT | GTC | TCC | CAG | CTC | GAC | TGT | CTG | AAC | AGG | GAT | 624 |
| Pro | Gly | Asn | Lys | Ser | Pro | Val | Ser | Gln | Leu | Asp | Cys | Leu | Asn | Arg | Asp | |
| | | 195 | | | | | 200 | | | | | 205 | | | | |
| AAC | TAC | ATC | CGT | TCC | TGC | AGA | TTG | CTC | CCT | GAT | GGT | CGC | ACC | CTA | ATT | 672 |
| Asn | Tyr | Ile | Arg | Ser | Cys | Arg | Leu | Leu | Pro | Asp | Gly | Arg | Thr | Leu | Ile | |
| | 210 | | | | | 215 | | | | | 220 | | | | | |
| GTT | GGA | GGG | GAA | GCC | AGT | ACT | TTG | TCC | ATT | TGG | GAC | CTG | GCG | GCT | CCA | 720 |
| Val | Gly | Gly | Glu | Ala | Ser | Thr | Leu | Ser | Ile | Trp | Asp | Leu | Ala | Ala | Pro | |
| 225 | | | | | 230 | | | | | 235 | | | | | 240 | |
| ACC | CCA | CGC | ATC | AAG | GCA | GAG | CTG | ACA | TCC | TCG | GCC | CCC | GCC | TGC | TAT | 768 |
| Thr | Pro | Arg | Ile | Lys | Ala | Glu | Leu | Thr | Ser | Ser | Ala | Pro | Ala | Cys | Tyr | |
| | | | | 245 | | | | | 250 | | | | | 255 | | |
| GCC | CTG | GCC | ATC | AGC | CCC | GAT | TCC | AAG | GTC | TGC | TTC | TCA | TGC | TGC | AGC | 816 |
| Ala | Leu | Ala | Ile | Ser | Pro | Asp | Ser | Lys | Val | Cys | Phe | Ser | Cys | Cys | Ser | |
| | | | 260 | | | | | 265 | | | | | 270 | | | |
| GAC | GGC | AAC | ATC | GCT | GTG | TGG | GAT | CTG | CAC | AAC | CAG | ACC | TTG | GTG | AGG | 864 |
| Asp | Gly | Asn | Ile | Ala | Val | Trp | Asp | Leu | His | Asn | Gln | Thr | Leu | Val | Arg | |
| | | 275 | | | | | 280 | | | | | 285 | | | | |
| CAA | TTC | CAG | GGC | CAC | ACA | GAT | GGA | GCC | AGC | TGT | ATT | GAC | ATT | TCT | AAT | 912 |
| Gln | Phe | Gln | Gly | His | Thr | Asp | Gly | Ala | Ser | Cys | Ile | Asp | Ile | Ser | Asn | |
| | 290 | | | | | 295 | | | | | 300 | | | | | |
| GAT | GGC | ACC | AAG | CTC | TGG | ACA | GGT | GGT | TTG | GAC | AAC | ACG | GTC | AGG | TCC | 960 |
| Asp | Gly | Thr | Lys | Leu | Trp | Thr | Gly | Gly | Leu | Asp | Asn | Thr | Val | Arg | Ser | |
| 305 | | | | | 310 | | | | | 315 | | | | | 320 | |
| TGG | GAC | CTG | CGG | GAG | GGG | CGG | CAG | CTG | CAG | CAG | CAC | GAC | TTC | ACC | TCC | 1008 |
| Trp | Asp | Leu | Arg | Glu | Gly | Arg | Gln | Leu | Gln | Gln | His | Asp | Phe | Thr | Ser | |
| | | | | 325 | | | | | 330 | | | | | 335 | | |
| CAG | ATC | TTT | TCT | CTG | GGC | TAC | TGC | CCA | ACT | GGA | GAG | TGG | CTT | GCA | GTG | 1056 |
| Gln | Ile | Phe | Ser | Leu | Gly | Tyr | Cys | Pro | Thr | Gly | Glu | Trp | Leu | Ala | Val | |
| | | | 340 | | | | | 345 | | | | | 350 | | | |
| GGG | ATG | GAG | AAC | AGC | AAT | GTG | GAA | GTT | TTG | CAT | GTC | ACC | AAG | CCA | GAC | 1104 |
| Gly | Met | Glu | Asn | Ser | Asn | Val | Glu | Val | Leu | His | Val | Thr | Lys | Pro | Asp | |
| | | 355 | | | | | 360 | | | | | 365 | | | | |
| AAA | TAC | CAA | CTA | CAT | CTT | CAT | GAG | AGC | TGT | GTG | CTG | TCG | CTC | AAG | TTT | 1152 |
| Lys | Tyr | Gln | Leu | His | Leu | His | Glu | Ser | Cys | Val | Leu | Ser | Leu | Lys | Phe | |
| | 370 | | | | | 375 | | | | | 380 | | | | | |
| GCC | CAT | TGT | GGC | AAA | TGG | TTT | GTA | AGC | ACT | GGA | AAG | GAC | AAC | CTT | CTG | 1200 |
| Ala | His | Cys | Gly | Lys | Trp | Phe | Val | Ser | Thr | Gly | Lys | Asp | Asn | Leu | Leu | |
| 385 | | | | | 390 | | | | | 395 | | | | | 400 | |

```
AAT GCC TGG AGA ACG CCT TAC GGG GCC AGT ATA TTC CAG TCC AAA GAA    1248
Asn Ala Trp Arg Thr Pro Tyr Gly Ala Ser Ile Phe Gln Ser Lys Glu
            405                 410                 415

TCC TCA TCG GTG CTT AGC TGT GAC ATC TCC GTG GAC GAC AAA TAC ATT    1296
Ser Ser Ser Val Leu Ser Cys Asp Ile Ser Val Asp Asp Lys Tyr Ile
            420                 425                 430

GTC ACT GGC TCT GGG GAT AAG AAG GCC ACA GTT TAT GAA GTT ATT TAT    1344
Val Thr Gly Ser Gly Asp Lys Lys Ala Thr Val Tyr Glu Val Ile Tyr
            435                 440                 445

TAAAGACAAA TCTTCATGCA GACTGGACTT CTCCTCCTGG TAGCACTTTG CTCTGTCATC   1404

CTTTTGTTC ACCCCCATCC CCGCATCTAA AACCAAGGA                           1443
```

(2) INFORMATION FOR SEQ ID NO:8:

(i) SEQUENCE CHARACTERISTICS:
        (A) LENGTH: 448 amino acids
        (B) TYPE: amino acid
        (D) TOPOLOGY: unknown (ii) MOLECULE TYPE: protein (xi) SEQUENCE DESCRIPTION: SEQ ID NO:8:

```
Pro Thr Pro Arg Thr Asp Ala Pro Thr Pro Gly Ser Asn Ser Thr Pro
 1               5                  10                  15

Gly Leu Arg Pro Val Pro Gly Lys Pro Pro Gly Val Asp Pro Leu Ala
            20                  25                  30

Ser Ser Leu Arg Thr Pro Met Ala Val Pro Cys Pro Tyr Pro Thr Pro
            35                  40                  45

Phe Gly Ile Val Pro His Ala Gly Met Asn Gly Glu Leu Thr Ser Pro
 50                  55                  60

Gly Ala Ala Tyr Ala Gly Leu His Asn Ile Ser Pro Gln Met Ser Ala
65                  70                  75                  80

Ala Ala Ala Ala Ala Ala Ala Ala Ala Ala Tyr Gly Arg Ser Pro Val
                85                  90                  95

Val Gly Phe Asp Pro His His His Met Arg Val Pro Ala Ile Pro Pro
            100                 105                 110

Asn Leu Thr Gly Ile Pro Gly Gly Lys Pro Ala Tyr Ser Phe His Val
            115                 120                 125

Ser Ala Asp Gly Gln Met Gln Pro Val Pro Phe Pro Pro Asp Pro Leu
    130                 135                 140

Ile Gly Pro Gly Ile Pro Arg His Ala Arg Gln Ile Asn Thr Leu Asn
145                 150                 155                 160

His Gly Glu Val Val Cys Ala Val Thr Ile Ser Asn Pro Thr Arg His
                165                 170                 175

Val Tyr Thr Gly Gly Lys Gly Ala Val Lys Val Trp Asp Ile Ser His
            180                 185                 190

Pro Gly Asn Lys Ser Pro Val Ser Gln Leu Asp Cys Leu Asn Arg Asp
            195                 200                 205

Asn Tyr Ile Arg Ser Cys Arg Leu Leu Pro Asp Gly Arg Thr Leu Ile
    210                 215                 220

Val Gly Gly Glu Ala Ser Thr Leu Ser Ile Trp Asp Leu Ala Ala Pro
225                 230                 235                 240

Thr Pro Arg Ile Lys Ala Glu Leu Thr Ser Ser Ala Pro Ala Cys Tyr
                245                 250                 255

Ala Leu Ala Ile Ser Pro Asp Ser Lys Val Cys Phe Ser Cys Cys Ser
            260                 265                 270
```

| | | | | | | | | | | | | | | |
|---|---|---|---|---|---|---|---|---|---|---|---|---|---|---|
|Asp|Gly|Asn|Ile|Ala|Val|Trp|Asp|Leu|His|Asn|Gln|Thr|Leu|Val|Arg|
| |275| | | |280| | | | |285| | | | | |
|Gln|Phe|Gln|Gly|His|Thr|Asp|Gly|Ala|Ser|Cys|Ile|Asp|Ile|Ser|Asn|
| |290| | | |295| | | | |300| | | | | |
|Asp|Gly|Thr|Lys|Leu|Trp|Thr|Gly|Gly|Leu|Asp|Asn|Thr|Val|Arg|Ser|
|305| | | | |310| | | | |315| | | | |320|
|Trp|Asp|Leu|Arg|Glu|Gly|Arg|Gln|Leu|Gln|Gln|His|Asp|Phe|Thr|Ser|
| | | | |325| | | | |330| | | | |335| |
|Gln|Ile|Phe|Ser|Leu|Gly|Tyr|Cys|Pro|Thr|Gly|Glu|Trp|Leu|Ala|Val|
| | | |340| | | | |345| | | | |350| | |
|Gly|Met|Glu|Asn|Ser|Asn|Val|Glu|Val|Leu|His|Val|Thr|Lys|Pro|Asp|
| | |355| | | | |360| | | | |365| | | |
|Lys|Tyr|Gln|Leu|His|Leu|His|Glu|Ser|Cys|Val|Leu|Ser|Leu|Lys|Phe|
| |370| | | | |375| | | | |380| | | | |
|Ala|His|Cys|Gly|Lys|Trp|Phe|Val|Ser|Thr|Gly|Lys|Asp|Asn|Leu|Leu|
|385| | | | |390| | | | |395| | | | |400|
|Asn|Ala|Trp|Arg|Thr|Pro|Tyr|Gly|Ala|Ser|Ile|Phe|Gln|Ser|Lys|Glu|
| | | | |405| | | | |410| | | | |415| |
|Ser|Ser|Ser|Val|Leu|Ser|Cys|Asp|Ile|Ser|Val|Asp|Asp|Lys|Tyr|Ile|
| | | |420| | | | |425| | | | |430| | |
|Val|Thr|Gly|Ser|Gly|Asp|Lys|Lys|Ala|Thr|Val|Tyr|Glu|Val|Ile|Tyr|
| | |435| | | | |440| | | | |445| | | |

( 2 ) INFORMATION FOR SEQ ID NO:9:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: unknown ( i i ) MOLECULE TYPE: protein ( i x ) FEATURE:
        ( A ) NAME/KEY: Modified-site
        ( B ) LOCATION: 6
        ( D ) OTHER INFORMATION: /label=X
            / note='"X =Asp or Glu'"

( i x ) FEATURE:
        ( A ) NAME/KEY: Modified-site
        ( B ) LOCATION: 17
        ( D ) OTHER INFORMATION: /label=X
            / note='"X =Ile or Leu'"

( i x ) FEATURE:
        ( A ) NAME/KEY: Modified-site
        ( B ) LOCATION: 19
        ( D ) OTHER INFORMATION: /label=X
            / note='"X =Ile or Leu'"

( i x ) FEATURE:
        ( A ) NAME/KEY: Modified-site
        ( B ) LOCATION: 24
        ( D ) OTHER INFORMATION: /label=X
            / note='"X =Thr or Ser'"

( i x ) FEATURE:
        ( A ) NAME/KEY: Modified-site
        ( B ) LOCATION: 28
        ( D ) OTHER INFORMATION: /label=X
            / note='"X =Thr or Ser'"

( x i ) SEQUENCE DESCRIPTION: SEQ ID NO:9:

| | | | | | | | | | | | | | | |
|---|---|---|---|---|---|---|---|---|---|---|---|---|---|---|
|Pro|Xaa|Xaa|Xaa|Xaa|Xaa|Xaa|Thr|Xaa|Xaa|Xaa|Xaa|Xaa|Xaa|Xaa|Xaa|
|1| | | |5| | | | |10| | | | |15| |

-continued

```
Xaa Xaa Xaa Ser Pro Asp Gly Xaa Xaa Leu Xaa Xaa Gly Gly Xaa Asp
         20                  25                  30

Gly Xaa Val Xaa Xaa Trp Asp Leu Xaa
         35              40
```

(2) INFORMATION FOR SEQ ID NO:10:

(i) SEQUENCE CHARACTERISTICS:
    (A) LENGTH: 719 amino acids
    (B) TYPE: amino acid
    (C) STRANDEDNESS: single
    (D) TOPOLOGY: unknown (ii) MOLECULE TYPE: protein (xi) SEQUENCE DESCRIPTION: SEQ ID NO:10:

```
Met Tyr Pro Ser Pro Val Arg His Pro Ala Ala Gly Gly Pro Pro Pro
 1               5                  10                  15

Gln Gly Pro Ile Lys Phe Thr Ile Ala Asp Thr Leu Glu Arg Ile Lys
             20                  25                  30

Glu Glu Phe Asn Phe Leu Gln Ala His Tyr His Ser Ile Lys Leu Glu
         35                  40                  45

Cys Glu Lys Leu Ser Asn Glu Lys Thr Glu Met Gln Arg His Tyr Val
     50                  55                  60

Met Tyr Tyr Glu Met Ser Tyr Gly Leu Asn Val Glu Met His Lys Gln
 65                  70                  75                  80

Thr Glu Ile Ala Lys Arg Leu Asn Thr Leu Ile Asn Gln Leu Leu Pro
                 85                  90                  95

Phe Leu Gln Ala Asp His Gln Gln Gln Val Leu Gln Ala Val Glu Arg
             100                 105                 110

Ala Lys Gln Val Thr Met Gln Glu Leu Asn Leu Ile Ile Gly Gln Gln
         115                 120                 125

Ile His Ala Gln Gln Val Pro Gly Gly Pro Pro Gln Pro Met Gly Ala
     130                 135                 140

Leu Asn Pro Phe Gly Ala Leu Gly Ala Thr Met Gly Leu Pro His Gly
145                 150                 155                 160

Pro Gln Gly Leu Leu Asn Lys Pro Pro Glu His His Arg Pro Asp Ile
                 165                 170                 175

Lys Pro Thr Gly Leu Glu Gly Pro Ala Ala Ala Glu Glu Arg Leu Arg
             180                 185                 190

Asn Ser Val Ser Pro Ala Asp Arg Glu Lys Tyr Arg Thr Arg Ser Pro
         195                 200                 205

Leu Asp Ile Glu Asn Asp Ser Lys Arg Arg Lys Asp Glu Lys Leu Gln
     210                 215                 220

Glu Asp Glu Gly Glu Lys Ser Asp Gln Asp Leu Val Val Asp Val Ala
225                 230                 235                 240

Asn Glu Met Glu Ser His Ser Pro Arg Pro Asn Gly Glu His Val Ser
                 245                 250                 255

Met Glu Val Arg Asp Arg Glu Ser Leu Asn Gly Glu Arg Leu Glu Lys
             260                 265                 270

Pro Ser Ser Ser Gly Ile Lys Gln Glu Arg Pro Pro Ser Arg Ser Gly
         275                 280                 285

Ser Ser Ser Ser Arg Ser Thr Pro Ser Leu Lys Thr Lys Asp Met Glu
     290                 295                 300

Lys Pro Gly Thr Pro Gly Ala Lys Ala Arg Thr Pro Thr Pro Asn Ala
305                 310                 315                 320
```

```
Ala Ala Pro Ala Pro Gly Val Asn Pro Lys Gln Met Met Pro Gln Gly
            325                 330                 335

Pro Pro Pro Ala Gly Tyr Pro Gly Ala Pro Tyr Gln Arg Pro Ala Asp
            340                 345                 350

Pro Tyr Gln Arg Pro Pro Ser Asp Pro Ala Tyr Gly Arg Pro Pro Pro
        355                 360                 365

Met Pro Tyr Asp Pro His Ala His Val Arg Thr Asn Gly Ile Pro His
    370                 375                 380

Pro Ser Ala Leu Thr Gly Gly Lys Pro Ala Tyr Ser Phe His Met Asn
385                 390                 395                 400

Gly Glu Gly Ser Leu Gln Pro Val Pro Phe Pro Pro Asp Ala Leu Val
                405                 410                 415

Gly Val Gly Ile Pro Arg His Ala Arg Gln Ile Asn Thr Leu Ser His
            420                 425                 430

Gly Glu Val Val Cys Ala Val Thr Ile Ser Asn Pro Thr Lys Tyr Val
        435                 440                 445

Tyr Thr Gly Gly Lys Gly Cys Val Lys Val Trp Asp Ile Ser Gln Pro
    450                 455                 460

Gly Asn Lys Asn Pro Val Ser Gln Leu Asp Cys Leu Gln Arg Asp Asn
465                 470                 475                 480

Tyr Ile Arg Ser Val Lys Leu Leu Pro Asp Gly Arg Thr Leu Ile Val
                485                 490                 495

Gly Gly Glu Ala Ser Asn Leu Ser Ile Trp Asp Leu Ala Ser Pro Thr
            500                 505                 510

Pro Arg Ile Lys Ala Glu Leu Thr Ser Ala Ala Pro Ala Cys Tyr Ala
        515                 520                 525

Leu Ala Ile Ser Pro Asp Ser Lys Val Cys Phe Ser Cys Cys Ser Asp
    530                 535                 540

Gly Asn Ile Ala Val Trp Asp Leu His Asn Glu Ile Leu Val Arg Gln
545                 550                 555                 560

Phe Gln Gly His Thr Asp Gly Ala Ser Cys Ile Asp Ile Ser Pro Asp
                565                 570                 575

Gly Ser Arg Leu Trp Thr Gly Gly Leu Asp Asn Thr Val Arg Ser Trp
            580                 585                 590

Asp Leu Arg Glu Gly Arg Gln Leu Gln Gln His Asp Phe Ser Ser Gln
        595                 600                 605

Ile Phe Ser Leu Gly Tyr Cys Pro Thr Gly Asp Trp Leu Ala Val Gly
    610                 615                 620

Met Glu Asn Ser His Val Glu Val Leu His Ala Ser Lys Pro Asp Lys
625                 630                 635                 640

Tyr Gln Leu His Leu His Glu Ser Cys Val Leu Ser Leu Arg Phe Ala
                645                 650                 655

Ala Cys Gly Lys Trp Phe Val Ser Thr Gly Lys Asp Asn Leu Leu Asn
            660                 665                 670

Ala Trp Arg Thr Pro Tyr Gly Ala Ser Ile Phe Gln Ser Lys Glu Thr
        675                 680                 685

Ser Ser Val Leu Ser Cys Asp Ile Ser Thr Asp Asp Lys Tyr Ile Val
    690                 695                 700

Thr Gly Ser Gly Asp Lys Lys Ala Thr Val Tyr Glu Val Ile Tyr
705                 710                 715
```

( 2 ) INFORMATION FOR SEQ ID NO:11:

( i ) SEQUENCE CHARACTERISTICS:

(A) LENGTH: 4 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:11:

Lys Lys Arg Lys
    1

(2) INFORMATION FOR SEQ ID NO:12:

(i) SEQUENCE CHARACTERISTICS:
        (A) LENGTH: 5 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:12:

Ser Ser Asp Asp Glu
    1               5

(2) INFORMATION FOR SEQ ID NO:13:

(i) SEQUENCE CHARACTERISTICS:
        (A) LENGTH: 5 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:13:

Ser Thr Pro Pro Lys
    1               5

(2) INFORMATION FOR SEQ ID NO:14:

(i) SEQUENCE CHARACTERISTICS:
        (A) LENGTH: 4 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:14:

Arg Gln Arg Arg
    1

(2) INFORMATION FOR SEQ ID NO:15:

(i) SEQUENCE CHARACTERISTICS:
        (A) LENGTH: 5 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:15:

Ser Ser Asp Thr Glu
    1               5

(2) INFORMATION FOR SEQ ID NO:16:

(i) SEQUENCE CHARACTERISTICS:

(A) LENGTH: 5 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO:16:

Thr Ser Pro Arg Ser
    1               5

(2) INFORMATION FOR SEQ ID NO:17:

(i) SEQUENCE CHARACTERISTICS:
            (A) LENGTH: 4 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO:17:

Lys Lys Lys Pro
    1

(2) INFORMATION FOR SEQ ID NO:18:

(i) SEQUENCE CHARACTERISTICS:
            (A) LENGTH: 4 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO:18:

Thr Glu Glu Glu
    1

(2) INFORMATION FOR SEQ ID NO:19:

(i) SEQUENCE CHARACTERISTICS:
            (A) LENGTH: 5 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO:19:

Ser Ser Pro Gln Pro
    1               5

(2) INFORMATION FOR SEQ ID NO:20:

(i) SEQUENCE CHARACTERISTICS:
            (A) LENGTH: 4 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO:20:

Arg Lys Lys Arg
    1

(2) INFORMATION FOR SEQ ID NO:21:

(i) SEQUENCE CHARACTERISTICS:

(A) LENGTH: 4 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:21:

Ser Leu Asn Asp
1

(2) INFORMATION FOR SEQ ID NO:22:

(i) SEQUENCE CHARACTERISTICS:
(A) LENGTH: 4 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:22:

Thr Arg Leu Lys
1

(2) INFORMATION FOR SEQ ID NO:23:

(i) SEQUENCE CHARACTERISTICS:
(A) LENGTH: 4 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:23:

Lys Arg Gln Lys
1

(2) INFORMATION FOR SEQ ID NO:24:

(i) SEQUENCE CHARACTERISTICS:
(A) LENGTH: 8 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:24:

Ser Asp Gly Val Thr Ser Glu Ala
1               5

(2) INFORMATION FOR SEQ ID NO:25:

(i) SEQUENCE CHARACTERISTICS:
(A) LENGTH: 4 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:25:

Thr Pro Arg Tyr
1

THERAPEUTIC AND DIAGNOSTIC METHODS AND COMPOSITIONS BASED ON TRANSDUCIN-LIKE ENHANCER OF SPLIT PROTEINS AND NUCLEIC ACIDS

This invention was made in part with government support under grant number NS 26084 awarded by the National Institutes of Health. The government has certain rights in the invention.

This application is a continuation of application Ser. No. 07/954,813 filed Sep. 30, 1992, now abandoned.

1. INTRODUCTION

The present invention relates to therapeutic compositions comprising transducin-like Enhancer of split ("TLE") proteins, analogs and derivatives thereof, antibodies thereto, nucleic acids encoding the TLE proteins, derivatives or analogs, TLE antisense nucleic acids, and proteins which bind to TLE proteins and their nucleic acids and antibodies. Therapeutic and diagnostic methods are also provided.

2. BACKGROUND OF THE INVENTION

2.1. THE NOTCH GENE AND PROTEIN

In *Drosophila melanogaster*, the so called "Notch group" of genes has been implicated in events crucial for the correct developmental choices of a wide variety of precursor cells (for review, see Artavanis-Tsakonas and Simpson, 1991, Trends Genet. 7:403–408). The accumulated genetic and molecular studies suggest that these genes encode elements of a cell communication mechanism which includes cell surface, cytoplasmic, and nuclear components.

The central player of the Notch group is the Notch (N) locus which encodes a transmembrane protein containing EGF-like repeats in its extracellular domain (Wharton et al., 1985, Cell 43:567–581; Kidd et at., 1986, Mol. Cell. Biol. 6:3094–3108). This protein has been shown to interact molecularly and genetically with two other transmembrane, EGF-containing proteins of the Notch group: Serrate and Delta (Vaessin et al., 1985, J. Neurogenetics 2:291–308; Fehon et al., 1990, Cell 61:523–534; Fleming et al., 1990, Genes Dev. 4:2188–2201; Xu et al., 1990, Genes Dev. 4:464–475; Rebay et al., 1991, Cell 67:687–699; Thomas et al., 1991, Development 111:749–761). The other members of the Notch group are deltex (Xu and Artavanis-Tsakonas, 1991, Genetics 126:665–677), Enhancer of (split) [E(spl)] (Knust et al., 1987, EMBO J. 6:4113–4123; Hartley et al., 1988, Cell 55:785–795; Preiss et al., 1988, EMBO J. 7:3917–3927; Klambt et al., 1989, EMBO J. 8:203–210), and mastermind (mam) (Smoller et al., 1990, Genes Dev. 4:1688–1700). mastermind and Enhancer of (split) encode nuclear proteins (Smoller et al., 1990, Genes Dev. 4:1688–1700; Delidakis et al., 1991, Genetics 129:803–823).

Notch homologs have been isolated from a variety of vertebrate species and have been shown to be remarkably similar to their Drosophila counterpart in terms of structure, expression pattern and ligand binding properties (Rebay et al., 1991, Cell 67:687–699; Coffman et al., 1990, Science 249:1438–1441; Ellisen et al, 1991, Cell 66:649–661; Weinmaster et al., 1991, Development 113:199–205). A human Notch (TAN-1) malfunction has been associated with a lymphatic cancer (Ellisen et al, 1991, Cell 66:649–661).

Notch is expressed on axonal processes during the outgrowth of embryonic neurons (Johansen et at., 1989, J. Cell Biol. 109, 2427–2440; Kidd et al., 1989, Genes Dev. 3, 1113–1129). A study has shown that certain Ax alleles of Notch can severely alter axon pathfinding during sensory neural outgrowth in the imaginal discs, although it is not yet known whether aberrant Notch expression in the axon itself or the epithelium along which it grows is responsible for this defect (Palka et at., 1990, Development 109, 167–175).

E(spl) is a complex locus comprised of at least ten genetically related transcription units which have been separated into two distinct groups, both of which display genetic interactions with specific Notch mutations (Knust et al., 1987, EMBO J. 6:4113–4123; Hartley et al., 1988, Cell 55:785–795; Preiss et at., 1988, EMBO J. 7:3917–3927; Klambt et al., 1989, EMBO J. 8:203–210; Delidakis et al., 1991, Genetics 129:803–823). The first group codes for proteins containing the helix-loop-helix motif (Klambt et al., 1989, EMBO J. 8:203–210) while the second displays homology to the β subunit of transducin (Hartley et al., 1988, Cell 55:785–795). Knust et al. (1987, EMBO J. 6:4113–4123) have numbered the transcripts in the E(spl) region and, according to their numbering system, the transcripts coding for the transducin-homologous protein are termed m9/10. Several embryonic lethal alleles affecting this gene were isolated. Moreover, P element transformation analyses demonstrated that the mutation groucho, which affects bristle development in Drosophila, is allelic to the Enhancer of split m9/10 gene (Hartley et al., 1988, Cell 55:785–795; Preiss et al., 1988, EMBO J. 7:3917–3927).

The 719 amino acid long product of the E(spl) m9/10 gene contains four tandemly arranged repeats spanning the carboxyl-terminal ~300 amino acid residues of the protein (Hartley et al., 1988, Cell 55:785–795). Each repeat is approximately 40 residues in length and is characterized by the presence of the conserved motif WDL. Such repeats are found similarly arranged in the β subunits of G proteins and have been referred to as the "WD-40 repeat" (for review, see Simon et al., 1991, Science 252:802–808). Several other proteins containing this structural motif include the products of the yeast cell cycle gene CDC 4 (Yochem and Byers, 1987, J. Mol. Biol. 195:233–245) and of the TUP1 gene, a mediator of glucose repression (Williams and Trumbly, 1990, Mol. Cell. Biol. 10:6500–6511.).

Very little is known about the mechanisms underlying cell fate choices in higher organisms such as vertebrates; a knowledge of such mechanisms could provide insights into pathologies associated with abnormal differentiation events. Thus, a need exists in the art to obtain and characterize the human members of the "Notch group" of genes, including Enhancer of split, since these genes appear to play crucial roles in the determination of cell fate.

2.2. CANCER

A neoplasm, or tumor, is a neoplastic mass resulting from abnormal uncontrolled cell growth, which may cause swelling on the body surface, and which can be benign or malignant. Benign tumors generally remain localized. Malignant tumors are collectively termed cancers. The term "malignant" generally means that the tumor can invade and destroy neighboring body structures and spread to distant sites to cause death (for review, see Robbins and Angell, 1976, *Basic Pathology*, 2d Ed., W. B. Saunders Co., Philadelphia, pp. 68–122).

Effective treatment and prevention of cancer remains a long-felt need, and a major goal of biomedical research.

3. SUMMARY OF THE INVENTION

The present invention relates to therapeutic and diagnostic methods and compositions based on transducin-like Enhancer of split ("TLE") proteins and nucleic acids. The invention provides for treatment of disorders of cell fate or differentiation by administration of a therapeutic compound of the invention. Such therapeutic compounds (termed herein "Therapeutics") include: TLE proteins and analogs and derivatives (including fragments) thereof; antibodies thereto; nucleic acids encoding the TLE proteins, analogs, or derivatives; TLE antisense nucleic acids; as well as toporythmic and other proteins and derivatives which bind to or otherwise interact with TLE proteins, and their encoding nucleic acids and antibodies. In a preferred embodiment, a Therapeutic of the invention is administered to treat a cancerous condition, or to prevent progression from a preneoplastic or non-malignant state into a neoplastic or a malignant state. In other specific embodiments, a Therapeutic of the invention is administered to treat a nervous system disorder or to promote tissue regeneration and repair.

In one embodiment, Therapeutics which antagonize, or inhibit, TLE function (hereinafter "Antagonist Therapeutics") are administered for therapeutic effect; disorders which can be thus treated can be identified by in vitro assays such as described in Section 5.1, infra. Such Antagonist Therapeutics include but are not limited to TLE antisense nucleic acids, anti-TLE neutralizing antibodies, and competitive inhibitors of TLE protein-protein interactions, all as detailed infra.

In another embodiment, Therapeutics which promote TLE function (hereinafter "Agonist Therapeutics") are administered for therapeutic effect; disorders which can thus be treated can be identified by in vitro assays such as described in Section 5.1, infra. Such Agonist Therapeutics include but are not limited to TLE proteins and derivatives thereof and proteins that interact with TLE proteins (e.g., protein components of multiprotein complexes containing TLE protein(s) (see Section 5.11).

Disorders of cell fate, in particular hyperproliferative (e.g., cancer) or hypoproliferative disorders, involving aberrant or undesirable levels of expression or activity of TLE protein can be diagnosed by detecting such levels, as described more fully infra.

4. DESCRIPTION OF THE FIGURES

FIGS. 1A–1H. Nucleotide sequence (SEQ ID NO: 1) and deduced amino acid sequence (SEQ ID NO:2) of TLE 1.

FIGS. 2A–2G. Nucleotide sequence (SEQ ID NO:3) and deduced amino acid sequence (SEQ ID NO:4) of TLE 2.

FIGS. 3A–3G. Nucleotide sequence (SEQ ID NO:5) and deduced amino acid sequence (SEQ ID NO:6) of TLE 3.

FIGS. 4A–4E. Partial nucleotide sequence (SEQ ID NO:7) and deduced amino acid sequence (SEQ ID NO:8) of TLE 4.

FIGS. 5A–5C. Comparison of the amino acid sequence of Drosophila E(spl) m9/10 (SEQ ID NO:10) and human TLE proteins 1–4 (SEQ ID NOS:2, 4, 6and 8, respectively). Amino acids are numbered on the left side. Identical residues in all compared sequences are boxed, while residues identical in either three out of four or four out of five sequences are indicated in boldface type. Alignments maximize continuity between all sequences. Underlined amino acid residues correspond to the CcN motif.

FIG. 6. Comparison of the WD-40 domains of Drosophila E(spl) m9/10 and TLE proteins 1–4 (portions of SEQ ID NOS:2, 4, 6 and 8, respectively). Amino acids are numbered on the left side. Those residues that are identical in each of the five sequences are boxed, while residues identical in four out of five sequences are indicated in boldface type. Those amino acids that are present at a given position in at least 10 out of 20 repeats define the consensus residues (SEQ ID NO:9) indicated at the bottom of the figure.

FIGS. 7A–7D. Expression of TLE mRNAs. Human poly (A)$^+$ RNA ("MTN Blot", catalog #7760-1; 2 µg/lane) was obtained from Clontech. Northern blotting experiments were performed at 42° C. in a buffer containing 50% formamide, 5× SSPE, 5× Denhardt's solution, 0.5% SDS, and 100 µg/ml of salmon sperm DNA. After hybridization for 16 hr in the presence of [$^{32}$P]-labeled probes, blots were washed in 1× SCC, 0.1% SDS once at room temperature and 3 times at 68° C., followed by three washes at 68° C. in 0.2× SSC, 0.1% SDS. Individual probes corresponded to the following amino acid regions: TLE 1 (a), residues 260 through 435; TLE 2 (b), 32 through 342; TLE 3 (c), 350 through 440; TLE 4 (d), the region corresponding to that covered by the TLE 3 probe. RNA size markers (in kb) are indicated at the left of each autoradiogram. The arrows on the right of each panel indicate the sizes of the major TLE-specific transcripts.

Figure 8A:
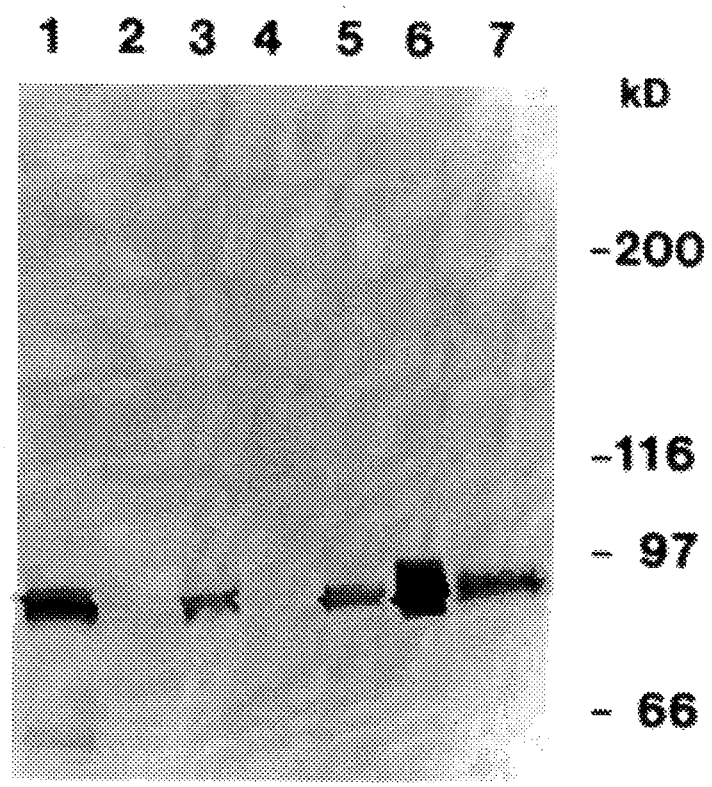
Figure 8B:
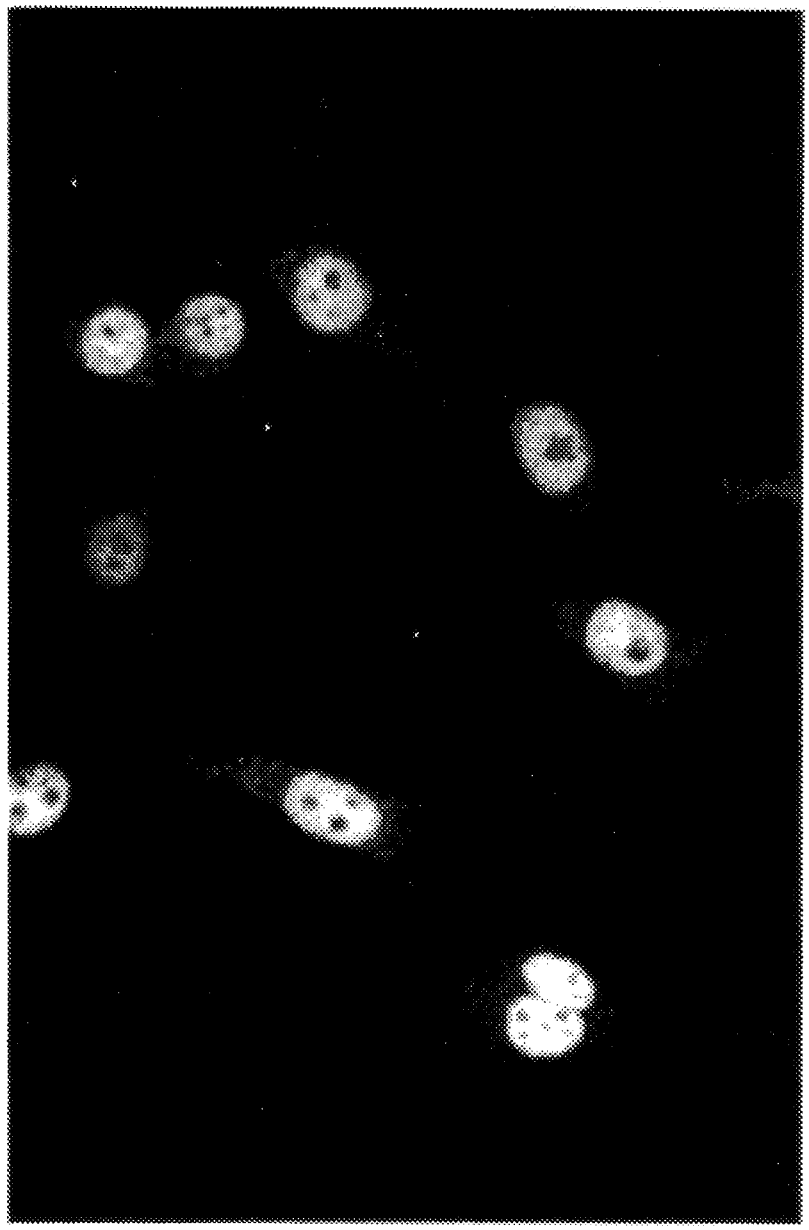

FIGS. 8A and 8B. Immunocytochemical characterization of TLE proteins. (8A) Western blotting analysis of TLE proteins. Protein extracts from human thymus (lane 1; 250 µg of protein/lane), spleen (lane 2; 250 µg of protein/lane), lung (lane 3; 200 µg of protein/lane), heart (lane 4; 180 µg of protein/lane), kidney (lane 5; 200 µg of protein/lane), SUP-T1 cells (Ellisen et al., 1991, Cell 66:649–661) (lane 6; 180 µg of protein/lane), and HeLa cells (lane 7; 150 µg of protein/lane) were prepared and subjected to SDS-polyacrylamide gel electrophoresis (PAGE) on a 6% gel as described in Section 6.3. Western blotting was performed in the presence of a 1:10 dilution of the rat monoclonal antibody C597.4A. Bound antibodies were detected by incubation with goat anti-rat IgG conjugated to horseradish peroxidase (1:1000). Molecular size standards are also indicated. (8B) Intracellular localization of TLE proteins. HeLa cells were grown on chamber slides, fixed with paraformaldehyde, and stained with monoclonal antibody C597.4A.

Figure 9:
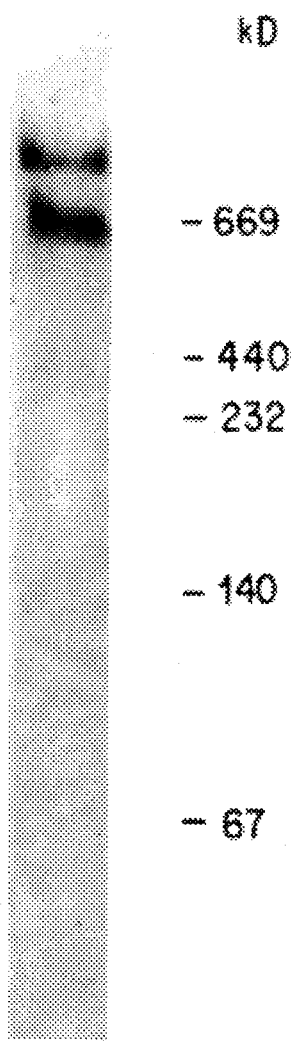

FIG. 9. Western blot visualization of multiprotein complexes containing TLE proteins after non-denaturing polyacrylamide gel electrophoresis (PAGE). A high speed supernatant fraction from human HeLa cell lysates was subjected to non-denaturing PAGE, proteins were transferred to nitrocellulose filters and probed in a Western blotting procedure with monoclonal antibody C597.4A, which binds to all TLE proteins. Two major immunoreactive species were detected, with apparent molecular weights of greater than 670,000 daltons.

Figure 10A:
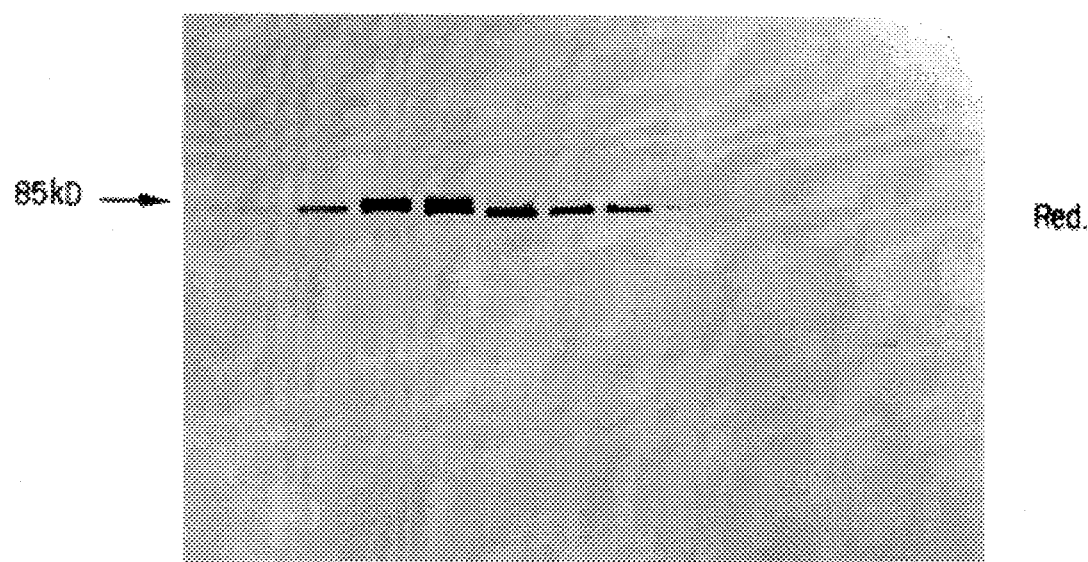
Figure 10B:
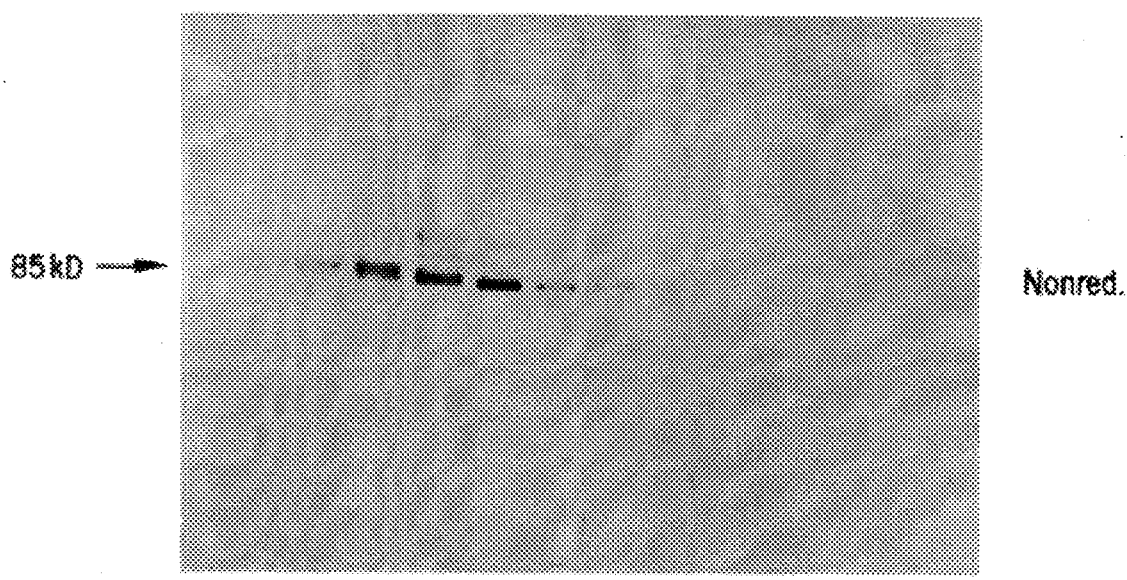

FIGS. 10A–10B. Gel filtration chromatography of multiprotein complexes containing TLE proteins. High speed supernatant fractions from HeLa cells were subjected to gel filtration chromatography using a Sephacryl S-300 matrix. The fractions collected from the column were analyzed for the presence of TLE proteins in Western blotting experiments with monoclonal antibody C597.4A. FIG. 8A shows the results after SDS-PAGE under reducing conditions; FIG. 8B shows the results after SDS-PAGE under nonreducing conditions. Positions of elution of Dextran Blue (D.B.) and of molecular weight standards of 116 kD and of 80 kD are shown at the top of FIG. 8A.

Figure 11A:
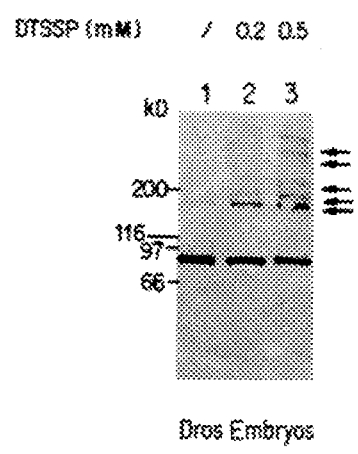
Figure 11B:
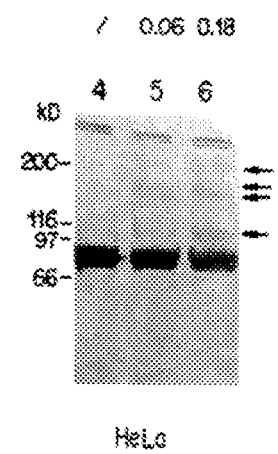
Figure 11C:
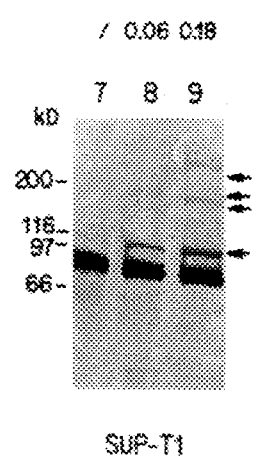

FIGS. 11A–11C. Western blots of cross-linked protein complexes containing TLE proteins. Protein extracts from Drosophila embryos (lanes 1–3), HeLa cells (lanes 4–6) or SUP-T1 cells (lanes 7–9) were incubated in the presence of increasing concentrations of the chemical cross-linker, DTSSP. Concentrations used of DTSSP were as follows (in mM): Lanes 1, 4, and 7: 0; Lane 2: 0.2; Lane 3: 0.5; Lane 5: 0.06; Lane 6: 0.18; Lane 8: 0.06; Lane 9: 0.18. The products of the cross-linking reactions were subjected to SDS-PAGE under non-reducing conditions, followed by transfer to nitrocellulose membranes, and Western blotting with either monoclonal antibody 3C, directed against Enhancer of split m9/10 (lanes 1–3), or monoclonal antibody C597.4A, directed against the TLE proteins (lanes 4–9). The positions of migration of molecular size markers are shown at right.

5. DETAILED DESCRIPTION OF THE INVENTION

The present invention relates to therapeutic and diagnostic methods and compositions based on transducin-like Enhancer of split [E(spl)] ("TLE") proteins and nucleic acids. As used herein, the term "TLE" with reference to genes or proteins, shall refer to the transducin-like E(spl)-homologous genes or their encoded proteins, as the case may be, without reference to any species. The invention provides for treatment of disorders of cell fate or differentiation by administration of a therapeutic compound of the invention. Such therapeutic compounds (termed herein "Therapeutics") include: TLE proteins and analogs and derivatives (including fragments) thereof; antibodies thereto; nucleic acids encoding the TLE proteins, analogs, or derivatives; TLE antisense nucleic acids; as well as toporythmic or other proteins and derivatives and analogs thereof which bind to or otherwise interact with TLE proteins, and their encoding nucleic acids and antibodies. Also included are proteins and derivatives and analogs thereof which are capable of inhibiting the interactions of a TLE protein with another protein (e.g. a ~17 kD protein (see Section 7), or possibly Delta, Serrate). In a preferred embodiment, a Therapeutic of the invention is administered to treat a cancerous condition, or to prevent progression from a pre-neoplastic or non-malignant state (e.g., metaplastic condition) into a neoplastic or a malignant state. In another specific embodiment, a Therapeutic of the invention is administered to treat a nervous system disorder, such as nerve injury or a degenerative disease. In yet another specific embodiment, a Therapeutic of the invention is administered to promote tissue regeneration and repair for treatment of various conditions. In a preferred embodiment, the Therapeutic of the invention is a human TLE nucleic acid or protein.

In one embodiment, Therapeutics which antagonize, or inhibit, TLE function (hereinafter "Antagonist Therapeutics") are administered for therapeutic effect; disorders which can be thus treated can be identified by in vitro assays such as described in Section 5.1, infra. Such Antagonist Therapeutics include but are not limited to TLE antisense nucleic acids, anti-TLE neutralizing antibodies, and competitive inhibitors of TLE protein-protein interactions, all as detailed infra.

In another embodiment, Therapeutics which promote TLE function (hereinafter "Agonist Therapeutics") are administered for therapeutic effect; disorders which can thus be treated can be identified by in vitro assays such as described in Section 5.1, infra. Such Agonist Therapeutics include but are not limited to TLE proteins and derivatives thereof, TLE nucleic acids encoding the foregoing, and proteins comprising toporythmic or other protein domains that interact with TLE proteins (e.g., protein components of multiprotein complexes containing TLE protein(s) (see Section 5.11). "Toporythmic" genes, as used herein, shall mean the genes Notch, Delta, Serrate, Enhancer of split, and deltex, as well as other members of the Delta/Serrate family which may be identified by virtue of sequence homology or genetic interaction, and, more generally, members of the "Notch cascade" or the "Notch group" of genes, which are identified by molecular interactions (e.g., binding in vitro) or genetic interactions (as detected phenotypically, e.g., in Drosophila).

In a particular embodiment, a Therapeutic comprises a sequence selected from among the sequences of four distinct human homologs of the Drosophila TLE gene, and sequences of their unique encoded TLE proteins. As described by way of example in Section 6, the TLE proteins and their Drosophila homolog contain a motif implicated in nuclear/cytoplasmic protein transport, called the casein kinase II site/cdc2 kinase site/nuclear localization sequence motif (CcN motif). We show that the TLE proteins are found in the nucleus, consistent with a function as nuclear effector molecules, and that the TLE genes are broadly expressed in adult tissues, suggesting a widespread physiological role for their encoded proteins.

In specific embodiments, Therapeutics are TLE protein derivatives and analogs of the invention which are functionally active, or which comprise one or more domains of a TLE protein, preferably a human TLE protein, including but not limited to the "Q domain," "GP domain," "CcN domain," "SP domain," "WD-40 domain," or a WD-40 repeat, casein kinase II (CK II) site, cdc2 kinase (cdc2) site, or nuclear localization sequence motif, or consensus sequences for any of the foregoing, or any combination of the foregoing.

Examples of various Therapeutics of the invention are described in detail infra, in Sections 5.7 through 5.12.

Disorders of cell fate, in particular precancerous conditions such as metaplasia and dysplasia, and hyperproliferative (e.g., cancer) or hypoproliferative disorders, involving aberrant or undesirable levels of expression or activity of a TLE protein can be diagnosed by detecting such levels, as described more fully infra.

For clarity of disclosure, and not by way of limitation, the detailed description of the invention is divided into the following subsections:

(i) Therapeutic Uses;

(ii) Prophylactic Uses;

(iii) Demonstration of Therapeutic or Prophylactic Utility;

(iv) Therapeutic/Prophylactic Administration and Compositions;

(v) Antisense Regulation of TLE Expression;

(vi) Diagnostic Utility;

(vii) TLE Nucleic Acids;

(viii) Recombinant Production of Protein Therapeutics;

(ix) Derivatives and Analogs of TLE Proteins and TLE Ligands;

(x) Assays of TLE Proteins, Derivatives and Analogs;

(xi) Binding Partners of TLE Promins; and (xii) Antibodies to TLE Proteins and Derivatives Thereof.

5.1. THERAPEUTIC USES

As stated supra, the Antagonist Therapeutics of the invention are those Therapeutics which antagonize, or inhibit, a TLE protein function. Such Antagonist Therapeutics are most preferably identified by use of known convenient in vitro assays, e.g., based on their ability to inhibit binding of TLE to other proteins (see Sections 5.11 and 7 herein), or inhibit any known TLE function as assayed in vitro, although genetic assays (e.g., in Drosophila) may also be employed. In a preferred embodiment, the Antagonist Therapeutic is a protein or derivative thereof comprising a functionally active fragment such as a fragment of a TLE protein which binds to another promin. In specific embodiments, such an Antagonist Therapeutic may be a protein comprising the WD-40 domain, or an antibody thereto, or an analog/competitive inhibitor of a TLE signal-transducing function, a nucleic acid capable of expressing one of the foregoing proteins, or a TLE antisense nucleic acid (see Section 5.5 herein). It should be noted that in certain instances, a TLE fragment with binding activity (or other presumed Antagonist Therapeutics) may alternatively act as an Agonist Therapeutic, depending on the developmental history of the tissue being exposed to the Therapeutic; preferably, suitable in vitro or in vivo assays, as described infra, should be utilized to determine the effect of a specific Therapeutic and whether its administration is indicated for treatment of the affected tissue.

In another embodiment of the invention, a nucleic acid containing a portion of a TLE gene is used, as an Antagonist Therapeutic, to promote TLE inactivation by homologous recombination (Koller and Smithies, 1989, Proc. Natl. Acad. Sci. USA 86:8932–8935; Zijlstra et al., 1989, Nature 342:435–438).

The Agonist Therapeutics of the invention, as described supra, promote TLE function. Such Agonist Therapeutics can include but are not limited to TLE proteins and derivatives and analogs of the invention which comprise one or more domains of a TLE protein or which are functionally active, i.e., they are capable of displaying one or more known functional activities associated with a full-length (wild-type) TLE protein. Such functional activities include but are not limited to antigenicity [ability to bind (or compete with a TLE protein for binding) to an anti-TLE protein antibody], immunogenicity (ability to generate antibody which binds to a TLE protein, ability to bind (or compete with a TLE protein for binding) to possibly Notch or other toporythmic proteins or fragments thereof, ability to bind (or compete with a TLE protein for binding) to a receptor or ligand for a TLE protein. Domains of a TLE protein (see Section 6) include but are not limited to the "Q domain," "GP domain," "CcN domain," "SP domain," "WD-40 domain," or a WD-40 repeat, casein kinase II (CK II) site, cdc2 kinase (cdc2) site, or nuclear localization sequence motif, or consensus sequences for any of the foregoing, or any combination of the foregoing.

Further descriptions and sources of Therapeutics of the inventions are found in Sections 5.4 through 5.12 herein.

The Agonist and Antagonist Therapeutics of the invention have therapeutic utility for disorders of cell fate. The Agonist Therapeutics are administered therapeutically (including prophylactically): (1) in diseases or disorders involving an absence or decreased (relative to normal, or desired) levels of TLE function, for example, in patients where TLE protein is lacking, genetically defective, biologically inactive or underactive, or underexpressed; and (2) in diseases or disorders wherein in vitro (or in vivo) assays (see infra) indicate the utility of TLE agonist administration. The absence or decreased levels in TLE function can be readily detected, e.g., by obtaining a patient tissue sample (e.g., from biopsy tissue) and assaying it in vitro for protein levels, structure and/or activity of the expressed TLE protein. Many methods standard in the art can be thus employed, including but not limited to immunoassays to detect and/or visualize TLE protein (e.g., Western blot, immunoprecipitation followed by sodium dodecyl sulfate polyacrylamide gel electrophoresis, immunocytochemistry, etc.; see also those assays listed in Section 5.6, infra), and/or hybridization assays to detect TLE expression by detecting and/or visualizing TLE mRNA (e.g., TLE assays, dot blots, in situ hybridization, etc.)

In vitro assays which can be used to determine whether administration of a specific Agonist Therapeutic or Antagonist Therapeutic is indicated, include in vitro cell culture assays in which a patient tissue sample is grown in culture, and exposed to or otherwise administered a Therapeutic, and the effect of such Therapeutic upon the tissue sample is observed. In one embodiment, where the patient has a malignancy, a sample of cells from such malignancy is plated out or grown in culture, and the cells are then exposed to a Therapeutic. A Therapeutic which inhibits survival or growth of the malignant cells (e.g., by promoting terminal differentiation) is selected for therapeutic use in vivo. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, etc. In a specific aspect, the malignant cell cultures are separately exposed to (1) an Agonist Therapeutic, and (2) an Antagonist Therapeutic; the result of the assay can indicate which type of Therapeutic has therapeutic efficacy.

In another embodiment, a Therapeutic is indicated for use which exhibits the desired effect, inhibition or promotion of cell growth, upon a patient cell sample from tissue having or suspected of having a hyper- or hypoproliferative disorder, respectively. Such hyper- or hypoproliferative disorders include but are not limited to those described in Sections 5.1.1 through 5.1.3 infra.

In another specific embodiment, a Therapeutic is indicated for use in treating nerve injury or a nervous system degenerative disorder (see Section 5.1.2) which exhibits in vitro promotion of nerve regeneration/neurite extension from nerve cells of the affected patient type.

In various specific embodiments, in vitro assays can be carried out with representative cells of cell types involved in a patient's disorder, to determine if a Therapeutic has a desired effect upon such cell types.

In another embodiment, cells of a patient tissue sample suspected of being pre-neoplastic are similarly plated out or grown in vitro, and exposed to a Therapeutic. The Therapeutic which results in a cell phenotype that is more normal (i.e., less representative of a pre-neoplastic state, neoplastic state, malignant state, or transformed phenotype) is selected for therapeutic use. Many assays standard in the art can be used to assess whether a pre-neoplastic state, neoplastic state, or a transformed or malignant phenotype, is present (see Section 5.2.1). For example, characteristics associated with a transformed phenotype (a set of in vitro characteristics associated with a tumorigenic ability in vivo) include a more rounded cell morphology, looser substratum attachment, loss of contact inhibition, loss of anchorage dependence, release of proteases such as plasminogen activator, increased sugar transport, decreased serum requirement, expression of fetal antigens, disappearance of the 250,000 dalton surface protein, etc. (see Luria et al., 1978, General Virology, 3d Ed., John Wiley & Sons, New York pp. 436–446).

In other specific embodiments, the in vitro assays described supra can be carried out using a cell line, rather than a cell sample derived from the specific patient to be treated, in which the cell line is derived from or displays characteristic(s) associated with the malignant, neoplastic or pre-neoplastic disorder desired to be treated or prevented, or is derived from the neural or other cell type upon which an effect is desired, according to the present invention.

The Antagonist Therapeutics are administered therapeutically (including prophylactically): (1) in diseases or disorders involving increased (relative to normal, or desired) levels of TLE function, for example, where a TLE protein is overexpressed or overactive; and (2) in diseases or disorders wherein in vitro (or in vivo) assays indicate the utility of TLE antagonist administration. The increased levels of TLE function can be readily detected by methods such as those described above, by quantifying protein and/or RNA. In vitro assays with cells of patient tissue sample or the appropriate cell line or cell type, to determine therapeutic utility, can be carried out as described above.

5.1.1. MALIGNANCIES

Malignant and pre-neoplastic conditions which can be tested as described supra for efficacy of intervention with Antagonist or Agonist Therapeutics, and which can be treated upon thus observing an indication of therapeutic utility, include but are not limited to those described below in Sections 5.1.1 and 5.2.1.

Malignancies and related disorders, cells of which type can be tested in vitro (and/or in vivo), and upon observing the appropriate assay result, treated according to the present invention, include but are not limited to those listed in Table 1 (for a review of such disorders, see Fishman et al., 1985. Medicine, 2d Ed., J. B. Lippincott Co., Philadelphia):

TABLE 1

MALIGNANCIES AND RELATED DISORDERS

Leukemia
  acute leukemia
    acute lymphocytic leukemia
    acute myelocytic leukemia
      myeloblastic
      promyelocytic
      myelomonocytic
      monocytic
      erythroleukemia
  chronic leukemia
    chronic myelocytic (granulocytic) leukemia
    chronic lymphocytic leukemia
Polycythemia vera
Lymphoma
  Hodgkin's disease
  non-Hodgkin's disease
Multiple myeloma
Waldenström's macroglobulinemia
Heavy chain disease
Solid tumors
    sarcomas and carcinomas
      fibrosarcoma
      myxosarcoma
      liposarcoma
      chondrosarcoma
      osteogenic sarcoma
      chordoma
      angiosarcoma
      endotheliosarcoma
      lymphangiosarcoma
      lymphangioendotheliosarcoma
      synovioma
      mesothelioma

TABLE 1-continued

MALIGNANCIES AND RELATED DISORDERS

Ewing's tumor
      leiomyosarcoma
      rhabdomyosarcoma
      colon carcinoma
      pancreatic cancer
      breast cancer
      ovarian cancer
      prostate cancer
      squamous cell carcinoma
      basal cell carcinoma
      adenocarcinoma
      sweat gland carcinoma
      sebaceous gland carcinoma
      papillary carcinoma
      papillary adenocarcinomas
      cystadenocarcinoma
      medullary carcinoma
      bronchogenic carcinoma
      renal cell carcinoma
      hepatoma
      bile duct carcinoma
      choriocarcinoma
      seminoma
      embryonal carcinoma
      Wilms' tumor
      cervical cancer
      testicular tumor
      lung carcinoma
      small cell lung carcinoma
      bladder carcinoma
      epithelial carcinoma
      glioma
      astrocytoma
      medulloblastoma
      craniopharyngioma
      ependymoma
      pinealoma
      hemangioblastoma
      acoustic neuroma
      oligodendroglioma
      menangioma
      melanoma
      neuroblastoma
      retinoblastoma In specific embodiments, malignancy or dysproliferative changes (such as metaplasias and dysplasias) are treated or prevented in epithelial tissues such as those in the cervix, esophagus, and lung.

5.1.2. NERVOUS SYSTEM DISORDERS

Nervous system disorders, involving cell types which can be tested as described supra for efficacy of intervention with Antagonist or Agonist Therapeutics, and which can be treated upon thus observing an indication of therapeutic utility, include but are not limited to nervous system injuries, and diseases or disorders which result in either a disconnection of axons, a diminution or degeneration of neurons, or demyelination. Nervous system lesions which may be treated in a patient (including human and non-human mammalian patients) according to the invention include but are not limited to the following lesions of either the central (including spinal cord, brain) or peripheral nervous systems:

(i) traumatic lesions, including lesions caused by physical injury or associated with surgery, for example, lesions which sever a portion of the nervous system, or compression injuries;

(ii) ischemic lesions, in which a lack of oxygen in a portion of the nervous system results in neuronal injury or death, including cerebral infarction or ischemia, or spinal cord infarction or ischemia;

(iii) malignant lesions, in which a portion of the nervous system is destroyed or injured by malignant tissue which is either a nervous system associated malignancy or a malignancy derived from non-nervous system tissue;

(iv) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis;

(v) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis;

(vi) lesions associated with nutritional diseases or disorders, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration;

(vii) neurological lesions associated with systemic diseases including but not limited to diabetes (diabetic neuropathy, Bell's palsy), systemic lupus erythematosus, carcinoma, or sarcoidosis;

(viii) lesions caused by toxic substances including alcohol, lead, or particular neurotoxins; and (ix) demyelinated lesions in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontinc myelinolysis.

Therapeutics which are useful according to the invention for treatment of a nervous system disorder may be selected by testing for biological activity in promoting the survival or differentiation of neurons (see also Section 5.1). For example, and not by way of limitation, Therapeutics which elicit any of the following effects may be useful according to the invention:

(i) increased survival time of neurons in culture;

(ii) increased sprouting of neurons in culture or in vivo;

(iii) increased production of a neuron-associated molecule in culture or in vivo, e.g., choline acetyltransferase or acetylcholinesterase with respect to motor neurons; or (iv) decreased symptoms of neuron dysfunction in vivo.

Such effects may be measured by any method known in the art. In preferred, non-limiting embodiments, increased survival of neurons may be measured by the method set forth in Arakawa et al. (1990, J. Neurosci. 10:3507–3515); increased sprouting of neurons may be detected by methods set forth in Pestronk et al. (1980, Exp. Neurol. 70:65–82) or Brown et al. (1981, Ann. Rev. Neurosci. 4:17–42); increased production of neuron-associated molecules may be measured by bioassay, enzymatic assay, antibody binding, Northern blot assay, etc., depending on the molecule to be measured; and motor neuron dysfunction may be measured by assessing the physical manifestation of motor neuron disorder, e.g., weakness, motor neuron conduction velocity, or functional disability.

In a specific embodiments, motor neuron disorders that may be treated according to the invention include but are not limited to disorders such as infarction, infection, exposure to toxin, trauma, surgical damage, degenerative disease or malignancy that may affect motor neurons as well as other components of the nervous system, as well as disorders that selectively affect neurons such as amyotrophic lateral sclerosis, and including but not limited to progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

5.1.3. TISSUE REPAIR AND REGENERATION

In another embodiment of the invention, a Therapeutic of the invention is used for promotion of tissue regeneration and repair, including but not limited to treatment of benign dysproliferative disorders. Specific embodiments are directed to treatment of cirrhosis of the liver (a condition in which scarring has overtaken normal liver regeneration processes), treatment of keloid (hypertrophic scar) formation (disfiguring of the skin in which the scarring process interferes with normal renewal), psoriasis (a common skin condition characterized by excessive proliferation of the skin and delay in proper cell fate determination), and baldness (a condition in which terminally differentiated hair follicles (a tissue rich in Notch) fail to function properly).

5.2. PROPHYLACTIC USES

5.2.1. MALIGNANCIES

The Therapeutics of the invention can be administered to prevent progression to a neoplastic or malignant state, including but not limited to those disorders listed in Table 1. Such administration is indicated where the Therapeutic is shown in assays, as described supra, to have utility for treatment or prevention of such disorder. Such prophylactic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, *Basic Pathology*, 2d Ed., W. B. Saunders Co., Philadelphia, pp. 68–79.) Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a patient, can indicate the desirability of prophylactic/therapeutic administration of a Therapeutic of the invention. As mentioned supra, such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84–90 for characteristics associated with a transformed or malignant phenotype).

In a specific embodiment, leukoplakia, a benign-appearing hyperplastic or dysplastic lesion of the epithelium, or Bowen's disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia)) is indicative of the desirability of prophylactic intervention.

In other embodiments, a patient which exhibits one or more of the following predisposing factors for malignancy is treated by administration of an effective amount of a Therapeutic: a chromosomal translocation associated with a malignancy (e.g., the Philadelphia chromosome for chronic myelogenous leukemia, t(14;18) for follicular lymphoma, etc.), familial polyposis or Gardner's syndrome (possible forerunners of colon cancer), benign monoclonal gammopathy (a possible forerunner of multiple myeloma), and a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, Basic Pathology, 2d Ed., W. B. Saunders Co., Philadelphia, pp. 112–113) etc.)

5.2.2. OTHER DISORDERS

In other embodiments, a Therapeutic of the invention can be administered to prevent a nervous system disorder described in Section 5.1.2, or other disorder (e.g., liver cirrhosis, psoriasis, keloids, baldness) described in Section 5.1.3.

5.3. DEMONSTRATION OF THERAPEUTIC OR PROPHYLACTIC UTILITY

The Therapeutics of the invention can be tested in vivo for the desired therapeutic or prophylactic activity. For example, such compounds can be tested in suitable animal model systems prior to testing in humans, including but not limited to rats, mice, chicken, cows, monkeys, rabbits, etc. For in vivo testing, prior to administration to humans, any animal model system known in the art may be used.

5.4. THERAPEUTIC/PROPHYLACTIC ADMINISTRATION AND COMPOSITIONS

The invention provides methods of treatment (and prophylaxis) by administration to a subject of an effective amount of a Therapeutic of the invention. In a preferred aspect, the Therapeutic is substantially purified. The subject is preferably an animal, including but not limited to animals such as cows, pigs, chickens, etc., and is preferably a mammal, and most preferably human.

In a preferred aspect, the Therapeutic is a human protein. In one such embodiment, a composition for therapeutic or prophylactic use according to the invention comprises one or more human TLE proteins selected from among the TLE sequences encoded by the cDNAs TLE 1, TLE 2, TLE 3 or, in part, by TLE 4 (see Section 6). In a specific embodiment, the therapeutic composition comprises more than one different human TLE protein.

Since TLE proteins are predominantly found in the nucleus, a Therapeutic of the invention should be administered so as to allow cellular uptake into the cell and preferably, delivery to the nucleus. For example, in a specific embodiment, a Therapeutic is preferably delivered intracellularly (e.g., by expression from a nucleic acid vector, or by linkage to a Delta protein capable of binding to Notch followed by binding and internalization, or by receptor-mediated mechanisms). In a particular embodiment, administration of a Therapeutic into a Notch-expressing cell is accomplished by linkage of the Therapeutic to a Delta (or other toporythmic) protein or portion thereof capable of mediating binding to Notch. Contact of a Notch-expressing cell with the linked Therapeutic results in binding of the linked Therapeutic via its Delta portion to Notch on the surface of the cell, followed by uptake of the linked Therapeutic into the Notch-expressing cell.

In a specific embodiment where the Therapeutic is a nucleic acid encoding a protein Therapeutic, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864–1868), etc. Alternatively, a nucleic acid Therapeutic can be introduced intracellularly and incorporated within host cell DNA for expression, by homologous recombination.

Various delivery systems are known and can be used to administer a Therapeutic of the invention, e.g., encapsulation in liposomes, microparticles, microcapsules, expression by recombinant cells, receptor-mediated endocytosis (see, e.g., Wu and Wu, 1987, J. Biol. Chem. 262:4429–4432), construction of a Therapeutic nucleic acid as part of a retroviral or other vector, etc. Methods of introduction include but are not limited to intradermal, intramuscular, intraperitoneal, intravenous, subcutaneous, intranasal, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In specific embodiments directed to treatment or prevention of particular disorders, preferably the following forms of administration are used:

| Disorder | Preferred Forms of Administration |
| --- | --- |
| Cervical cancer | Topical |
| Gastrointestinal cancer | Oral; intravenous |
| Lung cancer | Inhaled; intravenous |
| Leukemia | Intravenous; extracorporeal |
| Metastatic carcinomas | Intravenous; oral |
| Brain cancer | Targeted; intravenous; intrathecal |
| Liver cirrhosis | Oral; intravenous |
| Psoriasis | Topical |
| Keloids | Topical |
| Baldness | Topical |
| Spinal cord injury | Targeted; intravenous; intrathecal |
| Parkinson's disease | Targeted; intravenous; intrathecal |
| Motor neuron disease | Targeted; intravenous; intrathecal |
| Alzheimer's disease | Targeted; intravenous; intrathecal |

The present invention also provides pharmaceutical compositions. Such compositions comprise a therapeutically effective amount of a Therapeutic, and a pharmaceutically acceptable carrier or excipient. Such a carrier includes but is not limited to saline, buffered saline, dextrose, water, glycerol, ethanol, and combinations thereof. The carrier and composition can be sterile. The formulation should suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

5.5. ANTISENSE REGULATION OF TLE EXPRESSION

The present invention provides the therapeutic or prophylactic use of nucleic acids of at least six nucleotides that are antisense to a gene or cDNA encoding a TLE protein or a portion thereof. "Antisense" as used herein refers to a nucleic acid capable of hybridizing to a portion of a TLE RNA (preferably mRNA) by virtue of some sequence complementarity. Such antisense nucleic acids have utility as Antagonist Therapeutics of the invention, and can be used in the treatment or prevention of disorders as described supra in Section 5.1 and its subsections.

The antisense nucleic acids of the invention can be oligonucleotides that are double-stranded or single-stranded, RNA or DNA or a modification or derivative thereof, which can be directly administered to a cell, or which can be produced intracellularly by transcription of exogenous, introduced sequences.

In a specific embodiment, the TLE antisense nucleic acids provided by the instant invention can be used for the treatment of tumors or other disorders, the cells of which tumor type or disorder can be demonstrated (in vitro or in vivo) to express the TLE gene. Such demonstration can be by detection of TLE RNA or of TLE protein.

The invention further provides pharmaceutical compositions comprising an effective amount of the TLE antisense nucleic acids of the invention in a pharmaceutically acceptable carrier, as described supra in Section 5.4. Methods for treatment and prevention of disorders (such as those described in Sections 5.1 and 5.2) comprising administering the pharmaceutical compositions of the invention are also provided.

In another embodiment, the invention is directed to methods for inhibiting the expression of a TLE nucleic acid sequence in a prokaryotic or eukaryotic cell, comprising providing the cell with an effective amount of a composition comprising an antisense TLE nucleic acid of the invention.

In an alternative embodiment of the invention, nucleic acids antisense to a nucleic acid encoding a protein or fragment that binds to a TLE protein, are envisioned as Therapeutics.

TLE antisense nucleic acids and their uses are described in detail below.

5.5.1. TLE ANTISENSE NUCLEIC ACIDS

The TLE antisense nucleic acids are of at least six nucleotides and are preferably oligonucleotides (ranging from 6 to about 50 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO 88/09810, published Dec. 15, 1988) or blood-brain barrier (see, e.g., PCT Publication No. WO 89/10134, published Apr. 25, 1988), hybridization-triggered cleavage agents (see, e.g., Krol et al., 1988, BioTechniques 6:958–976) or intercalating agents (see, e.g., Zon, 1988, Pharm. Res. 5:539–549).

In a preferred aspect of the invention, a TLE antisense oligonucleotide is provided, preferably of single-stranded DNA. In a most preferred aspect, such an oligonucleotide comprises a sequence antisense to the sequence encoding a WD-40 domain of a TLE protein, most preferably, of a human TLE protein. The oligonucleotide may be modified at any position on its structure with substituents generally known in the art.

The TLE antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

In another embodiment, the oligonucleotide comprises at least one modified sugar moiety selected from the group including but not limited to arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641).

The oligonucleotide may be conjugated to another molecule, e.g., a peptide, hybridization triggered cross-linking agent, transport agent, hybridization-triggered cleavage agent, etc.

Oligonucleotides of the invention may be synthesized by standard methods known in the art, e.g. by use of an automated DNA synthesizer (such as are commercially available from Biosearch, Applied Biosystems, etc.). As examples, phosphorothioate oligos may be synthesized by the method of Stein et al. (1988, Nucl. Acids Res. 16:3209), methylphosphonate oligos can be prepared by use of controlled pore glass polymer supports (Sarin et al., 1988, Proc. Natl. Acad. Sci. U.S.A. 85:7448–7451), etc.

In a specific embodiment, the TLE antisense oligonucleotide comprises catalytic RNA, or a ribozyme (see, e.g., PCT International Publication WO 90/11364, published Oct. 4, 1990; Sarver et at., 1990, Science 247:1222–1225). In another embodiment, the oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

In an alternative embodiment, the TLE antisense nucleic acid of the invention is produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the TLE antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the TLE antisense RNA can be by any promoter known in the art to act in mammalian, preferably human, cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc.

The antisense nucleic acids of the invention comprise a sequence complementary to at least a portion of an RNA transcript of a TLE gene, preferably a human TLE gene.

However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded TLE antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a TLE RNA it may contain and still form a stable duplex (or triplex, as the case may be). One skilled in the art can ascertain a tolerable degree of mismatch by use of standard procedures to determine the melting point of the hybridized complex.

5.5.2. THERAPEUTIC UTILITY OF TLE ANTISENSE NUCLEIC ACIDS

The TLE antisense nucleic acids can be used to treat (or prevent) malignancies, of a cell type which has been shown to express TLE RNA. Malignant, neoplastic, and pre-neoplastic cells which can be tested for such expression include but are not limited to those described supra in Sections 5.1.1 and 5.2.1. In a preferred embodiment, a single-stranded DNA antisense TLE oligonucleotide is used.

Malignant (particularly, tumor) cell types which express TLE RNA can be identified by various methods known in the art. Such methods include but are not limited to hybridization with a TLE-specific nucleic acid (e.g. by Northern hybridization, dot blot hybridization, in situ hybridization), observing the ability of RNA from the cell type to be translated in vitro into TLE protein, etc. In a preferred aspect, primary tumor tissue from a patient can be assayed for TLE protein expression prior to treatment.

Pharmaceutical compositions of the invention (see Section 5.1.4), comprising an effective amount of a TLE antisense nucleic acid in a pharmaceutically acceptable carrier, can be administered to a patient having a malignancy which is of a type that expresses TLE RNA.

The amount of TLE antisense nucleic acid which will be effective in the treatment of a particular disorder or condition will depend on the nature of the disorder or condition, and can be determined by standard clinical techniques. Where possible, it is desirable to determine the antisense cytotoxicity of the tumor type to be treated in vitro, and then in useful animal model systems prior to testing and use in humans.

In a specific embodiment, pharmaceutical compositions comprising TLE antisense nucleic acids are administered via liposomes, microparticles, or microcapsules. In various embodiments of the invention, it may be useful to use such compositions to achieve sustained release of the TLE antisense nucleic acids. In a specific embodiment, it may be desirable to utilize liposomes targeted via antibodies to specific identifiable tumor antigens (Leonetti et al., 1990, Proc. Natl. Acad. Sci. U.S.A. 87:2448–2451; Renneisen et al., 1990, J. Biol. Chem. 265:16337–16342).

5.6. DIAGNOSTIC UTILITY

TLE proteins, analogues, derivatives, and subsequences thereof, TLE nucleic acids (and sequences complementary thereto), anti-TLE protein antibodies, and other proteins and derivatives and analogs thereof which interact with TLE proteins, and inhibitors of such TLE-protein interactions, have uses in diagnostics. Such molecules can be used in assays, such as immunoassays, to detect, prognose, diagnose, or monitor various conditions, diseases, and disorders affecting TLE expression, or monitor the treatment thereof. In particular, such an immunoassay is carried out by a method comprising contacting a sample derived from a patient, after lysis of any cells contained in the patient sample, with an anti-TLE protein antibody under conditions such that immunospecific binding can occur, and detecting or measuring the amount of any immunospecific binding by the antibody. In a specific embodiment, antibody to TLE protein(s) can be used to assay in a patient tissue or serum sample for the presence of TLE protein(s) where an aberrant level of TLE protein(s) is an indication of a diseased condition.

The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few.

TLE genes and related nucleic acid sequences and subsequences, including complementary sequences, and gene sequences of TLE binding partners, can also be used in hybridization assays. TLE nucleic acid sequences, or subsequences thereof comprising about at least 8 nucleotides, can be used as hybridization probes. Hybridization assays can be used to detect, prognose, diagnose, or monitor conditions, disorders, or disease states associated with aberrant changes in TLE expression and/or activity as described supra. In particular, such a hybridization assay is carried out by a method comprising contacting a sample containing nucleic acid with a nucleic acid probe capable of hybridizing to TLE DNA or RNA, under conditions such that hybridization can occur, and detecting or measuring any resulting hybridization.

5.7. TLE NUCLEIC ACIDS

Therapeutics of the invention which are TLE nucleic acids or TLE antisense nucleic acids, as well as nucleic acids encoding protein Therapeutics, include those described below, which can be obtained by methods known in the art, and in particular, as described below.

In particular aspects, the invention provides amino acid sequences of a TLE protein, preferably a human TLE protein, and fragments and derivatives thereof which comprise an antigenic determinant (i.e., can be recognized by an antibody) or which are functionally active, as well as nucleic acid sequences encoding the foregoing. "Functionally active" material as used herein refers to that material displaying one or more known functional activities associated with a full-length (wild-type) TLE protein product, e.g., binding to any TLE ligand, antigenicity (binding to an anti-TLE protein antibody), immunogenicity (ability to generate anti-TLE protein antibody), nuclear localization, etc.

In specific embodiments, the invention provides fragments of a TLE protein consisting of at least 50 amino acids, or of at least 75 amino acids. In other embodiments, the proteins comprise or consist essentially of a Q domain, GP domain, CcN domain, SP domain, WD-40 domain, one or more WD-40 repeats or a consensus WD-40 repeat (FIG. 6), NLS, CK II, or cdc2 site, or any combination of the foregoing, of a TLE protein. Fragments, or proteins comprising fragments, lacking some or all of a domain or motif of a TLE protein are also provided. Nucleic acids encoding the foregoing are provided.

In other specific embodiments, the invention provides nucleotide sequences and subsequences of a TLE gene, preferably a human TLE gene, consisting of at least 25 nucleotides, at least 50 nucleotides, at least 150 nucleotides, or at least 200 nucleotides. Nucleic acids encoding the proteins and protein fragments described above are provided, as well as nucleic acids complementary to and capable of hybridizing to such nucleic acids. In preferred aspects, the TLE nucleic acids are human nucleic acids, in particular, comprising one of the four human TLE sequences described in Section 6. Thus, in specific embodiments, human TLE nucleic acids comprise the TLE 1, TLE 2, TLE 3, or TLE 4 cDNAs or a portion thereof. In other specific aspects, Therapeutics are provided which are nucleic acids comprising a sequence complementary to at least 10, 25, 50, 100, or 200 nucleotides or the entire coding region of a TLE gene, preferably a human TLE gene. In other embodiments, the TLE nucleic acid and/or its encoded protein is a Drosophila molecule, and has, for example, the sequence reported by Hartley et al. (1988, Cell 55:785–795).

As is readily apparent, as used herein, a "nucleic acid encoding a fragment or portion of a TLE protein" shall be construed as referring to a nucleic acid encoding only the recited fragment or portion of the TLE protein and not other portions of the TLE protein.

In a preferred, but not limiting, aspect of the invention, a human TLE DNA sequence can be cloned and sequenced by the method described in Section 6, infra.

In another preferred aspect, PCR is used to amplify the desired sequence in the library, prior to selection. Oligonucleotide primers representing known TLE protein sequences can be used as primers in PCR. In a preferred aspect, the oligonucleotide primers encode at least part of the conserved segments of strong homology between Drosophila and human TLE proteins (e.g., in the Q domain, CcN domain, or WD-40 domain). The synthetic oligonucleotides may be utilized as primers to amplify by PCR sequences from a source (RNA or DNA), preferably a cDNA library, of potential interest. PCR can be carried out, e.g., by use of a Perkin-Elmer Cetus thermal cycler and Taq polymerase (Gene Amp™). The DNA being amplified can include mRNA or cDNA or genomic DNA. One can choose to synthesize several different degenerate primers, for use in the PCR reactions. It is also possible to vary the stringency of hybridization conditions used in priming the PCR reactions, to allow for greater or lesser degrees of nucleotide sequence similarity between the known TLE nucleotide sequence and the nucleic acid homolog being isolated. After successful amplification of a segment of a TLE gene homolog, that segment may be molecularly cloned and sequenced, and utilized as a probe to isolate a complete cDNA or genomic clone. This, in turn, will permit the determination of the gene's complete nucleotide sequence, the analysis of its expression, and the production of its protein product for functional analysis, as described infra. In this fashion, it is also possible that additional human genes encoding TLE proteins may be identified.

The above-methods are not meant to limit the following general description of methods by which clones of TLE genes may be obtained.

Any eukaryotic (preferably, human) cell potentially can serve as the nucleic acid source for the molecular cloning of the TLE gene. The DNA may be obtained by standard procedures known in the art from cloned DNA (e.g., a DNA "library"), by chemical synthesis, by cDNA cloning, or by the cloning of genomic DNA, or fragments thereof, purified from the desired cell (see, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will lack introns and will contain only exon sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired gene may be accomplished in a number of ways. For example, if an amount of a portion of a TLE (of any species) gene or its specific RNA, or a fragment thereof, e.g., a Q or WD-40 domain (see Section 5.9.1), is available and can be purified, or synthesized, and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). Those DNA fragments with substantial homology to the probe will hybridize. It is also possible to identify the appropriate fragment by restriction enzyme digestion(s) and comparison of fragment sizes with those expected according to a known restriction map, either available or deduced from a known nucleotide sequence. Further selection can be carried out on the basis of the properties of the gene. Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, binding activity, or antigenic properties as known for a TLE protein. By use of an antibody to a TLE protein, the TLE protein may be identified by binding of labeled antibody to the putatively TLE protein synthesizing clones, in an ELISA (enzyme-linked immunosorbent assay)-type procedure.

The TLE gene can also be identified by mRNA selection by nucleic acid hybridization followed by in vitro translation. In this procedure, fragments are used to isolate complementary mRNAs by hybridization. Such DNA fragments may represent available, purified TLE DNA of human or of another species (e.g., Drosophila). Immunoprecipitation analysis or functional assays (e.g., binding to a receptor or ligand; see infra) of the in vitro translation products of the isolated products of the isolated mRNAs identifies the mRNA and, therefore, the complementary DNA fragments that contain the desired sequences. In addition, specific mRNAs may be selected by adsorption of polysomes isolated from cells to immobilized antibodies specifically directed against a TLE protein. A radiolabelled TLE cDNA can be synthesized using the selected mRNA (from the adsorbed polysomes) as a template. The radiolabelled mRNA or cDNA may then be used as a probe to identify the TLE DNA fragments from among other genomic DNA fragments.

Alternatives to isolating the TLE genomic DNA include, but are not limited to, chemically synthesizing the gene sequence itself from a known sequence or making cDNA to the mRNA which encodes a TLE protein. For example, RNA for cDNA cloning of the human TLE gene can be isolated from human cells which express a TLE protein (see Section 6.1.3). Other methods are possible and within the scope of the invention.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as PBR322 or pUC plasmid derivatives. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and TLE gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionation, can be done before insertion into the cloning vector.

In specific embodiments, transformation of host cells with recombinant DNA molecules that incorporate the isolated TLE gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The TLE nucleotide sequences provided by the present invention include those nucleotide sequences encoding substantially the same amino acid sequences as found in a native TLE protein, and those encoded amino acid sequences with functionally equivalent amino acids, all as described in Section 5.9 infra for TLE derivatives.

5.8. RECOMBINANT PRODUCTION OF PROTEIN THERAPEUTICS

The nucleic acid coding for a protein Therapeutic of the invention can be inserted into an appropriate expression vector, i.e. , a vector which contains the necessary elements for the transcription and translation of the inserted protein-coding sequence. The necessary transcriptional and translational signals can also be supplied by the native TLE gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA, or cosmid DNA. The expression elements of vectors vary in their strengths and specificities. Depending on the host-vector system utilized, any one of a number of suitable transcription and translation elements may be used. In a specific embodiment, a chimeric protein comprising the nuclear localization signal or other motif or domain of a human TLE protein is expressed. In other specific embodiments, a full-length human TLE cDNA is expressed, or a sequence encoding a functionally active portion of a human TLE protein. In yet another embodiment, a fragment of a human TLE protein comprising a domain of the protein, or other derivative, or analog of a human TLE protein is expressed.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of a nucleic acid sequence encoding a TLE protein or peptide fragment may be regulated by a second nucleic acid sequence so that the TLE protein or peptide is expressed in a host transformed with the recombinant DNA molecule. For example, expression of a TLE protein may be controlled by any promoter/enhancer element known in the art. Promoters which may be used to control TLE gene expression include, but are not limited to, the SV40 early promoter region (Bernoist and Chambon, 1981, Nature 290:304–310), the promoter contained in the 3' long terminal repeat of Rous sarcoma virus (Yarnamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase (Villa-Kamaroff et al., 1978, Proc. Natl. Acad. Sci. U.S.A. 75:3727–3731), tac (DeBoer et al., 1983, Proc. Natl. Acad. Sci. U.S.A. 80:21–25), $\lambda P_L$, or trc promoters; see also "Useful proteins from recombinant bacteria" in Scientific American, 1980, 242:74–94; plant expression vectors comprising the nopaline synthetase promoter region or the cauliflower mosaic virus 35S RNA promoter (Gardner et al. , 1981, Nucl. Acids Res. 9:2871), and the promoter of the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et at., 1984, Cell 38:639–646; Ornitz et at., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et at., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et at., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58; alpha 1-antitrypsin gene control region which is active in the liver (Kelsey etal., 1987, Genes and Devel. 1:161–171), beta-globin gene control region which is active in myeloid cells (Mogram et al., 1985, Nature 315:338–340; Kollias et al., 1986, Cell 46:89–94; myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et at., 1986, Science 234: 1372–1378).

Expression vectors containing TLE gene inserts can be identified by three general approaches: (a) nucleic acid hybridization, (b) presence or absence of "marker" gene functions, and (c) expression of inserted sequences. In the first approach, the presence of a foreign gene inserted in an expression vector can be detected by nucleic acid hybridization using probes comprising sequences that are homologous to an inserted TLE gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the TLE gene is inserted within the marker gene sequence of the vector, recombinants containing the E(spl) insert can be identified by the absence of the marker gene function. In the third approach, recombinant expression vectors can be identified by assaying the foreign gene product expressed by the recombinant. Such assays can be based, for example, on the physical or functional properties of the TLE gene product in in vitro assay systems, e.g., binding to a ligand or receptor, binding with antibody, possible aggregation (binding) with Notch.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered TLE protein may be controlled. Furthermore, different host cells have characteristic and specific mechanisms for the translational and post-translational processing and modification (e.g., phosphorylation) of proteins. Appropriate cell lines or host systems can be chosen to ensure the desired modification and processing of the foreign protein expressed.

Both cDNA and genomic sequences can be cloned and expressed.

In other specific embodiments, a TLE protein, fragment, analog, or derivative may be expressed as a fusion, or chimeric protein product (comprising the protein, fragment, analog, or derivative joined via a peptide bond to a heterologous protein sequence (of a different protein)). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

In other embodiments, a TLE cDNA sequence may be chromosomally integrated and expressed. Homologous recombination procedures known in the art may be used.

5.8.1. IDENTIFICATION AND PURIFICATION OF THE EXPRESSED GENE PRODUCTS

Once a recombinant which expresses a TLE gene sequence is identified, the gene product can be analyzed. This is achieved by assays based on the physical or functional properties of the product, including radioactive labelling of the product followed by analysis by gel electrophoresis, immunoassay, etc. (see Section 6, infra).

Once a TLE protein is identified, it may be isolated and purified by standard methods including chromatography (e.g., ion exchange, affinity, and sizing column chromatography), centrifugation, differential solubility, or by any other standard technique for the purification of proteins. The functional properties may be evaluated using any suitable assay (see Section 5.10).

Alternatively, the amino acid sequence of a TLE protein can be deduced from the nucleotide sequence of the chimeric gene contained in the recombinant. Once the amino acid sequence is thus known, the protein can be synthesized by standard chemical methods known in the art (e.g., see Hunkapiller et al., 1984, Nature 310:105–111).

By way of example, the deduced amino acid sequences (SEQ ID NOS:2, 4, 6, and 8) of four human TLE proteins or (with respect to TLE 4) a portion thereof are presented in FIGS. 1A–4E. In specific embodiments of the present invention, human TLE proteins, whether produced by recombinant DNA techniques or by chemical synthetic methods, include but are not limited to those containing, as a primary amino acid sequence, all or part of the amino acid sequences substantially as depicted in FIGS. 1A–4E (SEQ ID NOS:2, 4, 6, and 8), as well as fragments and other derivatives, and analogs thereof.

5.8.2. STRUCTURE OF THE HUMAN TLE GENES AND PROTEINS

The structure of the TLE genes and proteins can be analyzed by various methods known in the art.

5.8.2.1. GENETIC ANALYSIS

The cloned DNA or cDNA corresponding to the TLE gene can be analyzed by methods including but not limited to Southern hybridization (Southern, 1975, J. Mol. Biol. 98:503–517), Northern hybridization (see e.g., Freeman et al., 1983, Proc. Natl. Acad. Sci. U.S.A. 80:4094–4098, and Section 6.1.3, infra), restriction endonuclease mapping (Maniatis, 1982, Molecular Cloning, A Laboratory, Cold Spring Harbor, N.Y.), and DNA sequence analysis (see Section 6.3.1 and FIGS. 1A–4E). Polymerase chain reaction (PCR; U.S. Pat. Nos. 4,683,202, 4,683,195 and 4,889,818; Gyllenstein et al., 1988, Proc. Natl. Acad. Sci. U.S.A. 85:7652–7656; Ochman et al., 1988, Genetics 120:621–623; Loh et at., 1989, Science 243:217–220) followed by Southern hybridization with a TLE-specific probe can allow the detection of the TLE genes in DNA from various cell types.

In one embodiment, Southern hybridization can be used to determine the genetic linkage of TLE. Northern hybridization analysis can be used to determine the expression of the TLE genes. Various cell types, at various states of development or activity can be tested for TLE gene expression. Examples of some such techniques and their results are described in Section 6, infra. The stringency of the hybridization conditions for both Southern and Northern hybridization can be manipulated to ensure detection of nucleic acids with the desired degree of relatedness to the specific TLE probe used, whether it be human or Drosophila.

Restriction endonuclease mapping can be used to roughly determine the genetic structure of a TLE gene. Restriction maps derived by restriction endonuclease cleavage can be confirmed by DNA sequence analysis. Alternatively, restriction maps can be deduced, once the nucleotide sequence is known.

DNA sequence analysis can be performed by any techniques known in the art, including(198 limited to the method of Maxam and Gilbert (1980, Meth. Enzymol. 65:499–560), the Sanger dideoxy method (Sanger et al., 1977, Proc. Natl. Acad. Sci. U.S.A. 74:5463), the use of T7 DNA polymerase (Tabor and Richardson, U.S. Pat. No. 4,795,699; Sequenase, U.S. Biochemical Corp.), or Taq polymerase, or use of an automated DNA sequenator (e.g., Applied Biosystems, Foster City, Calif.). The cDNA sequence of three human TLE genes comprises the sequence substantially as depicted in FIGS. 1A–3G (SEQ ID NOS: 1, 3, and 5), and described in Section 6, infra. The cDNA sequence of a portion of a fourth human TLE gene is shown in FIGS. 4A–4E (SEQ ID NO:7) and is described in Section 6, infra.

5.8.2.2. PROTEIN ANALYSIS

The amino acid sequence of a TLE protein can be derived by deduction from the DNA sequence, or alternatively, by direct sequencing of the protein, e.g., with an automated amino acid sequencer. The amino acid sequence of a representative human TLE protein comprises one of the sequences substantially as depicted in FIGS. 1A–4E, and detailed in Section 6, infra.

The TLE protein sequence can be further characterized by a hydrophilicity analysis (Hopp and Woods, 1981, Proc. Natl. Acad. Sci. U.S.A. 78:3824). A hydrophilicity profile can be used to identify the hydrophobic and hydrophilic regions of a TLE protein and the corresponding regions of the gene sequence which encode such regions.

Secondary, structural analysis (Chou and Fasman, 1974, Biochemistry 13:222) can also be done, to identify regions of a TLE protein that assume specific secondary structures.

Manipulation, translation, and secondary structure prediction, as well as open reading frame prediction and plotting, can also be accomplished using computer software programs available in the art.

Other methods of structural analysis can also be employed. These include but are not limited to X-ray crystallography (Engstom, 1974, Biochem. Exp. Biol. 11:7–13) and computer modeling (Fletterick and Zoller (eds.), 1986, Computer Graphics and Molecular Modeling, in Current Communications in Molecular Biology, Cold Spring Harbor Laboratory, Cold Spring Harbor, N.Y.).

5.9. DERIVATIVES AND ANALOGS OF TLE PROTEINS AND TLE LIGANDS

The invention further provides, as Therapeutics, derivatives (including but not limited to fragments) and analogs of TLE proteins. Also provided as Therapeutics are other proteins and derivatives and analogs thereof, or TLE ligands, in particular, which promote or, alternatively, inhibit the interactions of such other proteins with a TLE protein.

The production and use of derivatives and analogs related to TLE proteins are within the scope of the present invention. In a specific embodiment, the derivative or analog is functionally active, i.e. , capable of exhibiting one or more functional activities associated with a full-length, wild-type TLE protein. As one example, such derivatives or analogs which have the desired immunogenicity or antigenicity can be used, for example, in diagnostic immunoassays as described in Section 5.6. Molecules which retain, or alternatively inhibit, a desired TLE protein property, e.g., binding to a receptor or ligand, such as possibly Notch protein, can be used therapeutically as inducers, or inhibitors, respectively, of such property and its physiological correlates. Derivatives or analogs of TLE proteins can be tested for the desired activity by procedures known in the art, including but not limited to the assays described infra. In one specific embodiment, peptide libraries can be screened to select a peptide with the desired activity; such screening can be carried out by assaying, e.g., for binding to a TLE protein or a TLE binding partner.

In particular, TLE derivatives can be made by altering TLE sequences by substitutions, additions or deletions that provide for functionally equivalent molecules. Due to the degeneracy of nucleotide coding sequences, other DNA sequences which encode substantially the same amino acid sequence as a TLE gene may be used in the practice of the present invention. These include but are not limited to nucleotide sequences comprising all or portions of TLE genes which are altered by the substitution of different codons that encode a functionally equivalent amino acid residue within the sequence, thus producing a silent change. Likewise, the TLE derivatives of the invention include, but are not limited to, those containing, as a primary amino acid sequence, all or part of the amino acid sequence of a TLE protein including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

In a specific embodiment of the invention, proteins consisting of or comprising a fragment of a TLE protein consisting of at least fifty amino acids of the TLE protein is provided. In other embodiments, the fragment consists of at least 100 amino acids of the TLE protein.

Derivatives or analogs of TLE proteins include but are not limited to those peptides which are substantially homologous (e.g., greater than 70% identity) to a TLE protein or fragment thereof, or whose encoding nucleic acid is capable of hybridizing to a TLE nucleic acid sequence.

The TLE protein derivatives and analogs of the invention can be produced by various methods known in the art. The manipulations which result in their production can occur at the gene or protein level. For example, the cloned TLE gene sequence can be modified by any of numerous strategies known in the art (Maniatis, 1990, Molecular Cloning, A Laboratory Manual, 2d ed., Cold Spring Harbor Laboratory, Cold Spring Harbor, N.Y.). The sequence can be cleaved at appropriate sites with restriction endonuclease(s), followed by further enzymatic modification if desired, isolated, and ligated in vitro. In the production of the gene encoding a derivative or analog of a TLE protein, care should be taken to ensure that the modified gene remains within the same translational reading frame as the TLE gene, uninterrupted by translational stop signals, in the gene region where the desired TLE protein activity is encoded.

Additionally, the TLE-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson et al., 1978, J. Biol. Chem 253:6551), use of TAB® linkers (Pharmacia), etc.

Manipulations of the TLE sequence may also be made at the protein level. Also provided by the invention as Therapeutics are TLE protein fragments or other derivatives or analogs which are differentially modified during or after translation, e.g., by acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$, acetylation, formylation, oxidation, reduction, etc.

In a preferred aspect, phosphorylation or, alternatively, dephosphorylation is carried out, which can be to various extents, on the purified TLE protein or derivative thereof. The phosphorylation state of the molecule may determine the distribution of the TLE protein between the cellular compartments of the nucleus and the cytoplasm (see Section 6, infra). Thus, controlling the phosphorylation state may allow control of intracellular localization. Phosphorylation can be carried out by reaction with an appropriate kinase (e.g., possibly cdc2 or CK II). Dephosphorylation can be carried out by reaction with an appropriate phosphatase.

In addition, analogs and derivatives of TLE proteins can be chemically synthesized. For example, a peptide corresponding to a portion of a TLE protein which comprises the desired domain (see Section 5.6.1), or which mediates the desired activity in vitro, can be synthesized by use of a peptide synthesizer. Furthermore, if desired, nonclassical amino acids or chemical amino acid analogs can be introduced as a substitution or addition into the human TLE protein sequence. Non-classical amino acids include but are not limited to the D-isomers of the common amino acids, α-amino isobutyric acid, 4-aminobutyric acid, hydroxyproline, sarcosine, citrulline, cysteic acid, t-butylglycine, t-butylalanine, phenylglycine, cyclohexylalanine, β-alanine, designer amino acids such as β-methyl amino acids, Cα-methyl amino acids, and Nα-methyl amino acids.

In a specific embodiment, the TLE derivative is a chimeric, or fusion, protein comprising a TLE protein or fragment thereof (preferably consisting of at least a domain or motif of the TLE protein, or at least 50 amino acids of the TLE protein) joined at its amino or carboxy-terminus via a peptide bond to an amino acid sequence of a different protein. In one embodiment, such a chimeric protein is produced by recombinant expression of a nucleic acid encoding the protein (comprising a TLE-coding sequence joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. A specific embodiment relates to a chimeric protein comprising a fragment of a TLE protein which comprises a domain or motif of the TLE protein, e.g., a Q domain, GP domain, CcN domain, SP domain, WD-40 domain, one or more WD-40 repeats or a consensus WD-40 repeat (FIG. 6), NLS, CK II site, or cdc2 site. In a particular embodiment, a chimeric nucleic acid can be constructed, encoding a fusion protein consisting of a TLE nuclear localization sequence (NLS) or CcN motif (see Table I, Section 6, infra) joined to a non-TLE protein. Such a chimeric protein may thus be localized intracellularly to the nucleus of a cell into which it is introduced, by virtue of its TLE sequence. The invention thus provides a method for delivering a Therapeutic to the nucleus of a cell, by linkage of such Therapeutic to or constructing such Therapeutic to contain, a TLE protein NLS or CcN motif (the CcN motif contains an NLS). As another example, and not by way of limitation, a recombinant molecule can be constructed comprising coding portions of both a TLE gene and another toporythmic gene. Another specific embodiment relates to a chimeric protein comprising a fragment of a TLE protein of at least six amino acids.

A particular example of a human TLE fusion protein, consisting of a human TLE fragment capable of generating anti-TLE antibody fused to the carboxyl-terminus of glutathione-S-transferase, is described in Section 7 hereof.

Derivatives of other proteins, such as TLE binding partners, can be made by methods similar to those described supra.

Other specific embodiments of derivatives and analogs are described in the subsections below and examples sections infra.

5.9.1. DERIVATIVES OF HUMAN TLE PROTEINS CONTAINING ONE OR MORE DOMAINS OF THE PROTEIN

In a specific embodiment, the invention provides Therapeutics that are TLE protein derivatives and analogs, in particular, TLE fragments and derivatives of such fragments, that comprise one or more domains of a TLE protein, including but not limited to a Q domain [amino acids (approximately) 1-131, 1-127, and 1-130 for TLE 1, TLE 2, and TLE 3, respectively], GP domain [amino acids (approximately) 132-199, 128-191, and 131-197 for TLE 1, TLE 2, and TLE 3, respectively], CcN domain [amino acids (approximately) 200-268, 192-254, and 198-267 for TLE 1, TLE 2, and TLE 3, respectively], SP domain [amino acids (approximately) 269-449, 255-422, and 268-450 for TLE 1, TLE 2, and TLE 3, respectively], WD-40 domain [amino acids (approximately) 450-770, 423-743, and 451-774, for TLE 1, TLE 2, and TLE 3, respectively, and the last ~321 amino acids of TLE 4] (see FIG. 5A–5C for sequences of all of the foregoing), one or more WD-40 repeats (see FIG. 6), or a consensus WD-40 repeat (FIG. 6), NLS (Table I), CK II site (Table I), or cdc2 site (Table I). A consensus WD-40 repeat is shown in FIG. 6, and consists of the following sequence (SEQ ID NO:9): PXXXX(D or E)XTXXXXXXXX(I or L)X(I or L)SPDG(T or S)XLX(T or S)GGXDGXVXXWDLX, where X is any amino acid. The CcN domains comprise the CcN motifs, which latter span approximately amino acids 225-269, 214-255, and 224-268, for TLE 1, TLE 2, and TLE 3, respectively.

5.9.2. DERIVATIVES OF TLE PROTEINS THAT MEDIATE BINDING TO PROTEINS, AND INHIBITORS THEREOF

The invention also provides TLE fragments, and analogs or derivatives of such fragments, which mediate binding to other proteins, and nucleic acid sequences encoding the foregoing. As shown in Section 7, infra, TLE proteins associate in multiprotein complexes, and thus bind to other proteins. In a specific embodiment, a non-TLE protein component of such multiprotein complexes is an ~17 kD protein.

Also included as Therapeutics of the invention are inhibitors (e.g., peptide inhibitors) of the foregoing protein interactions with a TLE protein.

5.10. ASSAYS OF TLE PROTEINS, DERIVATIVES AND ANALOGS

The functional activity of TLE proteins, derivatives and analogs, and TLE binding partners can be assayed by various methods.

For example, in one embodiment, where one is assaying for the ability to bind or compete with a wild-type TLE protein for binding to anti-TLE protein antibody, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are within the scope of the present invention.

The ability to bind to another protein (be it a second TLE protein, a non-TLE component of the multiprotein complexes described in Sections 5.6 and 7, possibly a Notch protein, or otherwise) can be demonstrated by in vitro binding assays, noncompetitive or competitive, by methods known in the art. Thus, where a receptor or ligand for a TLE protein is identified, receptor or ligand binding can be assayed, e.g., by means well known in the art.

In another embodiment, physiological correlates of TLE introduction into cells can be assayed.

In another embodiment, in insect or other model systems, genetic studies can be done to study the phenotypic effect of a TLE mutant that is a derivative or analog of a wild-type TLE gene.

Other methods will be known to the skilled artisan and are within the scope of the invention.

5.11. BINDING PARTNERS OF TLE PROTEINS

The invention further provides Therapeutics which are binding partners (ligands) of a TLE protein, as well as inhibitors of the binding between a TLE protein and such a binding partner. In a specific embodiment, such TLE ligands are found in a multiprotein complex containing TLE proteins (see Section 7, infra). Such protein components of complexes containing TLE proteins may act as effector molecules in TLE protein signal transduction events and thus have potential uses in modulation of TLE protein activity. In specific embodiments, such a multiprotein complex containing a TLE protein or epitope thereof (as detected e.g., by the ability to be bound by an anti-TLE protein antibody) has a molecular weight of at least about 670,000 daltons; in yet other aspects, such a complex has a molecular weight of about 110, 170, 190, or 230 kilodaltons. These complexes of smaller molecular weight may be components of the larger complexes. In a specific embodiment, the invention provides a Therapeutic which is a protein component of such a multiprotein complex, with a molecular weight in the range of about 15,000–18,000 daltons, in particular, about 17,000 daltons, as detected by SDS-polyacrylamide gel electrophoresis. The invention also provides antibodies as Therapeutics, in particular, monoclonal antibodies, which specifically bind to the non-TLE protein components of such multiprotein complexes. In one embodiment, such antibodies are obtained by using as immunogen the multiprotein TLE complexes and selecting for negative TLE protein reactivity and positive TLE complex reactivity.

5.12. ANTIBODIES TO TLE PROTEINS AND DERIVATIVES THEREOF

According to one embodiment of the invention, antibodies and fragments containing the binding domain thereof directed against a TLE protein are Therapeutics. Accordingly, a TLE protein, its fragments or other derivatives, or analogs thereof, may be used as an immunogen to generate antibodies which recognize such an immunogen. Such antibodies include but are not limited to polyclonal, monoclonal, chimeric, single chain, Fab fragments, or from an Fab expression library. In a preferred embodiment, antibodies which specifically bind to human TLE proteins are produced. In one embodiment, such an antibody recognizes the human TLE proteins TLE 1, TLE 2, TLE 3, and TLE 4, or a portion thereof. In another embodiment, such an antibody specifically binds to one human TLE protein selected from among TLE 1, TLE 2, TLE 3, and TLE 4, but does not bind to a different human TLE protein. In another embodiment, antibodies to a particular domain of a TLE protein are produced.

Various procedures known in the art may be used for the production of polyclonal antibodies to a TLE protein or derivative or analog. In a particular embodiment, rabbit polyclonal antibodies to an epitope of one of the TLE proteins encoded by a sequence depicted in FIGS. 1A–1H, 2A–2G, 3A–3G or 4A–4E a subsequence thereof, can be obtained. For the production of antibody, various host animals can be immunized by injection with a native TLE protein, or a synthetic version, or derivative (e.g., fragment) thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

In a preferred embodiment, polyclonal or monoclonal antibodies are produced by use of a hydrophilic portion of a TLE peptide (e.g., identified by the procedure of Hopp and Woods (1981, Proc. Natl. Acad. Sci. U.S.A. 78:3824)).

For preparation of monoclonal antibodies directed toward a TLE protein sequence or analog thereof, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in *Monoclonal Antibodies and Cancer Therapy*, Alan R. Liss, Inc., pp. 77–96) can be used. In an additional embodiment of the invention, monoclonal antibodies can be produced in germ-free animals (PCT Publication No. WO 89/12690 dated Dec. 28, 1989). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96), or by other methods known in the art. In fact, according to the invention, techniques developed for the production of "chimeric antibodies" (Morrison et al., 1984, Proc. Natl. Acad. Sci. U.S.A. 81:6851–6855; Neuberger et al., 1984, Nature 312:604–608; Takeda et al., 1985, Nature 314:452–454) by splicing the genes from a mouse antibody molecule specific for a TLE protein together with genes from a human antibody molecule of appropriate biological activity can be used; such antibodies are within the scope of this invention.

According to the invention, techniques described for the production of single chain antibodies (U.S. Pat. No. 4,946,778) can be adapted to produce TLE protein-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for TLE proteins, derivatives, or analogs.

Antibody fragments which contain the idiotype (binding domain) of the molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g. ELISA (enzyme-linked immunosorbent assay). For example, to select antibodies which recognize a specific domain of a TLE protein, one may assay generated hybridomas for a product which binds to a TLE fragment containing such domain. For selection of an antibody specific to human TLE protein(s), one can select on the basis of positive binding to a human TLE protein and a lack of binding to Drosophila TLE protein.

In another aspect of the invention, antibodies to a non-TLE protein component of multiprotein complexes containing a TLE protein (see Section 7) are provided. Such antibodies can be obtained by a method comprising immunizing an animal with such multiprotein complexes.

In addition to therapeutic utility, the foregoing antibodies have utility in diagnostic immunoassays as described in Section 5.6 supra.

6. THE HUMAN HOMOLOGS OF THE TRANSDUCIN-LIKE ENHANCER OF SPLIT GENE PRODUCT OF THE DROSOPHILA "NOTCH GROUP" DEFINE A NOVEL FAMILY OF NUCLEAR PROTEINS

The Drosophila m9/10 gene (groucho) of the Enhancer of split [E(spl)] complex is part of a genetic circuitry, the so-called Notch group of genes, which is required for a variety of cell fate choices in Drosophila including the segregation of neural and epidermal cell lineages. As described herein, we have characterized human cDNA clones encoding a family of proteins, designated TLE, that are homologous to the E(spl) m9/10 gene product. The TLE and E(spl) m9/10 proteins share two amino acid sequence motifs. The first is a tandem array of four so-called "WD-40" repeats at the carboxyl end of the molecule and the second, referred to as the "CcN motif", consists of a closely-spaced combination of a nuclear localization sequence and potential phosphorylation sites for both casein kinase II and cdc2 kinase. As described herein, the TLE proteins were shown to be predominantly nuclear in HeLa cells, and the Drosophila E(spl) m9/10 protein was shown to be phosphorylated. These results suggest a role for the E(spl) m9/10 and human TLE proteins as nuclear effector molecules.

6.1. RESULTS

6.1.1. ISOLATION AND CHARACTERIZATION OF HUMAN E(spl) m9/10 HOMOLOGS

We searched for human homologs of the E(spl) m9/10 gene using a fortuitously isolated 1.7-kb cDNA clone from a human testis cDNA library (see Materials and Methods). This clone contains a partial open reading frame (ORF) encoding a 282 residue long polypeptide chain exhibiting homology to the portion of the E(spl) m9/10 protein that includes the four WD-40 repeats.

This partial cDNA clone was used to screen a human fetal brain cDNA library, resulting in the isolation of four classes of clones, hereafter referred to as TLE 1, TLE 2, TLE 3, and TLE 4 (Transducin-Like Enhancer of split). cDNAs TLE 1, TLE 2, and TLE 3 contain entire ORFs for three distinct proteins of 770 ($M_r$ 83,000), 743 ($M_r$ 80,000), and 774 ($M_r$ 83,000) amino acids, respectively, while TLE 4 is a partial clone. All encoded proteins are homologous to E(spl)m9/10. The complete nucleotide sequence (SEQ ID NO: 1) and deduced amino acid sequence ((SEQ ID NO:2) for TLE 1 are shown in FIGS. 1A–1H. The complete nucleotide sequence (SEQ ID NO:3) and deduced amino acid sequence (SEQ ID NO:4) for TLE 2 are shown in FIGS. 2A–2G. The complete nucleotide sequence (SEQ ID NO:5) and deduced amino acid sequence (SEQ ID NO:6) for TLE 3 are shown in FIGS. 3A–3G. The partial nucleotide sequence (SEQ ID NO:7) and deduced amino acid sequence (SEQ ID NO:8) for TLE 4 are shown in FIGS. 4A–4E. As is the case with the E(spl) m9/10 protein (Hartley et al., 1988, Cell 55:785–795), analysis of hydropathy plots for TLE 1, TLE 2, and TLE 3 indicated that the TLE proteins are quite hydrophilic and appear not to have a signal sequence (not shown).

6.1.2. DOMAIN STRUCTURE OF TLE PROTEINS

A comparison of the Drosophila E(spl) m9/10 protein (SEQ ID NO: 10) and human TLE proteins is shown in FIGS. 5A–5C. The first ~130 residues at the amino terminus of the proteins are highly conserved and have a high content of conserved glutamine residues. Thus, we refer to this region as the "Q domain". In this region, TLE 1 is 72%, TLE 2 is 68%, and TLE 3 is 71% identical to E(spl) m9/10. Adams et al. (1991, Science 252:1651–1656) have recently described partial DNA sequences of more than 600 randomly selected cDNA clones from human brain. Sequencing of ~250 nucleotides of Adams et al. clone EST00256 identified a reading frame coding for a protein related to E(spl) m9/10; this short sequence maps within the first 100 residues of the amino terminus of m9/10. Comparing the corresponding region of the TLE 1, TLE 2, and TLE 3 cDNAs with the nucleotide and predicted amino acid sequence of cDNA EST00256, we failed to show identity among these cDNAs. This suggests that cDNA EST00256 is either part of the sequence coding for TLE 4, the sequence of which remains to be fully determined, or part of yet another member of this family.

casein kinase II (CK II) site/eric2 kinase (cdc2) site/nuclear localization sequence (NLS) motif first reported for the SV40 T antigen (Jans et al., 1991, J. Cell Biol. 115: 1203–1212; Rihs et al., 1991, EMBO J. 10:633–639). NLS, a cluster of four positively charged amino acids preceded, at a distance of ten residues, by a block of two or three basic amino acids (Kalderon et al., 1984, Nature 311:499–509; Dingwall and Laskey, 1991, Trends Biochem. Sci. 16:478–481), is in proximity to possible phosphorylation sites for both casein kinase II (defined by the consensus sequence $^S/_T XX^D/_E$) and cdc2 kinase (defined by the consensus sequence $^S/_T PXZ$, with X being dispensable and Z being generally a basic residue). Table I shows a comparison of the CcN motif found in E(spl) m9/10, TLE 1, TLE 2, and TLE 3. E(spl) m9/10, TLE 1, and TLE 3 have conventional NLSs, while TLE 2 deviates from the general consensus. It is worth noting, however, that a certain degree of flexibility in the selection of the amino acids that form a NLS has been observed previously (Dingwall and Laskey, 1991, Trends Biochem. Sci. 16:478–481).

TABLE I

Comparison of the CcN motif between E(spl) m9/10 and human TLE proteins*

| Protein | | NLS | CK II site | cdc2 site |
|---|---|---|---|---|
| E(spl) m9/10 | 204 | -YRTRSPLDIENDSKRRK-DEKLQEDEGEKSDQD-----LVVDVANE-MESHSPRP | | |
| TLE 1 | 212 | DKRRNGP-EFSNDIKKRKVDDKDSSH-YD-SDGDKSDDNLVVDVSNED-PS-SPRASPAHSPR | | |
| TLE 2 | 203 | EERPSGP---GGGGKQR-ADEKEPSGPYE-SDEDKSDYNLVVD---EDQPSE-PP-SPATTPC | | |
| TLE 3 | 211 | EKHRGSA-DYSMEAKKRKVEEKDSLSRYD-SDGDKSDD-LVVDVSNED-P-ATPRVSPAHSPP | | |

*The nuclear localization sequence (NLS) and the possible phosphorylation sites for casein kinase II (CK II) and cdc2 are indicated by large characters. Identical amino acids and conservative substitutions are underlined.

A poorly conserved region of approximately 80 amino acid residues follows the Q domain. We refer to this portion of the molecules as the "GP domain" to indicate the presence of numerous glycine and proline residues. The lack of significant structural conservation in the GP domain ends approximately 200 residues from the amino terminus, in the "CcN domain" (Jans et al., 1991, J. Cell Biol. 115: 1203–1212).

The CcN domain consists of a stretch of ~60 residues that harbors a sequence motif conforming to the definition of a Table II shows the relationship between the NLS and putative phosphorylation sites in E(spl) m9/10, TLE 1, TLE 2, TLE 3, as well as other proteins bearing the CcN motif; these proteins were selected on the basis of demonstrated nuclear localization and susceptibility to phosphorylation. Most, if not all, of them play important roles in regulating nuclear functions such as transcription and mitosis, as well as other aspects of the cell cycle (for review, see Meisner and Czech, 1991, Curt. Op. Cell Biol. 3:474–483; Moreno and Nurse, 1990, Cell 61:549–551).

TABLE II*

Comparison of the CcN motif of E(spl) m9/10, TLE proteins, and proteins with demonstrated nuclear localization and susceptibility to phosphorylation by casein kinase II and/or cdc2

| Protein | NLS | CK II site+ | cdc2 site+ |
|---|---|---|---|
| E(spl) m9/10 | KRRK$^{219}$ | $^{231}$SDQD | $^{247}$SPRP |
| TLE 1 | KKRK$^{228}$ | $^{239}$SDGD | $^{259}$SPRA$^{263}$SPAH$^{267}$SPR |
| TLE 2 | KQRA$^{217}$ | $^{228}$SDED | $^{249}$SPAT$^{253}$TPCGK |
| TLE 3 | KKRK$^{227}$ | $^{239}$SDGD | $^{258}$TPRV$^{262}$SPAH$^{266}$SPP |
| SV40 T antigen[b,c,d] | KKRK$^{131}$ | $^{111}$S$^{112}$SDDE | S$^{124}$TPPK |
| | SEQ ID NO: 11 | SEQ ID NO: 12 | SEQ ID NO: 13 |
| human c-myc[e,f] | RQRR$^{367}$ | S$^{384}$SDTE | T$^{344}$ SPRS |
| | SEQ ID NO: 14 | SEQ ID NO: 15 | SEQ ID NO: 16 |

TABLE II*-continued

Comparison of the CcN motif of E(spl) m9/10, TLE proteins, and proteins with demonstrated nuclear localization and susceptibility to phosphorylation by casein kinase II and/or cdc2

| Protein | NLS | CK II site+ | cdc2 site+ |
|---|---|---|---|
| human p53[g,h,i] | KKKP$^{319}$ | $^{284}$TEEE | S$^{315}$SPQP |
| | SEQ ID NO: 17 | SEQ ID NO: 18 | SEQ ID NO: 19 |
| human A-myb[j,k] | RKKR$^{451}$ | $^{467}$SLND | $^{479}$TRLK |
| | SEQ ID NO: 20 | SEQ ID NO: 21 | SEQ ID NO: 22 |
| dorsal[a,l] | KRQK$^{340}$ | $^{312}$SDGV$^{316}$TSEA | $^{290}$TPRY |
| | SEQ ID NO: 23 | SEQ ID NO: 24 | SEQ ID NO: 25 |

*Standard one-letter amino acid symbols are used; see e.g., Lehninger, 1975, Biochemistry, 2d. Ed., Worth Publishers, Inc., New York, p. 72.
+Phosphorylatable Ser/Thr residues are numbered.
[a]The Drosophila protein dorsal was included as one example of several other proteins bearing a putative CcN motif for which only translocation to the nucleus has been demonstrated.
[b]Kalderon et al., 1984, Nature 311:499–509
[c]McVey et al., 1989, Nature 341:503–507
[d]Grasser et al., 1988. Virology 165:13–22
[e]Dang and Lee, 1988, Mol. Cell. Biochem. 8:4048–4054
[f]Luscher et al., 1989, EMBO J. 8:1111–1119
[g]Jenkins et al., 1984, Nature 312:651–654
[h]Bischoff et al., 1990, Proc. Natl. Acad. Sci. USA 87:4766–4770
[i]Meek et al., 1990, EMBO J. 9:3253–3260
[j]Nomura et al., 1988, Nucleic Acids Res. 16:11075–11089
[k]Lüscher et al., 1990, Nature 344:517–522
[l]Steward, 1987, Science 238:692–694

A poorly conserved region of 150–180 amino acids rich in serine and proline residues, the "SP domain," separates the CcN domain from the carboxyl-terminal region which contains the WD-40 repeats and shows the most impressive similarity among the E(spl) m9/10 and the TLE proteins.

FIG. 6 shows the sequence conservation in the "WD-40 domain" among all five proteins: TLE 1 is 89%, TLE 2 is 83%, TLE 3 is 87%, and TLE 4 is 89% identical to the Drosophila m9/10 protein. Large blocks of sequence are highly conserved within each individual group of repeats and when all repeats are compared inter se, a consensus motif can be identified at the carboxyl-terminal end of each repeat, terminating in the conserved WDL sequence.

In conclusion, comparison of the deduced amino acid sequence of the Drosophila m9/10 and human TLE proteins reveals the presence of three conserved structural elements: the Q-, the CcN-, and the WD-40 domains (see FIGS. 5A–5C). Interestingly, we noticed that a similar domain structure is exhibited by the product of the yeast TUPI gene, isolated by Williams and Trumbly (1990, Mol. Cell. Biol. 10:6500–6511).

6.1.3. EXPRESSION OF TLE mRNAs

Figure 7B:
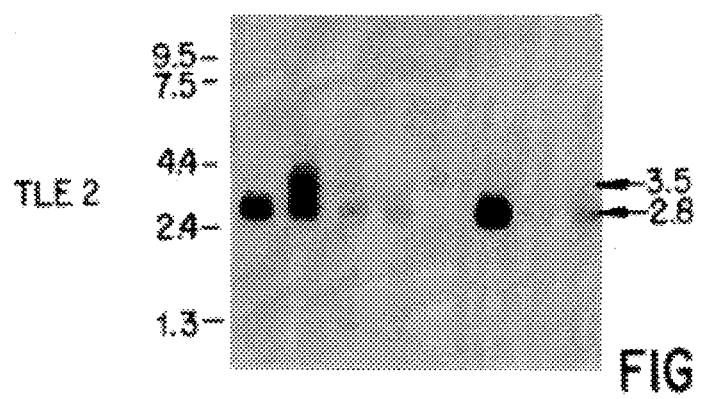
Figure 7C:
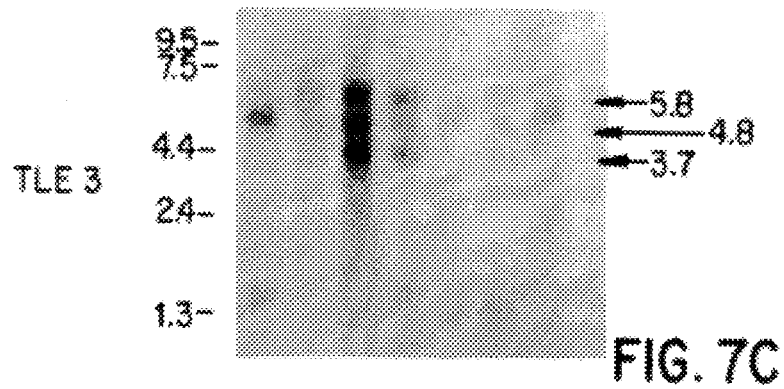
Figure 7D:
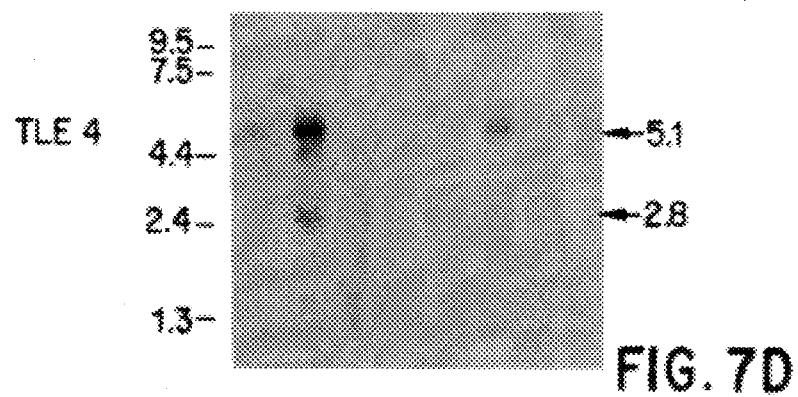

The distribution of the various TLE mRNAs was determined by Northern blotting analyses of poly A$^{(+)}$ RNA. These studies revealed that the TLE 1 mRNA migrates as a major species of 4.5 kb detectable in all adult tissues examined, with the highest level of expression in brain, liver, and muscle (FIG. 7A). Minor species of 5.8 and 3.2 kb were also detectable. Two distinct TLE 2 mRNAs were detected (FIG. 7B). One transcript, of 2.8 kb, was expressed at different levels in all tissues examined and was noticeably abundant in heart, brain, and muscle; the second transcript, of 3.5 kb, appeared to be expressed only in brain. Three distinct TLE 3 transcripts were present, having sizes of 5.8, 4.8, and 3.7 kb. Placenta and lung are the only tissues where all these mRNAs were detected, while the remaining tissues only expressed either one or two of them (FIG. 7C). Finally, two major TLE 4 transcripts of 5.1 and 2.8 kb were observed. They were predominantly expressed in brain and muscle, but were also present in all other tissues investigated (FIG. 7D).

In aggregate, the TLE mRNAs are expressed in all tissues examined with individual transcripts showing specific patterns of expression.

6.1.4. IMMUNOCYTOCHEMICAL CHARACTERIZATION OF TLE PROTEINS

In order to determine the intracellular distribution of the TLE proteins, we raised monoclonal antibodies against a fusion protein containing the carboxyl-terminal-most 282 amino acids of TLE 3 fused to glutathione S-transferase (Smith and Johnson, 1988, Gene 67:31–40). FIG. 8A illustrates the results of Western blotting experiments performed with monoclonal antibody C597.4A. A small number of closely spaced immunoreactive species with apparent molecular weights of ~85,000 was detected in all tissues examined. Monoclonal antibody C597.4A was selected based on its ability to cross-react with Drosophila E(spl) m9/10, as well as with rat proteins also exhibiting apparent molecular weights of ~85,000 (not shown). Thus, this antibody seems to recognize an epitope that has been conserved across species boundaries. This is not surprising, since the TLE 3 fusion protein contained the highly conserved WD-40 domain (as shown in FIG. 6); in this domain TLE 3 is 87%, 94%, 85%, and 94% identical to E(spl) m9/10, TLE 1, TLE 2, and TLE 4, respectively. We therefore expect that, in addition to TLE 3, this antibody will recognize the remaining TLE proteins in humans and that the ~85-kDa bands observed in FIG. 8A correspond to more than one TLE protein. As expected from the transcript analysis described in FIGS. 7A–7D, these investigations revealed that the TLE proteins are expressed in a broad range of human tissues and cell lines, including the human SUP-T1 cell line which was established from an acute T lymphoblastic leukemia and was shown to contain a translocation interrupting the TAN-1 coding sequence (Ellisen et al., 1991, Cell 66:649–661).

We investigated the intracellular distribution of the TLE proteins in HeLa cells by indirect immunofluorescence microscopy using monoclonal antibody C597.4A. FIG. 8B shows that the TLE proteins were predominantly localized to the nucleus. However, a much weaker but nevertheless above background staining was consistently seen in the cytoplasm. Preliminary studies with monoclonal antibodies we have developed that are specific for TLE 1 and TLE 2 have revealed that both of these proteins are also expressed in HeLa cells. Identical results were obtained using the SUP-T1 cell line (not shown).

6.1.5. THE DROSOPHILA E(spl) m9/10 PROTEIN IS PHOSPHORYLATED

We have asked the question of whether or not the Drosophila E(spl) m9/10 protein is phosphorylated. Drosophila S2 cells were pulse-labeled with $^{32}$p and lysed as described in Materials and Methods. A single phosphorylated protein was detected in the immunoprecipitates obtained with monoclonal antibody 3C, which is directed against Drosophila E(spl) m9/10 (Delidakis et at., 1991, Genetics 129:803–823). The electrophoretic mobility of this molecule corresponded to that expected for the m9/10 protein. Although we have not shown directly that m9/10 is phosphorylated on Ser/Thr residues, we do know that phosphorylation does not seem to occur at Tyr residues: when the immunoprecipitates were probed with a monoclonal antibody specific for phosphorylated Tyr residues (Glenney et al., 1988, J. Immunol. Meth. 109:277–283), no detectable immunoreactivity was observed (not shown).

The expression profile of the Drosophila m9/10 protein during embryogenesis was revealed by Western blotting analysis. Two closely-spaced bands were detected with monoclonal antibody 3C. The lower band was predominant very early in development and became progressively less abundant at later stages, while the higher band showed exactly an opposite profile. Given that the E(spl) m9/10 protein was shown to be the product of a single gene (Hartley et al., 1988, Cell 55:785–795; Preiss et al., 1988, EMBO J. 7:3917–3927), it is possible that this electrophoretic profile reflects a developmentally regulated post-translational modification such as phosphorylation.

Overall, our results demonstrate two of the features suggested by the presence of a CcN motif, namely nuclear targeting and susceptibility to phosphorylation.

6.2. DISCUSSION

In the present work we provide evidence that the m9/10 gene of E(spl), a member of the Notch group, has also been conserved during evolution to a surprising degree and that in humans there is a family of m9/10-homologous proteins. These gene products, named TLE, show a striking conservation at their carboxyl-terminal regions, where a tandemly duplicated organization of four ~40-residue long repeats defines an extraordinarily well conserved structural domain. Similarly organized arrangements of so-called WD-40 repeats have recently been observed in an expanding group of unrelated proteins including the β subunits of heterotrimeric G proteins (for review, see Simon et al., 1991, Science 252:802–808), the products of the yeast genes CDC 4, which is involved in regulating the cell cycle (Yochem and Byers, 1987), TUP1, a mediator of glucose repression (Williams and Trumbly, 1990, Mol. Cell. Biol. 10:6500–6511), PRP4, a stable component of the U4/U6 small nuclear ribonucleoprotein particle (Dalrymple et al., 1989, Cell 58:811–812), and MS11, a negative regulator of the RAS-mediated induction of cAMP (Ruggieri et al., 1989, Proc. Natl. Acad. Sci. USA 86:8778–8782), as well as the product of the vertebrate 12.3 gene, initially identified by virtue of its physical linkage to the chicken major histocompatibility complex (Guillemat et al., 1989, Proc. Natl. Acad. Sci. USA 86:4594–4598).

Recent genetic (Goebl and Yanagida, 1991, Trends Biochem. Sci. 16:173–177) and molecular (Williams et al., 1991, Mol. Cell. Biol. 11:3307–3316) investigations with several yeast mutants have provided evidence for the existence of interactions between some members of the WD-40 repeat family and some members of a novel group of proteins characterized by the presence of the so-called TPR snap helix repeat (for review, see Goebl and Yanagida, 1991, Trends Biochem. Sci. 16: 173–177). These genetic associations always involve a pair of genes, representing either the WD-40 repeat family or the TPR helix family, thus suggesting a possible mutual relation of these two motifs. Analysis of the cellular functions carried out by most of these proteins indicates that they are involved in nuclear activities ranging from regulation of mitosis to regulation of transcription.

A second noteworthy structural feature shared by E(spl) m9/10 and TLE proteins is the presence of the CcN motif (FIGS. 5A–5C and Table I). The CcN motif has been found in several nuclear proteins involved in regulating cell differentiation or proliferation (Jans et al., 1991, J. Cell Biol. 115:1203–1212). Studies with SV40 T antigen have demonstrated that absence of the Ser residue of the CK II site of the CcN motif, which can be phosphorylated, causes a reduction of the rate of nuclear transport of the protein (Rihs et al., 1991, EMBO J. 10:633–639). On the other hand, phosphorylation of Thr$^{124}$ of the cdc2 site within the CcN motif inhibits nuclear import of SV40 T antigen fusion proteins (Jans et al., 1991, J. Cell Biol. 115:1203–1212). These studies suggest that the phosphorylation state of the SV40 T antigen determined by these two kinases controls the cytoplasmic/nuclear distribution of the protein, thus providing a possible mechanistic explanation for the presence of CK II and cdc2 phosphorylation sites in many proteins with known nuclear functions (for review, see Meisner and Czech, 1991, Curr. Op. Cell Biol. 3:474–483; Moreno and Nurse, 1990, Cell 61:549–551). Such a mechanism could also be involved in mediating the predominantly, but not exclusively, nuclear localization of E(spl) m9/10 (Delidakis et al., 1991, Genetics 129:803–823) and TLE proteins (FIG. 8B). Indeed, in agreement with the observation that most of the proteins carrying a CcN motif have been shown to be phosphorylated by CK II and/or cdc2 (Meisner and Czech, 1991, Curr. Op. Cell Biol. 3:474–483), we have shown that the m9/10 protein is phosphorylated in cultured Drosophila S2 cells. We do not have direct evidence that m9/10 is phosphorylated in embryos, but it is possible that the developmental profile we observed reflects the presence of differentially phosphorylated forms of the protein. This possibility is particularly attractive since it would provide a possible mechanism for regulating the relative distribution of the protein between cytoplasm and nucleus. In turn, this would permit direct interactions with a membrane-bound molecule such as Notch. Such molecular interactions could explain the documented genetic interactions between specific intracellular Notch mutations and certain E(spl) m9/10 alleles (Xu et al., 1990, Genes Dev. 4:464–475). Moreover, phosphorylation/dephosphorylation reactions may be used to stabilize or prevent associations with other factors.

Thus, the demonstration of nuclear targeting and susceptibility to phosphorylation, two of the features associated with the presence of a CcN motif, lends support to the concept that this motif is an important functional element of these proteins. It is also worth noting that the nuclear/ cytoplasmic distribution of the various TLE proteins may not be the same under varying physiological conditions. Subsets of these proteins may redistribute in specific ways between cellular compartments in response to intracellular as well as extracellular changes.

The extraordinary structural conservation among the Drosophila and human gene products described herein implies that the biochemical mechanisms involving E(spl) m9/10-like proteins may also be conserved across species boundaries, as part of a general and pleiotropic pathway involved in controlling many aspects of mammalian cell fate.

6.3. MATERIALS AND METHODS

6.3.1. GENERAL METHODS AND MATERIALS

Standard molecular biology techniques were used (Sambrook et al., 1989, Molecular cloning: A Laboratory Manual, 2d Ed., Cold Spring Harbor Laboratory, Cold Spring Harbor, N.Y.). SDS-polyacrylamide gel electrophoresis (PAGE), transfer to nitrocellulose, and Western blotting were as described by Stifani et al. (1988, Biochem. J. 250:467–475). Both strands of double-stranded cDNA clones were sequenced by the dideoxy chain termination method using the Sequenase kit (U.S. Biochemical Corp.) and a combination of synthetic oligonucleotide primers, SK, KS, universal, and reverse primers. Human genomic DNA and poly $(A)^+$ RNA from both fetal and adult brain were obtained from Clontech. Incubations were at 65° C. for 48 hr using double stranded [$^{32}$P]-labeled probes prepared by random oligonucleotide priming.

6.3.2. cDNA CLONING

A human testis cDNA library (Clontech) was used for the isolation of the 1.7-kb TLE 3α cDNA. This cDNA was used to screen a human fetal brain cDNA library (Stratagene) resulting in isolation of the TLE 1, TLE 2, TLE 3, and TLE 4 cDNAs. Recombinant phage were propagated in E. coli "XL1-Blue" cells. Plaques were screened using the TLE 3α cDNA labeled with [$^{32}$P]-dCTP by random oligonucleotide priming as a probe. Replicate filters were hybridized at 65° C. in buffer A [500 mM sodium phosphate (pH 7.2), 5% SDS, 1 mM EDTA., and 1% bovine serum albumin (BSA)]. Filters were washed at 65° C. three times with a buffer containing 40 mM sodium phosphate (pH 7.2), 4% SDS, and 1 mM EDTA, and three times with the same buffer containing 1% SDS. After two further rounds of plaque hybridization, 14 unique clones were isolated. Cloned inserts were recovered after in vivo excision and recircularization of the "pBluescript SK (–)" phagemids from XL1-Blue cells in the presence of the R408 helper phage. Infection of E. coli cells with the obtained phagemids yielded colonies harboring double-stranded phagemid DNA. The size of individual inserts was determined by agarose gel electrophoresis after digestion with EcoRI.

6.3.3. CELL CULTURE AND PREPARATION OF CELL AND TISSUE EXTRACTS

Human HeLa cells were obtained from the American Type Culture Collection, Rockville, Md. Cells were grown at 37° C. in an atmosphere of 5% $CO_2$, 95% air in the presence of MEM (Eagle) supplemented with non-essential amino acids, Earle's BSS, 10% fetal bovine serum (FBS), 2 mM L-glutamine, 100 units/ml penicillin, 100 µg/ml streptomycin, and 0.25 µg/ml fungizone. Cells from stock cells were dissociated by addition of phosphate-buffered saline (PBS) containing 0.25% trypsin and 0.03% EDTA, and subcultured at a ratio of 1:3 to 1:5. For preparation of protein extracts, all operations were carried out at 4° C. Cells were resuspended in buffer B (10 mM HEPES, pH 7.8, 150 mM NaCl, 2 mm $MgCl_2$, 1 mM phenyl methylsulfonyl fluoride (PMSF), 2 µM leupeptin, 2.5 µg/ml aprotinin, and 2.5 µg/ml pepstatin A), homogenized using a Dounce homogenizer (10 strokes; type-A pestle), and protein extracts were obtained in the presence of 1% Triton X-100. Lysates were centrifuged at 12,000× g for 15 min and the resulting supernatants were collected, calibrated for their protein content, and subjected to SDS-PAGE. Human tissue samples were processed essentially in the same way.

6.3.4. IMMUNOFLUORESCENCE MICROSCOPY

HeLa cell monolayers were grown in tissue culture chamber slides (Nunc). Indirect immunofluorescence microscopy using the rat monoclonal antibody C597.4A (see infra) was performed essentially as described by Fehon et al. (1990, Cell 61:523–534). Cells were fixed with freshly made 2% (w/v) paraformaldehyde in 100 mM PIPES (pH 6.8), 2 mM EGTA, 1 mM $MgSO_4$, and incubated for 30 min in PBS containing 0.08% Triton X-100 and 3% normal goat serum (buffer C). After this, cells were incubated for 1 hr in buffer C containing a 1:10 dilution of the rat monoclonal antibody C597.4A, directed against a TLE 3/glutathione S-transferase fusion protein (see below). At the end of this incubation, cells were washed four times with buffer C and then incubated for 1 hr in buffer C containing a 1:1000 dilution of Cy3-conjugated goat anti-rat IgG (Jackson Immunoresearch Laboratories). Cells were then rinsed four times with buffer C, incubated for 1 min in PBS containing 1 µg/ml of DAPI, rinsed extensively with PBS, and processed for immunoflourescence as described in Fehon et al. (1990, Cell 61:523–534).

6.3.5. METABOLIC LABELING OF DROSOPHILA S2 CELL, IMMUNOPRECIPITATION, ELECTROPHORETIC PROCEDURES, AND WESTERN BLOTTING

Drosophila S2 cells were cultured as described previously (Fehon et al., 1990, Cell 61:523–534). In a typical metabolic labeling reaction with [$^{32}$P]-orthophosphate, 10–15 ml of cell suspension (~2×10$^7$ cells/mi) was used. Cells were washed twice with BSS, resuspended in 1 ml of phosphate-free M3 medium, and incubated at 24° C. for 45 min. After this time, cells were incubated for 3 hr at 24° C. in the presence of 750 µCi/ml of [$^{32}$P]-orthophosphate (Amersham; 370 MBq/ml). Incubations were performed in 6-well tissue culture plates with gentle rocking motion. At the end of the incubation time, cells were collected, washed twice with ice-cold buffer D (10 mM HEPES, pH 7.8, 60 mM KCl, 15 mM NaCl, 50 mM NaF, 10 mM sodium pyrophosphate, 5 mM $MgCl_2$, 300 mM sucrose, 1 mM PMSF, 2 µg/M leupeptin, 2.5 µg/ml aprotinin, 2.5 µg/ml pepstatin A), resuspended, and lysed in buffer D containing 0.5% Triton X-100. For immunoprecipitation experiments, cell lysates were mixed with the appropriate antibodies (150 µg/ml) and incubated for 2 hr at 4° C. in the presence of 3.5 mg/ml of BSA. Immunoprecipitates were collected by incubation with protein G-agarose beads, washed extensively with buffer E (25 mM Tris-HCl, pH 7.8, 200 mM NaCl, 2 mM EDTA, 2 mM EGTA, 20 mM NaF, 10 mM sodium pyrophosphate, and 0.5% Triton X-100), and subjected to SDS-polyacrylamide gel electrophoresis.

6.3.6. PREPARATION OF DROSOPHILA EMBRYONIC EXTRACTS

Staged Drosophila Canton-S embryos were collected, dechorionated in 50% Clorox solution, and washed extensively with 0.7% NaCl, 0.002% Triton X-100. Dechorionated embryos were washed twice in PBS and then homogenized by 10 strokes of a Dounce homogenizer (type-A pestle) in buffer F (10 mM HEPES, pH 7.8, 150 mM NaCl, 2 mM $MgCl_2$, 1 mM PMSF, 2 µM leupeptin, 2.5 µg/ml aprotinin, and 2.5µg/ml pepstatin A). All operations were carried out at 4° C. After incubation in the presence of 1% Triton X-100, homogenates were centrifuged at 12,000× g for 15 min and the supernatants were collected. Determination of the protein concentration of embryonic and cell extracts was obtained using the Biorad protein assay kit using BSA as standard.

6.3.7. PREPARATION OF FUSION PROTEINS AND IMMUNOLOGICAL PROCEDURES

Fusion proteins were obtained using the pGEX-3X expression vector system in E. coli BL21DE3 cells. The 1.7-kb testis cDNA subcloned in Bluescript SK II was excised with BamHI and EcoRV and ligated in frame into pGEX-3X. This fragment encodes the carboxyl-terminal 282 amino acid residues of the TLE 3 protein. This fusion construct produced an ~55-kDa chimeric protein containing the carboxyl terminus of glutathione S-transferase. Fusion proteins were produced and purified according to standard procedures (Smith and Johnson, 1988, Gene 67:31–40) and utilized for immunization of Long Evans rats according to the schedule described in Stifani et al. (1988, Biochem. J. 250:467–475). The hybridoma cell line C597.4A was obtained from a rat immunized with the TLE 3 fusion protein as described above.

7. TLE PROTEINS ARE PART OF HIGH-MOLECULAR-WEIGHT MULTIPROTEIN COMPLEXES

Both in Drosophila and man the TLE proteins (the terminology "TLE" applies in general to both the fly and human homologs) are present as part of high-molecular-weight (high $M_r$) multiprotein complexes. This was demonstrated by using a combination of non-denaturing polyacrylamide gel electrophoresis (PAGE), gel filtration, and cross-linking experiments. The results of such investigations are described below, together with the details of the experimental procedures.

7.1. NON-DENATURING PAGE

We subjected a high-speed supernatant fraction from HeLa cell lysates to electrophoresis through non-denaturing polyacrylamide gels. After electrophoresis, proteins were transferred to nitrocellulose filters and the replicas were used in Western blotting experiments with the monoclonal antibody C597.4A, which cross-reacts with all TLE proteins. As shown in FIG. 9, two major immunoreactive species were observed, with apparent molecular weights of greater than 670,000. Since the expected molecular weight of the monomeric TLE proteins is roughly 85,000, these results suggest that in their native state the TLE proteins are associates with other proteins to form high-molecular-weight complexes. Corresponding immunoreactive components were also visualized when polyclonal antibodies specific for TLE 1 were used (not shown).
Methods:

HeLa cells were grown at 37° C. in an atmosphere of 5% $CO_2$, 95% air in the presence of MEM (Eagle) supplemented with non-essential amino acids, 10% FBS, 2 mM L-glutamine, 100 units/ml penicillin, 100 µg/ml streptomycin, and 0.25 µg/ml fungizone. Cells were collected by scraping, washed once with ice-cold PBS, resuspended in ice-cold buffer G (50 mM HEPES, pH 7.6, 10 mM iodoacetic acid, 10 mM KCl, 0.5 mM EGTA, 0.5 mM EDTA, 1 mM PMSF, 2 µM leupeptin, 2.5 µg/ml aprotinin, 2.5 µg/ml pepstatin A, and 2.5 µg/ml antipain), and homogenized by 10 strokes of a Dounce homogenizer (teflon pestle). The homogenate was centrifuged at 100,000× g for 1 hr and the supernatant was recovered and immediately loaded onto 3–18% non-denaturing polyacrylamide gels. (This lysis procedure results in the recovery of more than 90% of the total cellular content of TLE proteins in the high-speed supernatant fraction.) Electrophoresis was performed at 150 V for 24 hr using a running buffer containing 90 mM Tris Base, 80 mM boric acid, and 3 mM EDTA (pH 8.4). After electrophoretic transfer of proteins to nitrocellulose, Western blotting experiments were performed as described in Section 6, supra, in the presence of a 1:20 dilution of monoclonal antibody C597.4A.

7.2. GEL FILTRATION CHROMATOGRAPHY

High-speed supernatant fractions from HeLa cells prepared as described above were subjected to gel filtration chromatography using a Sephacryl S-300 matrix. The fractions collected from the column were analyzed for the presence of TLE proteins in Western blotting experiments with monoclonal antibody C597.4A. As shown in FIG. 10A, TLE proteins were detected in fractions expected to contain molecules of size significantly larger than that predicted for the monomeric TLE proteins (see lanes 2–8). These results are therefore in agreement with the studies shown in FIG. 9 in suggesting the presence of large protein complexes containing the TLE proteins. The heterogeneous nature of such complexes, suggested by the presence of multiple bands in FIG. 9, is confirmed by the detection of TLE proteins in several column fractions spanning a large size interval (cfr. positions of elution of molecular size markers on top of FIG. 10A; D. B. Dextran Blue). When the same column fractions were subjected to electrophoresis under non-reducing conditions, additional bands were visualized with monoclonal antibody C597.4A (FIG. 10A). In particular, the presence of bands corresponding to species exhibiting slightly slower electrophoretic mobility than that of the TLE proteins suggests the existence of small proteins ($M_r$, 15,000–18,000) that can remain associated with the TLE proteins under these experimental conditions, but not under those used in FIG. 10A.
Methods:

High-speed supernatant from HeLa cells prepared as described above was loaded onto a Sephacryl S-300 HR column (110×1.5 cm), and elution was carried out in a buffer containing 50 mM HEPES, pH 7.4 and 100 mM NaCl at a flow rate of 10 ml/hr. 1-ml fractions were collected and 130-µl aliquots from each fraction were subjected to electrophoresis on a 4–18% SDS-polyacrylamide gel, followed by transfer to nitrocellulose and immunoblotting with monoclonal antibody C597.4A as described for FIG. 9. In FIG. 10A, samples were treated with 50 mM DTT and were heated to 95° C. prior to electrophoresis (reducing conditions). Under non-reducing conditions (FIG. 10 B) these two steps were omitted.

7.3. CROSS-LINKING STUDIES

We incubated protein extracts from Drosophila embryos (FIG. 11A), HeLa cells (FIG. 11B), or SUP-T1 cells (FIG.

11C) in the presence of increasing concentrations of the chemical cross-linker, DTSSP [3,3'-dithiobis (sulfosuccinimidylpropionate)]. The products of the cross-linking reactions were then subjected to electrophoresis on SDS-polyacrylamide gels, followed by transfer to nitrocellulose and Western blotting. These experiments showed that the presence of the cross-linker in the reaction mixtures results in the appearance of new immunoreactive components of higher apparent $M_r$. In the case of Drosophila embryonic extracts, Western blotting revealed, in addition to the monomeric form of the Enhancer of split m9/10 protein (apparent $M_r$, 82,000), three bands at roughly 170-, 190-, and 230 kD, plus two additional components of very slow electrophoretic mobility (FIG. 11A). Similarly, cross-linking reactions with either HeLa or SUP-T1 cell lysates led to the identification of new immunoreactive species of roughly 170-, 190-, and 230 kD (FIGS. 11B and 11C). These experiments also confirmed the observation shown in FIGS. 10A-10B, namely that 15-18-kD-proteins seem to be capable of interacting with the TLE proteins. As shown both in the case of HeLa and SUP-T1 cells, cross-linking reactions facilitated detection of ~110-kD species (see FIG 11B, lane 6 and FIG. 11C, lane 9), likely reflecting the association of TLE proteins with low $M_r$ components. Although it is not possible from these experiments to further characterize the composition of the various products of the cross-linking reactions, the apparent molecular weights of some of them indicate that they do not simply represent oligomeric forms of the TLE proteins, but must involve other unrelated proteins. Even though no immunoreactive products could be detected in the 110-kD range when these experiments were performed with Drosophila embryonic extracts, it is worth noting that an approximately 17-kD protein was co-immunoprecipitated from the metabolically labelled Drosophila S2 cell lysates using a monoclonal antibody directed against Enhancer of split m9/10. Thus it seems that the molecular associations involving TLE proteins have been conserved from flies to humans.

Methods:

4-10-hr Drosophila Canton S embryos were collected, dechorionated in 50% Clorox solution, and washed extensively with 0.7% NaCl, 0.02% Triton X-100. Dechorionated embryos were washed twice in ice-cold PBS and then homogenized by 10 strokes of a Dounce homogenizer in buffer H (10 mM HEPES, pH 7.6, 150 mM NaCl, 0.5 mM EDTA, 0.5 mM EGTA, 1mM PMSF, 2 µM leupeptin, 2.5 µg/ml aprotinin, 2.5 µg/ml pepstalin A, and 2.5 µg/ml antipain). The homogenate was centrifuged at 13,000×g for 15 min and the supernatant was recovered and used in the cross-linking experiments. HeLa and SUP-T1 cell lysates were prepared as described in Section 7.1 except that the homogenates were centrifuged at 8,000×g for 5 min. The resulting supernatants were collected and immediately incubated with the cross-linking agent, DTSSP. Cross-linking reactions were carried out for 30 min at room temperature in the presence of the amounts of DTSSP indicated in FIGS. 11A-11C. At the end of the incubations, glycine and Tris/HCl (pH 8.0) were added to a final concentration of 40 mM each, samples were further incubated for 5 min, and then subjected to SDS-PAGE under non-reducing conditions on 4-15% gradient gels. Following electrophoretic transfer to nitrocellulose, membranes were probed with either monoclonal antibody 3C, directed against Enhancer of split m9/10 (FIG. 11A), or monoclonal antibody C597.4A, directed against the TLE proteins (lanes FIGS. 11B and 11C).

In summary, these combined results demonstrate that the TLE proteins can interact with other proteins. One such component of these large complexes appears to be a ~17-kD protein(s) that can be detected both in Drosophila and man.

7.4. FURTHER CHARACTERIZATION OF MULTIPROTEIN COMPLEXES CONTAINING TLE PROTEINS

In order to investigate more thoroughly the composition of these protein complexes, we have obtained a panel of unique monoclonal antibodies by immunizing animals with a crude preparation of the TLE complex isolated from HeLa cells. These reagents should allow us to identify additional candidate members of the complex, e.g., as follows: The TLE complex is isolated from HeLa cells by obtaining the appropriate gel filtration fractions (FIGS. 10A-10B). The appropriate fractions containing the complex are then subjected to SDS-PAGE analysis (both under reducing and non-reducing conditions), followed by Western blotting with (a) one of the unique monoclonal antibodies described above; and (b) a monoclonal antibody against one or more of the TLE proteins. An individual protein that is a member of the multiprotein TLE complex is identified by its ability (a) after SDS-PAGE under reducing conditions, to be bound by the unique monoclonal antibody; and (b) after PAGE under nondenaturing conditions, to be bound by the unique monoclonal antibody while in a multiprotein complex, which complex is also able to be bound by the anti-TLE antibody. Cross-linking reagents and immunoprecipitation experiments can also be employed. Furthermore, we have raised antibodies specific for either TLE 1 or TLE 2; these also can be used to characterize the components of the TLE complexes.

8. TLE EXPRESSION IN NORMAL AND MALIGNANT CELLS

Various human patient tissue samples and cell lines, representing both normal and a wide variety of malignant cells are assayed to detect and/or quantitate expression of TLE protein. Patient tissue samples are obtained from the pathology department at the Yale University School of Medicine.

The following assays are used to measure TLE expression in patient tissue samples: (a) Northern hybridization; (b) Western blots; (c) in situ hybridization; and (d) immunocytochemistry. Assays are carried out using standard techniques. Northern hybridization and in situ hybridization are carried out using a DNA probe specific to a human TLE sequence. Western blots and immunocytochemistry are carried out using an antibody to human TLE protein.

Northern hybridization and Western blots, as described above, are also used to analyze numerous human cell lines, representing various normal or cancerous tissues. The cell lines tested are listed in Table 2.

TABLE 2

| HUMAN CELL LINES | |
|---|---|
| Tissue/Tumor | Cell line |
| Bone marrow | IM-9 |
|  | KG-1 |
| Brain | A-172 |
|  | HS 683 |
|  | U-87MG |
|  | TE 671 |
| Breast | BT-20 |
|  | Hs 578Bs |

TABLE 2-continued

HUMAN CELL LINES

| Tissue/Tumor | Cell line |
|---|---|
| Colon | MDA-MB-330 |
|  | Caco-2 |
|  | SW 48 |
|  | T84 |
|  | WiDr |
| Embryo | FHs 173We |
| Kidney | A-498 |
|  | A-704 |
|  | Caki-2 |
| Leukemia | ARH-77 |
|  | KG-1 |
| Liver | Hep G2 |
|  | WRL 68 |
| Lung | Calu-1 |
|  | HLF-a |
|  | SK-Lu-1 |
| Lymphoblasts | CCRF-CEM |
|  | HuT 78 |
| Lymphoma | Hs 445 |
|  | MS116 |
|  | U-937 |
| Melanoma | A-375 |
|  | G-361 |
|  | Hs 294T |
|  | SK-MEL-1 |
| Myeloma | IM-9 |
|  | RPMI 8226 |
| Neuroblastoma | IMR-32 |
|  | SK-N-SH |
|  | SK-N-MC |
| Ovary | Caov-3 |

TABLE 2-continued

HUMAN CELL LINES

| Tissue/Tumor | Cell line |
|---|---|
|  | Caov-4 |
|  | PA-1 |
| Plasma Cells | ARH-77 |
| Sarcoma | A-204 |
|  | A673 |
|  | HOS |
| Skin | Amdur II |
|  | BUD-8 |
| Testis | Tera-1 |
|  | Tera-2 |
| Thymus | Hs67 |
| Uterus | AN3 Ca |
|  | HEC-1-A |

Malignancies of malignant cell tissue types which are thus shown to specifically express TLE can be treated as described in Section 5.1 et seq.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method of aiding in the diagnosing of malignancy or metaplasia characterized by an increase in the level of transducin-like Enhancer of split protein in a patient, comprising measuring the level of transducin-like Enhancer of split protein in a sample derived from the patient, in which an increase in transducin-like Enhancer of split protein in the patient sample relative to the level found in such a sample from a normal individual indicates the presence of the malignancy or metaplasia in the patient, and thereby aiding in the diagnosing of the malignancy or metaplasia in the patient.

2. The method according to claim 1 which is for aiding in the diagnosis of cervical cancer.

3. The method according to claim 1 which is for aiding in the diagnosis of colon carcinoma.

4. The method according to claim 1 which is for aiding in the diagnosis of adenocarcinoma.

5. The method according to claim 1 which is for aiding in the diagnosis of adenocarcinoma of the cervix.

6. The method according to claim 1 which is for aiding in the diagnosis of cervical metaplasia.

7. The method according to claim 1 in which the level of transducin-like Enhancer of split protein is measured by a method comprising:

(a) contacting the sample with an antibody reactive with the transducin-like Enhancer of split protein under conditions such that immunospecific binding can occur; and (b) measuring the amount of any immunospecific binding that occurs between the antibody and a component in the sample, in which the amount of immunospecific binding indicates the level of transducin-like Enhancer of split protein, and thereby measuring the level of transducin-like Enhancer of split protein.

8. The method according to claim 7 which is for aiding in the diagnosis of cervical cancer.

9. The method according to claim 7 which is for aiding in the diagnosis of colon carcinoma.

10. The method according to claim 7 which is for aiding in the diagnosis of adenocarcinoma.

11. The method according to claim 7 which is for aiding in the diagnosis of adenocarcinoma of the cervix.

12. The method according to claim 7 which is for aiding in the diagnosis of cervical metaplasia.

* * * * *